US007882394B2

(12) United States Patent  
Hosek et al.

(10) Patent No.: US 7,882,394 B2  
(45) Date of Patent: Feb. 1, 2011

(54) INTELLIGENT CONDITION-MONITORING AND FAULT DIAGNOSTIC SYSTEM FOR PREDICTIVE MAINTENANCE

(75) Inventors: Martin Hosek, Lowell, MA (US); Jay Krishnasamy, Billerica, MA (US); Jan Prochazka, Hudson, NH (US)

(73) Assignee: Brooks Automation, Inc., Chelmsford, MA (US)

( * ) Notice: Subject to any disclaimer, the term of this patent is extended or adjusted under 35 U.S.C. 154(b) by 405 days.

(21) Appl. No.: 11/485,143

(22) Filed: Jul. 11, 2006

(65) Prior Publication Data

US 2007/0067678 A1    Mar. 22, 2007

Related U.S. Application Data

(60) Provisional application No. 60/698,521, filed on Jul. 11, 2005.

(51) Int. Cl.  
*G06F 11/30* (2006.01)

(52) U.S. Cl. .............................. 714/26; 714/47; 714/48; 714/25; 702/184

(58) Field of Classification Search .................. 714/26, 714/47; 702/184, 183, 185  
See application file for complete search history.

(56) References Cited

U.S. PATENT DOCUMENTS

| | | | |
|---|---|---|---|
| 4,825,808 A | 5/1989 | Takahashi et al. | ........... 118/719 |
| 4,914,437 A * | 4/1990 | Kibrick et al. | ................. 341/3 |
| 5,204,618 A | 4/1993 | Matsuoka | |
| 5,408,406 A | 4/1995 | Mathur et al. | |
| 5,445,347 A | 8/1995 | Ng | |
| 5,469,447 A | 11/1995 | Brunemann, Jr. et al. | |
| 5,521,482 A * | 5/1996 | Lang et al. | .................. 318/800 |
| 5,566,092 A | 10/1996 | Wang et al. | |
| 5,568,003 A * | 10/1996 | Deck | ...................... 310/316.01 |
| 5,573,088 A * | 11/1996 | Daniels | ..................... 188/267 |
| 5,642,296 A | 6/1997 | Saxena | |
| 5,695,564 A | 12/1997 | Imahashi | ..................... 118/719 |
| 5,754,449 A * | 5/1998 | Hoshal et al. | ............... 702/187 |
| 5,761,090 A * | 6/1998 | Gross et al. | .................. 714/26 |
| 5,788,447 A | 8/1998 | Yonemitsu et al. | .......... 414/217 |
| 5,800,331 A * | 9/1998 | Song | ............................ 494/7 |
| 5,840,092 A * | 11/1998 | Rick et al. | .................... 55/472 |
| 5,844,744 A * | 12/1998 | Suzuki et al. | ............ 360/78.09 |

(Continued)

OTHER PUBLICATIONS

Melan et al, Quality and Reliability Assurance Systems in IBM Semiconductor Manufacturing Other Papers, Sep. 30, 1982, UTC United States, Previously published in the SPI Database of Software Technologies, IBMRD, vol. 26, No. 5, Sep. 1982.

(Continued)

*Primary Examiner*—Scott T Baderman  
*Assistant Examiner*—Chae Ko  
(74) *Attorney, Agent, or Firm*—Perman & Green, LLP

(57) ABSTRACT

A system for condition monitoring and fault diagnosis includes a data collection function that acquires time histories of selected variables for one or more of the components, a pre-processing function that calculates specified characteristics of the time histories, an analysis function for evaluating the characteristics to produce one or more hypotheses of a condition of the one or more components, and a reasoning function for determining the condition of the one or more components from the one or more hypotheses.

209 Claims, 20 Drawing Sheets

U.S. PATENT DOCUMENTS

| | | | |
|---|---|---|---|
| 5,844,850 | A | 12/1998 | Tsutsui et al. |
| 5,882,165 | A | 3/1999 | Maydan et al. .............. 414/217 |
| 5,959,861 | A * | 9/1999 | Kaneko ........................ 700/29 |
| 5,988,645 | A * | 11/1999 | Downing .................... 273/348 |
| 6,004,050 | A * | 12/1999 | Rehman et al. ............. 400/319 |
| 6,016,465 | A | 1/2000 | Kelly |
| 6,025,726 | A * | 2/2000 | Gershenfeld et al. ........ 324/671 |
| 6,085,154 | A | 7/2000 | Leuthausser et al. |
| 6,086,177 | A * | 7/2000 | Driendl et al. .............. 318/466 |
| 6,122,042 | A * | 9/2000 | Wunderman et al. .......... 356/73 |
| 6,122,585 | A * | 9/2000 | Ono et al. ..................... 701/71 |
| 6,141,848 | A * | 11/2000 | Yousko et al. ............... 29/33 K |
| 6,148,420 | A * | 11/2000 | Schlater et al. ............... 714/39 |
| 6,175,812 | B1 | 1/2001 | Boyington et al. |
| 6,182,001 | B1* | 1/2001 | Sugai et al. .................... 701/78 |
| 6,198,976 | B1 | 3/2001 | Sundar et al. ................. 700/59 |
| 6,199,018 | B1 | 3/2001 | Quist et al. |
| 6,223,544 | B1 | 5/2001 | Seem |
| 6,317,701 | B1 | 11/2001 | Pyotsia et al. |
| 6,321,157 | B1* | 11/2001 | Sun et al. .................... 701/103 |
| 6,356,857 | B1 | 3/2002 | Qin et al. |
| 6,374,677 | B1* | 4/2002 | Berlin et al. .................. 73/662 |
| 6,377,705 | B1* | 4/2002 | Sato et al. ................... 382/197 |
| 6,377,880 | B1* | 4/2002 | Kato et al. .................... 701/29 |
| 6,393,373 | B1 | 5/2002 | Duyar et al. |
| 6,434,512 | B1 | 8/2002 | Discenzo |
| 6,483,938 | B1 | 11/2002 | Hennessey et al. .......... 382/149 |
| 6,498,992 | B1 | 12/2002 | Toyota et al. |
| 6,523,872 | B2* | 2/2003 | Breed .......................... 293/119 |
| 6,556,153 | B1* | 4/2003 | Cardamone ................. 341/111 |
| 6,577,934 | B2 | 6/2003 | Matsunaga et al. |
| 6,587,812 | B1 | 7/2003 | Takayama |
| 6,590,362 | B2 | 7/2003 | Parlos et al. |
| 6,598,195 | B1 | 7/2003 | Adibhatla et al. |
| 6,615,090 | B1* | 9/2003 | Blevins et al. ................. 700/26 |
| 6,651,012 | B1 | 11/2003 | Bechhoefer |
| 6,684,349 | B2 | 1/2004 | Gullo et al. |
| 6,740,534 | B1 | 5/2004 | Adams, III et al. |
| 6,750,866 | B1* | 6/2004 | Anderson, III .............. 345/474 |
| 6,804,600 | B1 | 10/2004 | Uluyol et al. |
| 6,816,815 | B2 | 11/2004 | Takayama |
| 6,845,468 | B2* | 1/2005 | James ........................... 714/25 |
| 6,852,194 | B2 | 2/2005 | Matsushita et al. ..... 156/345.32 |
| 6,862,486 | B2 | 3/2005 | Cocco et al. |
| 6,894,526 | B2 | 5/2005 | Marr |
| 6,962,471 | B2 | 11/2005 | Birkner et al. .............. 414/217 |
| 7,019,548 | B2 | 3/2006 | Miao et al. |
| 7,024,335 | B1 | 4/2006 | Parlos |
| 7,065,725 | B2 | 6/2006 | Yajima et al. |
| 7,079,982 | B2 | 7/2006 | Ogura et al. |
| 7,082,359 | B2 | 7/2006 | Breed |
| 7,090,741 | B2 | 8/2006 | Narushima et al. ..... 156/345.26 |
| 7,146,292 | B2 | 12/2006 | Rossi et al. |
| 7,171,337 | B2 | 1/2007 | Yuan et al. |
| 7,171,585 | B2 | 1/2007 | Gail et al. |
| 7,200,524 | B2 | 4/2007 | Kang et al. |
| 7,203,561 | B2 | 4/2007 | Sugihara et al. |
| 7,292,058 | B2 | 11/2007 | Anderson et al. |
| 7,379,782 | B1 | 5/2008 | Cocco |
| 7,380,172 | B2 | 5/2008 | Srinivas et al. |
| 7,401,263 | B2* | 7/2008 | Dubois et al. ................. 714/47 |
| 2001/0008541 | A1* | 7/2001 | Andersen ....................... 374/45 |
| 2001/0010464 | A1* | 8/2001 | Takamori et al. ............ 324/304 |
| 2001/0018846 | A1* | 9/2001 | Shin ............................. 73/116 |
| 2001/0037477 | A1* | 11/2001 | Veenstra et al. ............... 714/41 |
| 2002/0078843 | A1* | 6/2002 | Gorbing et al. ............. 101/232 |
| 2002/0082924 | A1 | 6/2002 | Koether |
| 2002/0159864 | A1* | 10/2002 | Lowrance ................... 414/217 |
| 2002/0161499 | A1* | 10/2002 | Radamis et al. ............... 701/41 |
| 2002/0161548 | A1* | 10/2002 | Elliott et al. ................. 702/151 |
| 2002/0184568 | A1* | 12/2002 | Kurrasch ..................... 714/39 |
| 2003/0011380 | A1* | 1/2003 | Harzanu et al. ............. 324/529 |
| 2003/0014692 | A1* | 1/2003 | James et al. .................. 714/25 |
| 2003/0034995 | A1 | 2/2003 | Osborn et al. |
| 2003/0051191 | A1* | 3/2003 | Circenis et al. ............... 714/25 |
| 2003/0060094 | A1* | 3/2003 | Motsenbocker ................ 440/6 |
| 2003/0063123 | A1* | 4/2003 | Fukube et al. .............. 345/771 |
| 2003/0065486 | A1* | 4/2003 | Sumida et al. .............. 702/189 |
| 2003/0079012 | A1* | 4/2003 | Marsland .................... 709/224 |
| 2003/0145249 | A1* | 7/2003 | Wilson et al. ................. 714/25 |
| 2003/0171827 | A1* | 9/2003 | Keyes et al. .................. 700/19 |
| 2003/0204788 | A1* | 10/2003 | Smith ........................... 714/47 |
| 2003/0209893 | A1* | 11/2003 | Breed et al. ................. 280/735 |
| 2003/0215030 | A1* | 11/2003 | Hurley ........................ 375/322 |
| 2004/0030524 | A1* | 2/2004 | Jarrell et al. ................. 702/113 |
| 2004/0036261 | A1* | 2/2004 | Breed ......................... 280/735 |
| 2004/0044442 | A1* | 3/2004 | Bayoumi et al. ............ 700/286 |
| 2004/0111237 | A1 | 6/2004 | Vlok |
| 2004/0162639 | A1* | 8/2004 | Watanabe et al. ........... 700/259 |
| 2004/0236559 | A1* | 11/2004 | Chen ........................... 703/18 |
| 2004/0243636 | A1* | 12/2004 | Hasiewicz et al. ........ 707/104.1 |
| 2005/0004780 | A1* | 1/2005 | Lin et al. .................... 702/184 |
| 2005/0068667 | A1* | 3/2005 | Burns et al. .............. 360/99.08 |
| 2005/0074140 | A1* | 4/2005 | Grasso et al. ................ 382/103 |
| 2005/0116836 | A1* | 6/2005 | Perry et al. ............ 340/870.02 |
| 2005/0177321 | A1* | 8/2005 | Wang et al. ................... 702/35 |
| 2005/0197803 | A1* | 9/2005 | Eryurek et al. .............. 702/185 |
| 2005/0257078 | A1 | 11/2005 | Bose et al. |
| 2006/0048017 | A1* | 3/2006 | Anerousis et al. ............. 714/47 |
| 2006/0080062 | A1 | 4/2006 | Bose et al. |
| 2006/0082160 | A1* | 4/2006 | Lee .............................. 290/55 |
| 2007/0143718 | A1 | 6/2007 | Abercrombie et al. |
| 2007/0274304 | A1 | 11/2007 | Lycette |
| 2007/0280706 | A1 | 12/2007 | Yasukawa et al. |
| 2008/0015827 | A1 | 1/2008 | Tryon, III et al. |

OTHER PUBLICATIONS

Djurdjanovic et al, Similarity based method for manufacturing process performance prediction and diagnosis, Computers in Industry, 2007, vol. 58, No. 6, pp. 558-566.

Zhou et al, Intelligent prediction monitoring system for predictive maintenance in manufacturing, Singapore Inst. of Manuf. Technol., Nayang, Singapore, Conference: IECON 2005, Thirty-First Annual Conference of the IEEE Industrial Electronics Society (IEEE Cat. No. 05CH37699), p. 6, IEEE, Piscataway, NJ, USA, 2005, CD-ROM pages, Conference: IECON 2005, Thirty-First Annual Conference of the IEEE Industrial Electronics Society, Nov. 6-10, 2005, Raleigh, NC, USA.

Interactive Fault Diagnosis in a Distribution System Using Artifical Intelligence, Aug. 14, 2006, UTC, USA, Disclosed by IBM.

Bossen et al, Model for Transient and Permanent Error-Detection and Fault-Isolation Coverage, Jan. 31, 1982, UTC, Previously published in the SPI Database of Software Technologies, IBMRD, vol. 26, No. 1, Jan. 1982.

Chen et al, Reliability prediction model of aircraft using self-organizing map, Civil Aviation Univ. of China, Tinjin, China, Conference: 2007 IEEE International Conference on Automation and Logistics, p. 680-683, IEEE, Piscataway, NJ, USA, 2007, Conference: IEEE International Conference on Automation and Logistics, Aug. 18-21, 2007, Jinan, China.

Wireless Maintenance Data Acquisition System, Aug. 8, 2007, UTC, United States.

* cited by examiner

Figure 10: Incremental encoder data integrity checking.

INTELLIGENT CONDITION-MONITORING AND FAULT DIAGNOSTIC SYSTEM FOR PREDICTIVE MAINTENANCE

This application claims the benefit of U.S. Provisional Application No. 60/698,521 filed 11 Jul. 2005, which is incorporated by reference herein in its entirety.

BACKGROUND

The disclosed embodiments are directed to a condition monitoring and fault diagnosis system.

BRIEF DESCRIPTION OF RELATED DEVELOPMENTS

Material damage and unscheduled downtime due to failures of robotic manipulators and other mechatronic devices used in automated manufacturing tools, such as robotized material-handling platforms for production of semiconductor devices, are common problems which often represent a significant cost burden to the end-user of the manufacturing tools.

A number of health-monitoring and fault-diagnostic (HMFD) methods have been developed for industrial, automotive and aerospace applications. The existing systems typically implement fault detection to indicate that something is wrong in the monitored system, fault isolation to determine the exact location of the fault, i.e., the component which is faulty, and fault identification to determine the magnitude of the fault.

The isolation and identification tasks together are often referred to as fault diagnosis. Many existing systems implement only the fault detection and isolation stages. Generally, the methods used for HMFD may be classified into two major groups: those which do not utilize a mathematical model of the system subject to monitoring and diagnostics, also referred to as the "plant," and those which do. The methods which do not use the mathematical model of the plant include physical redundancy, utilization of special sensors, limit checking, spectrum analysis, and logical reasoning.

In the physical redundancy approach, multiple sensors are installed to measure the same physical quantity. Any serious discrepancy between the measurements indicates a sensor fault. With only two parallel sensors, fault isolation may not be possible, however, with three or more sensors, a voting scheme may be formed which isolates the faulty sensor. Physical redundancy usually involves extra hardware cost and extra weight.

Special sensors may be installed explicitly for detection and diagnosis. These may be limit sensors (measuring, e.g., temperature or pressure), which perform limit checking (see below) in hardware. Other special sensors may measure some fault-indicating physical quantity, such as sound, vibration, elongation, etc.

In a limit checking approach, widely used in practice, plant measurements are compared by computer to preset limits. Exceeding the threshold indicates a fault situation. In many systems, there are two levels of limits, the first serving for pre-warning while the second triggering an emergency reaction. Limit checking may be extended to monitoring the time-trend of selected variables. While simple and straightforward, the limit checking approach suffers from two serious drawbacks:

(a) Since the plant variables may vary widely due to normal input variations, the test thresholds need to be set quite conservatively; and (b) The effect of a single component fault may propagate to many plant variables, setting off a confusing multitude of alarms and making isolation extremely difficult.

Spectrum analysis of plant measurements may also be used for detection and isolation. Most plant variables exhibit a typical frequency spectrum under normal operating conditions; any deviation from this may be an indication of abnormality. Certain types of faults may even have their characteristic signature in the spectrum, facilitating fault isolation.

Logical reasoning techniques form a broad class which are complementary to the methods outlined above in that they are aimed at evaluating the symptoms obtained by detection hardware and software. The simplest techniques include logical rules of the "if-symptom-and-symptom-then-conclusion" type. Each conclusion can, in turn, serve as a symptom in the next rule until the final conclusion is reached. The system may process the information presented by the detection hardware and software, or may interact with a human operator, inquiring from him or her about particular symptoms and guiding him or her through the entire logical process.

Turning now to methods which do use a mathematical model of the plant, these model-based condition-monitoring and fault-diagnostic methods generally rely on the concept of analytical redundancy. In contrast to physical redundancy, where measurements from parallel sensors are compared to each other, sensory measurements are compared to analytically computed values of the respective variable. Such computations use present and/or previous measurements of other variables, and a mathematical plant model describing their nominal relationship to the measured variable. The idea can be extended to the comparison of two analytically generated quantities, obtained from different sets of variables. In either case, the resulting differences, called residuals, are indicative of faults in the system. Another class of model-based methods relies directly on parameter estimation.

The generation of residuals needs to be followed by residual evaluation in order to arrive at detection and isolation decisions. Because of the presence of noise and model errors, the residuals are never zero, even if there is no fault. Therefore the detection decision requires testing the residuals against thresholds, which may be obtained empirically or by theoretical considerations. To facilitate fault isolation, the residual generators are usually designed for isolation enhanced residuals, exhibiting structural or directional properties. The isolation decisions then can be obtained in a structural (Boolean) or directional (geometric) framework, with or without the inclusion of statistical elements.

There are four somewhat overlapping approaches to residual generation in model-based condition monitoring and fault diagnostics: Kalman filter, diagnostic observers, parameter estimation and parity relations.

The prediction error of a Kalman filter can be used as a fault detection residual. Its mean is zero if there is no fault (and disturbance) and becomes nonzero in the presence of faults. Since the innovation sequence is white, statistical tests are relatively easy to construct. However, fault isolation is somewhat awkward with the Kalman filter; one needs to run a bank of "matched filters", one for each suspected fault and for each possible arrival time, and check which filter output can be matched with the actual observations.

Diagnostic observer innovations also qualify as fault detection residuals. "Unknown input" design techniques may be used to decouple the residuals from a limited number of disturbances. The residual sequence is colored, which makes statistical testing somewhat complicated. The freedom in the design of the observer can be utilized to enhance the residuals for isolation. The dynamics of the fault response can be controlled within certain limits by placing the poles of the observer.

Parameter estimation is a natural approach to the detection and isolation of parametric (multiplicative) faults. A reference model is obtained by first identifying the plant in a fault-free situation. Then the parameters are repeatedly re-identified on-line. Deviations from the reference model serve as a basis for detection and isolation. Parameter estimation may be more reliable than analytical redundancy methods, but it is also more demanding in terms of on-line computation and input excitation requirements.

Parity (consistency) relations are rearranged direct input-output model equations subjected to a linear dynamic transformation. The transformed residuals serve for detection and isolation. The residual sequence is colored, just like in the case of observers. The design freedom provided by the transformation can be used for disturbance decoupling and fault isolation enhancement. Also, the dynamics of the response can be assigned within the limits posed by the requirements of causality and stability.

The health-monitoring and fault-diagnostic methods directly applicable to semiconductor manufacturing systems have generally been limited to a small number of faults, for example, those associated with joint backlash. This may be because additional restrictions, such as variability of faults, unsteady and non-uniform operating conditions and limited availability of component characteristics collected over time exist in this area. The analytical methods described above have been primarily applied to systems that are defined by linear equations and are not directly applicable to systems whose dynamics are non-linear. There are, however, a few examples of robotic system applications using parameter identification, the Kalman filter approach, the use of multiple linear neural network models for robot fault diagnosis, and the use of a diagnostic observer for detecting faults in a simulated electro-hydraulic actuator.

It would be advantageous to provide an improved system for monitoring conditions and diagnosing faults.

SUMMARY OF THE DISCLOSED EMBODIMENTS

The embodiments disclosed herein are directed to a system for condition monitoring and fault diagnosis including a data collection function that acquires time histories of selected variables for one or more of the components, a pre-processing function that calculates specified characteristics of the time histories, an analysis function for evaluating the characteristics to produce one or more hypotheses of a condition of the one or more components, and a reasoning function for determining the condition of the one or more components from the one or more hypotheses.

In another embodiment, a method of component condition monitoring and fault diagnosis includes acquiring time histories of selected variables for one or more of the components, calculating specified characteristics of the time histories, evaluating the characteristics to produce one or more hypotheses of a condition of the one or more components, and determining the condition of the one or more components from the one or more hypotheses.

In another embodiment, a computer program product includes a computer usable medium having computer usable program code for component condition monitoring and fault diagnosis, that when run on a computer causes the computer to acquire time histories of selected variables for one or more of the components, calculate specified characteristics of the time histories, evaluate the characteristics to produce one or more hypotheses of a condition of the one or more components, and determine the condition of the one or more components from the one or more hypotheses.

Yet another embodiment includes a system for component condition monitoring and fault diagnosis having a data collection function that acquires time histories of selected variables for one or more components, a pre-processing function that calculates specified characteristics of the time histories, an analysis function for evaluating the characteristics to produce one or more hypotheses of a condition of the one or more components, a reasoning function for determining the condition of the one or more components from the one or more hypotheses, and a manager function that determines the selected variables acquired by the data collection function, triggers data processing in the pre-processing function for calculating the specified characteristics, initiates evaluation of the characteristics by the analysis function to yield the hypotheses, and triggers derivation of the component conditions by the reasoning function.

BRIEF DESCRIPTION OF THE DRAWINGS

The foregoing aspects and other features of the presently disclosed embodiments are explained in the following description, taken in connection with the accompanying drawings, wherein.

DETAILED DESCRIPTION OF THE PREFERRED EMBODIMENTS

Figure 1:
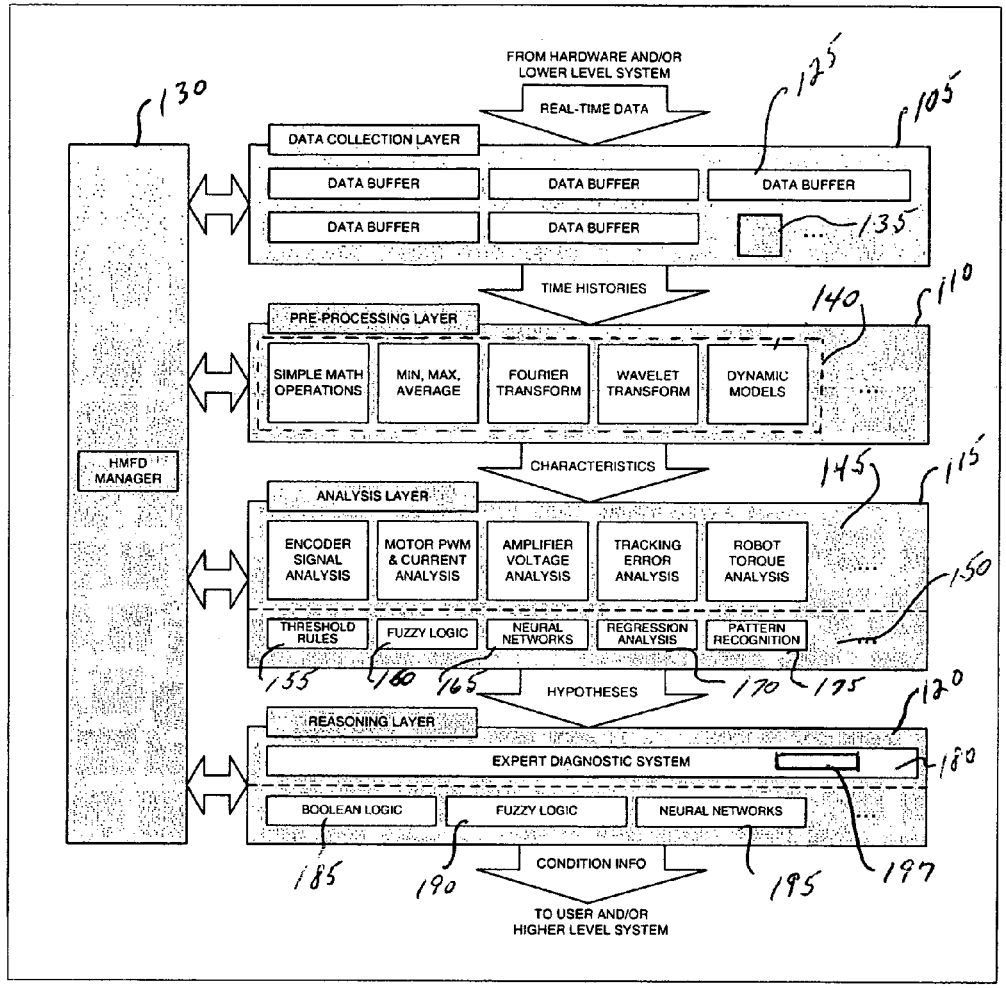
FIG. 1 shows a condition-monitoring and fault-diagnostic system according to the disclosed embodiments.

FIG. 1 shows a block diagram of a system 100 suitable for monitoring conditions and for diagnosing faults of a machine as disclosed herein. Although the disclosed embodiments are described with reference to the drawings, it should be understood that they may be implemented in many alternate forms. In addition, any suitable types, forms, or physical shapes of elements or materials could be used.

The disclosed embodiments are directed to a system and method for assessing the condition of system components, referred to as health monitoring, and performing fault diagnosis. As a result of the health monitoring and fault diagnosis functions, the system may also schedule predictive maintenance or service as required, and adjust system processes to maintain operations until maintenance or service may be performed.

Condition assessment refers to measuring characteristics, performance, outputs or other indicators of the operation of a system component to determine its condition. Fault diagnosis refers to the ability to identify a component fault from the indicators of operation, other component characteristics, or from system operations. Automated fault diagnosis may complement or relieve an operator from fault classification and troubleshooting tasks, including diagnostic error codes and interactive diagnostic screens.

Predictive maintenance refers to tasks performed to maintain proper operation while services refers to tasks performed on a non-operational component to restore it to operational status As shown in FIG. 1, the present system may include four functions: a data collection function 105, a pre-processing function 110, an analysis function 115, and a reasoning function 120. In addition, the operation of the functions 105 110, 115, 120 may be coordinated by a health-monitoring and fault-diagnostic manager 130. Each of the four functions 105, 110, 115, 120 and the manager 130 may be implemented in software, hardware, or any combination of both.

The software implemented portions of the system 100 may reside on one or more program storage devices encoded with a computer program, for example, machine readable program source code, which is adapted to cause one or more computers to perform the operations described in the disclosed embodiments. The program storage devices may include magnetic media such as a tape, disk, or computer hard drive, optical media, semiconductor media, or any other device suitable for storing a computer program.

It is a feature of the disclosed embodiments that the data collection function acquires time histories of selected variables during operation of the machine being monitored, the pre-processing function calculates specific characteristics of the acquired time histories, the analysis function evaluates characteristics of individual components with which the variables are associated and produces one or more hypotheses about the condition of each of the components, and the reasoning function derives an overall assessment of the machine, including the condition of the individual components of the machine and the degree of confidence that the machine is in good operating condition. For purposes of the disclosed embodiments, a machine may be an optical, mechanical, electrical, or electromechanical device, a computer software program, or any combination of the aforementioned items and may include any entity whose operation may be monitored.

It is a further feature of the disclosed embodiments that the system may be implemented in a hierarchically distributed manner. For example, multiple instances of each function may reside in, or be associated with, progressively higher level controllers within the machine such that the data required for health monitoring and fault diagnostic purposes are used at the level where sufficient intelligence to process the data is present.

As a further example, the machine may be a semiconductor production system with a master controller overseeing an atmospheric section with multiple robotic manipulators. Each manipulator may have a number of motors. An instance of the data collection function may reside in each motor controller, and an instance of the pre-processing function may reside in each robot controller that controls a group of motor controllers. The controller for the atmospheric section may hold an instance of the analysis function, and the master controller may hold an instance of the reasoning function. This hierarchical approach reduces network traffic by eliminating the need for real-time streaming of individual data points from each individual device controller upward through the system architecture to the master controller. This approach is also advantageous because it eliminates the need for upper level controllers to configure data collection processes for a variety of devices, each with different types of variables to monitor requiring different processing algorithms.

It should be noted that the hierarchical or distributed approach is different from existing centralized trends referred to as e-diagnostics. In e-diagnostics, all of the data necessary for health monitoring and fault diagnostics are transmitted to a high-level controller, such as the master controller mentioned above, and analyzed at this high level. This approach requires extremely high volumes of data to propagate from the low-level controllers all the way to the high-level controller, often in real time. In addition, the high-level controller needs to store properties of all of the components of the robotized system, such as motor parameters or kinematic and dynamic models of the robots, to be able to process the collected data.

Returning to FIG. 1, each function generally receives data from a lower level, processes the data and passes the processed data to the next function or ultimately to a user or higher level system.

Figure 2:
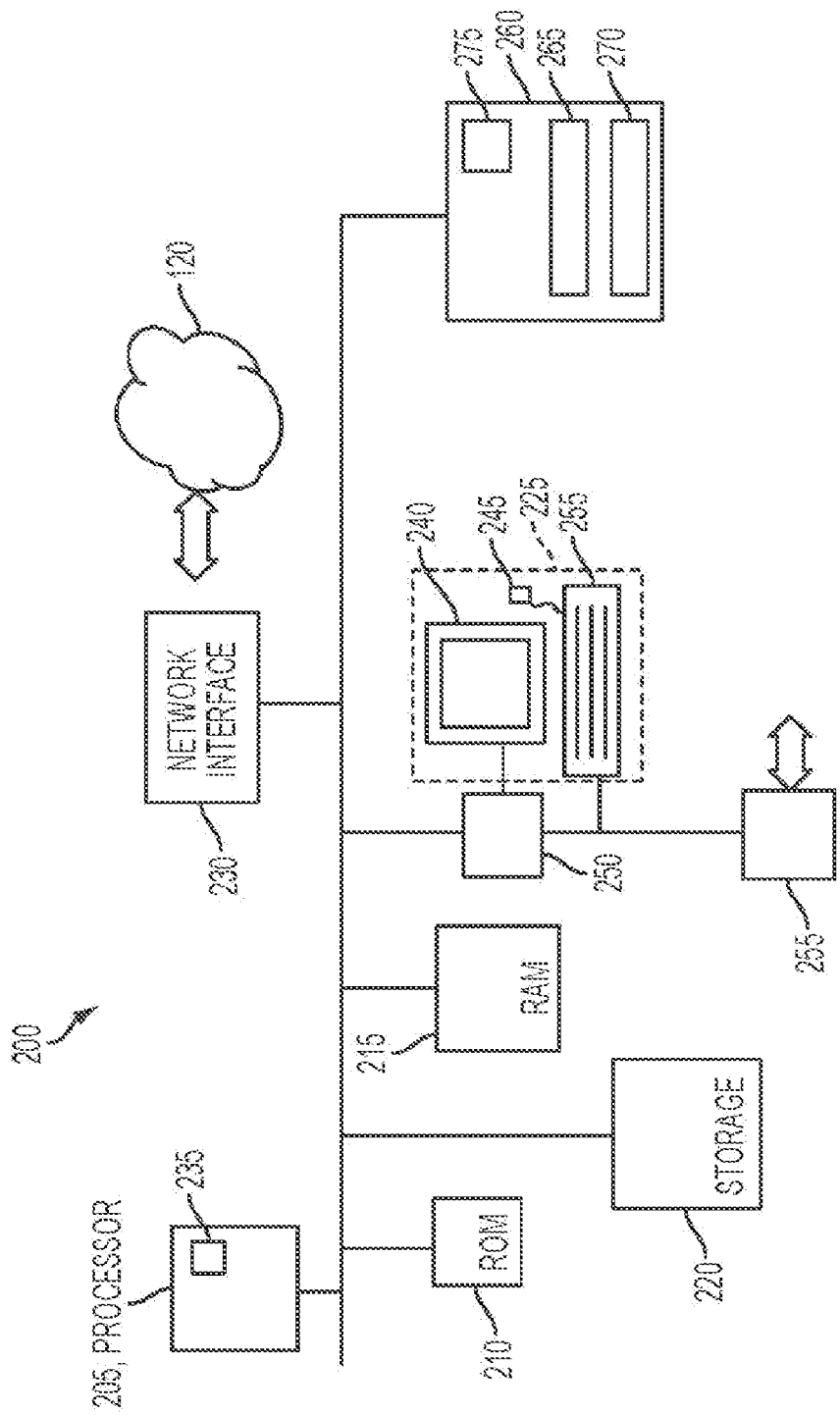
FIG. 2 shows an exemplary function controller for implementing the disclosed embodiments.

FIG. 2 shows an exemplary function controller 200 within which each of the four functions 105, 110, 115, 120 and the manager 130 may be put into practice. Each of the functions may operate in a hardware or software function controller that pre-exists within system 100. For example, each function may reside in a component controller, a controller that directs the operation of a number of components, a controller that controls a sub-system, or a system controller. Each function may also be implemented in dedicated hardware or software.

The function controller 200 may generally include a processor 205, read only memory 210, random access memory 215, program storage 220, a user interface 225, and a network interface 230.

Processor 205 may include an on board cache 235 and is generally operable to read information and programs from a computer program product, for example, a computer useable medium, such as on board cache 235, read only memory 210, random access memory 215, and program storage 220.

Upon power up, processor 205 may begin operating programs found in read only memory 210 and after initialization, may load instructions from program storage 220 to random access memory 215 and operate under control of those programs. Frequently used instructions may be temporarily stored in on board cache 235. Both read only memory 210 and random access memory 215 may utilize semiconductor technology or any other appropriate materials and techniques.

Program storage 220 may include a diskette, a computer hard drive, a compact disk (CD), a digital versatile disk (DVD), an optical disk, a chip, a semiconductor, or any other device capable of storing programs in the form of computer readable code.

On board cache 235, read only memory 210, random access memory 215, and program storage 220, either individually or in any combination may include operating system programs. The operating system programs may be supplemented with an optional real time operating system to improve the quality of data provided by the function controller 200 and to allow the function controller 200 to provide a guaranteed response time.

In particular, on board cache 235, read only memory 210, random access memory 215, and program storage 220, either individually or in any combination may include programs for causing the processor 205 to perform the data collection, pre-processing, analysis, reasoning functions, and the operation of the health-monitoring and fault-diagnostic manager described below. In addition, on board cache 235, read only memory 210, random access memory 215, and program storage 220 may be loaded with new or upgraded programs, for example, by processor 205 through network interface 230.

Network interface 230 may be generally adapted to provide an interface between the function controller 200 and other function controllers, system controllers, or other systems. Network interface 230 may operate to receive data from one or more additional function controllers and to convey data to the same or other function controllers. Network interface 230 may also provide an interface to a global diagnostic system that may provide remote monitoring and diagnostic services.

Communication network 120 may include the Public Switched Telephone Network (PSTN), the Internet, a wireless network, a wired network, a Local Area Network (LAN), a Wide Area Network (WAN), a virtual private network (VPN) etc., and may further include other types of networks including X.25, TCP/IP, ATM, etc. In one embodiment, communication network 120 may be an IEEE 1349 network, also referred to as a "Firewire" network.

The function controller 200 may include a user interface 225 with a display 240 and an input device such as a keyboard 255 or mouse 245. The user interface may be operated by a user interface controller 250 under control of processor 205 and may provide a user with a graphical user interface to visualize the results of the health monitoring and fault diagnostics. The user interface may also be used to guide service personnel through troubleshooting routines or repair processes. In addition, the user interface controller may also provide a connection or interface 255 for communicating with other function controllers, an external network, another control system, or a host computer.

Returning to FIG. 1, the data collection function 105 operates to acquire time histories of selected variables relating to the operation of a device being monitored. A time history refers to a collection of values for a particular variable or group of variables over time. In addition to the elements of the function controller 200 described above, the data collection function 105 includes one or more buffers 125 for collecting the values of the selected variables. The data collection function 105 also includes programs and circuitry 135 for specifying the device signals and variables to be recorded, setting the sampling period for data recording, setting the trigger mode for data recording (e.g., on event, on start of move, on end of move, when above threshold, when below threshold, with delay), setting the number of samples to be recorded, and setting the mechanism to stop data recording (e.g., when specified, on event, on end of move, on error, with delay).

The pre-processing function 115 determines specified characteristics of the acquired time histories. For example, a specified characteristic may include an average signal value or a maximum power consumption. Exemplary calculations performed by the pre-processing function may include simple mathematical operations such as add, subtract, multiply, divide, calculation of maximum, minimum and average values, Fourier transformation, wavelet transformation, and evaluation of various mathematical models. In addition to the elements of the function controller 200 described above, the pre-processing function 115 includes programs and circuitry 140 for receiving the time histories from the data collection function 105 and for performing the simple calculations required.

The analysis function 120 includes algorithms for analyzing the characteristics of a number of individual components, and for producing one or more hypotheses about the condition of each of the components. For example, the analysis function 120 may include various analysis algorithms 145 specifically tailored for the type of characteristics being examined, such as voltage, current, torque, signal variation, etc. As a further example, when implemented in a robotized manufacturing tool, the analysis function 120 may include algorithms for encoder signal analysis, motor PWM and current analysis, power supply voltage analysis, tracking error analysis and robot torque analysis. The algorithms may have access to and may utilize a library 150 of various analysis methods including simple threshold rules 155, fuzzy logic 160, neural networks 165, regression analysis 170, and pattern recognition techniques 175.

The reasoning function 125 derives, based on the hypotheses obtained from the analysis function 120, the final response of the system 100, including the condition of the individual components and the degree of confidence that one or more monitored devices are in good-health condition. The reasoning function 125 may include an expert diagnostic system 180 which may include, for example, a knowledge base 197 having rule-based information relating to a given set of parameters for system components and sub-systems. The expert diagnostic system 180 may utilize various methods based on, for instance, Boolean logic 185, fuzzy logic 190, or neural networks 195.

The functions of the present system 100 are coordinated by a health-monitoring and fault-diagnostic (HMFD) manager 130. The manager 130 may configure and initialize each of the data collection, pre-processing analysis, and reasoning functions to operate for a number of given monitored devices.

For example, the manager 130 may initialize the data collection function 105 with a number of variables to record, along with a number of samples to record and triggering information in order for the pre-processing function to produce one or more time histories. The manager 130 may coordinate the operations of the data collection function 105 in any of a number of collection modes, for example, data collection may take place at all times during normal operation of the device being monitored, or it may occur when the device performs certain pre-determined operations which are part of its regular operation which is convenient when comparing current signals with a normal baseline profile. Alternately, data collection may be triggered at regular intervals as the device being monitored performs a set of template operations pre-designed specifically for health-monitoring and fault-diagnostic purposes. In one embodiment, the manager may limit the amount of data recorded during data collection operations to a minimum amount for detecting deteriorating health or for diagnosing faults of the monitored device.

In some embodiments, when a potential problem is detected, the manager 130 may initiate collection of additional data by the data collection function 105 for accurate fault diagnosis. The manager 130 may also initiate a template sequence which was pre-designed specifically for health-monitoring and fault-diagnostic purposes. This sequence may be specific to a certain mode of failure or a category of modes of failure.

The manager 130 may operate to initialize the pre-processing function 110 by specifying the type of pre-processing that will occur when the time histories are sent to the pre-processing function 110. In addition, the manager 130 may preset the analysis function 115 with the types of analysis to be performed on the data for the various data characteristics received from the pre-processing function 110. The manager 130 may also pre-load the library 150 and specify the methods used in the different analyses. Furthermore, the manager 130 may trigger decision making in the reasoning function 125 when the analyses are complete.

As mentioned above, the system 100 provides at least two distinct functions: health monitoring and fault diagnostics. The purpose of health monitoring is to perform condition assessment of individual components of the robotized tool, and report a service request when a problematic condition of any of the components is identified. This information can be used for preventive maintenance, reducing material damage and unscheduled downtime due to unforeseen failures. Additionally, the present system can adjust the operation of the robotized tool to keep the tool functional to the extent possible, to reduce the effect of the progressing failure on key performance characteristics, and/or to increase the time to a fatal failure so that the tool can run till it can be serviced, e.g., till the next schedule maintenance takes place.

The purpose of fault diagnostics, on the other hand, is to complement or relieve an operator from fault classification and troubleshooting tasks, including diagnostic error codes and interactive diagnostic screens, thus improving responsiveness, quality and cost of service.

An automated material-handling platform for production of semiconductor devices will be used as an exemplary embodiment in which the present condition-monitoring and fault-diagnostic system may be practiced.

Figure 3:
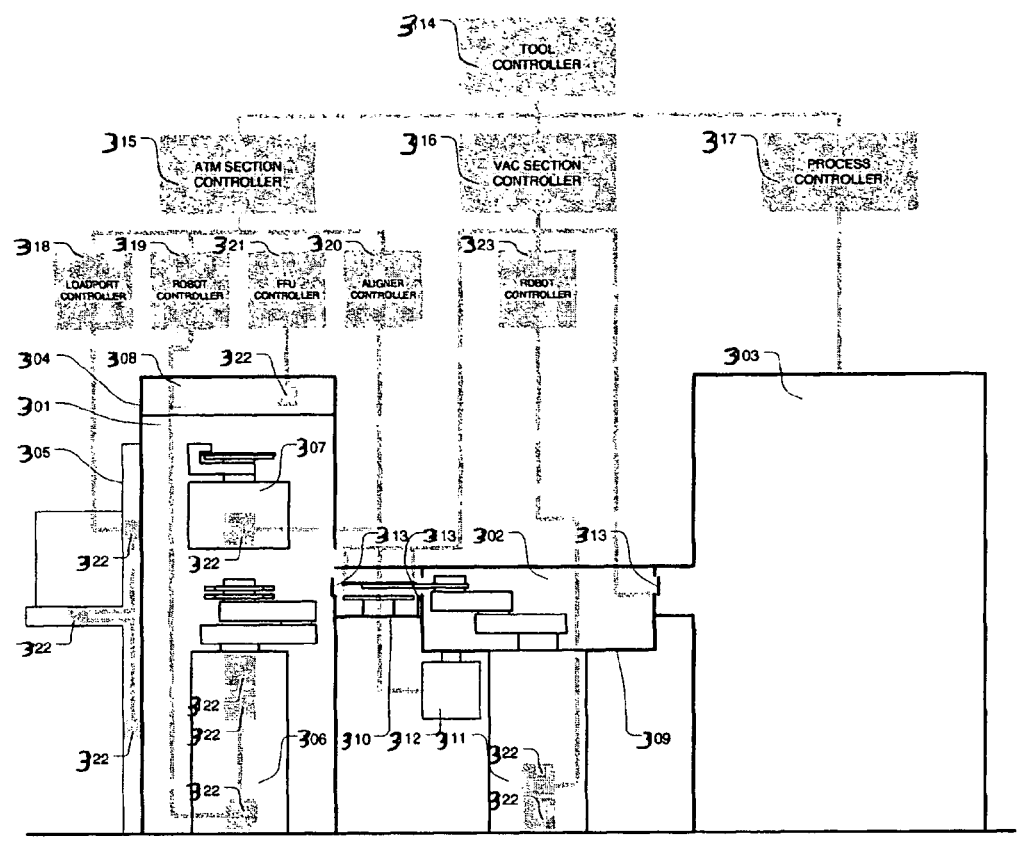
FIG. 3 shows an automated material-handling platform for production of semiconductor devices.

An exemplary material-handling platform for production of semiconductor devices is depicted diagrammatically in FIG. 3, with explanatory notes for major components being listed in Table 1.

TABLE 1

Explanatory notes for the automated material-handling platform of FIG. 3.

| Number | Description |
|---|---|
| 301 | Atmospheric section |
| 302 | Vacuum section |
| 303 | Process module |
| 304 | Enclosure |
| 305 | Loadport |
| 306 | Atmospheric robotic manipulator |
| 307 | Substrate aligner |
| 308 | Fan-filter unit |
| 309 | Vacuum chamber |
| 310 | Load-lock |
| 311 | Vacuum robotic manipulator |
| 312 | Vacuum pump |
| 313 | Slit valve |
| 314 | Tool controller |
| 315 | Atmospheric section controller |
| 316 | Vacuum section controller |

TABLE 1-continued

Explanatory notes for the automated material-handling platform of FIG. 3.

| Number | Description |
|---|---|
| 317 | Process controller |
| 318 | Loadport controller |
| 319 | Atmospheric robot controller |
| 320 | Aligner controller |
| 321 | Fan-filter unit controller |
| 322 | Motor controller |
| 323 | Vacuum robot controller |

The platform has an atmospheric section 301, vacuum section 302 and one or multiple process modules 303.

The atmospheric section 301 may include an enclosure 304, one or multiple loadports 305, one or multiple robotic manipulators 306, one or multiple substrate aligners 307 and a fan-filter unit 308. It may also include one or more ionization units (not shown). The vacuum section may include a vacuum chamber 309, one or multiple load-locks 310, one or multiple robotic manipulators 311, one or multiple vacuum pumps 312 and a plurality of slit valves 313, which are typically located at the interface of the atmospheric section 301 with the load-locks 310, between the load-locks 310 and the vacuum chamber 309, and between the vacuum chamber 309 and the process module 303.

The operation of the platform is coordinated by the tool controller 314, which supervises the atmospheric section controller 315, vacuum section controller 316 and one or multiple process controllers 317. The atmospheric section controller 315 is in charge of one or multiple loadport controllers 318, one or multiple atmospheric robot controllers 319, one or multiple aligner controllers 320 and a fan-filter unit controller 321. Each of the loadport controllers 318, atmospheric robot controllers 319 and aligner controllers 320 is in turn in charge of one or multiple motor controllers 322. The vacuum section controller 316 is in charge of one or multiple vacuum robot controllers 323, controls the vacuum pump 312 and operates the slit valves 313. The role of the process controller 317 depends on the operations performed in the process modules 303.

In some cases, it may be practical to combine two or more layers of control into a single controller. For instance, the atmospheric robot controller 119 and the corresponding motor controllers 122 may be combined in a single centralized robot controller, or the atmospheric section controller 115 can be combined with the atmospheric robot controller 119 to eliminate the need for two separate controller units.

A five-axis direct-drive robotic manipulator may be employed in the platform of FIG. 3. A simplified schematic of such a robotic manipulator is provided in FIG. 4. Explanatory notes for major components are listed in Table 2.

TABLE 2

Figure 4:
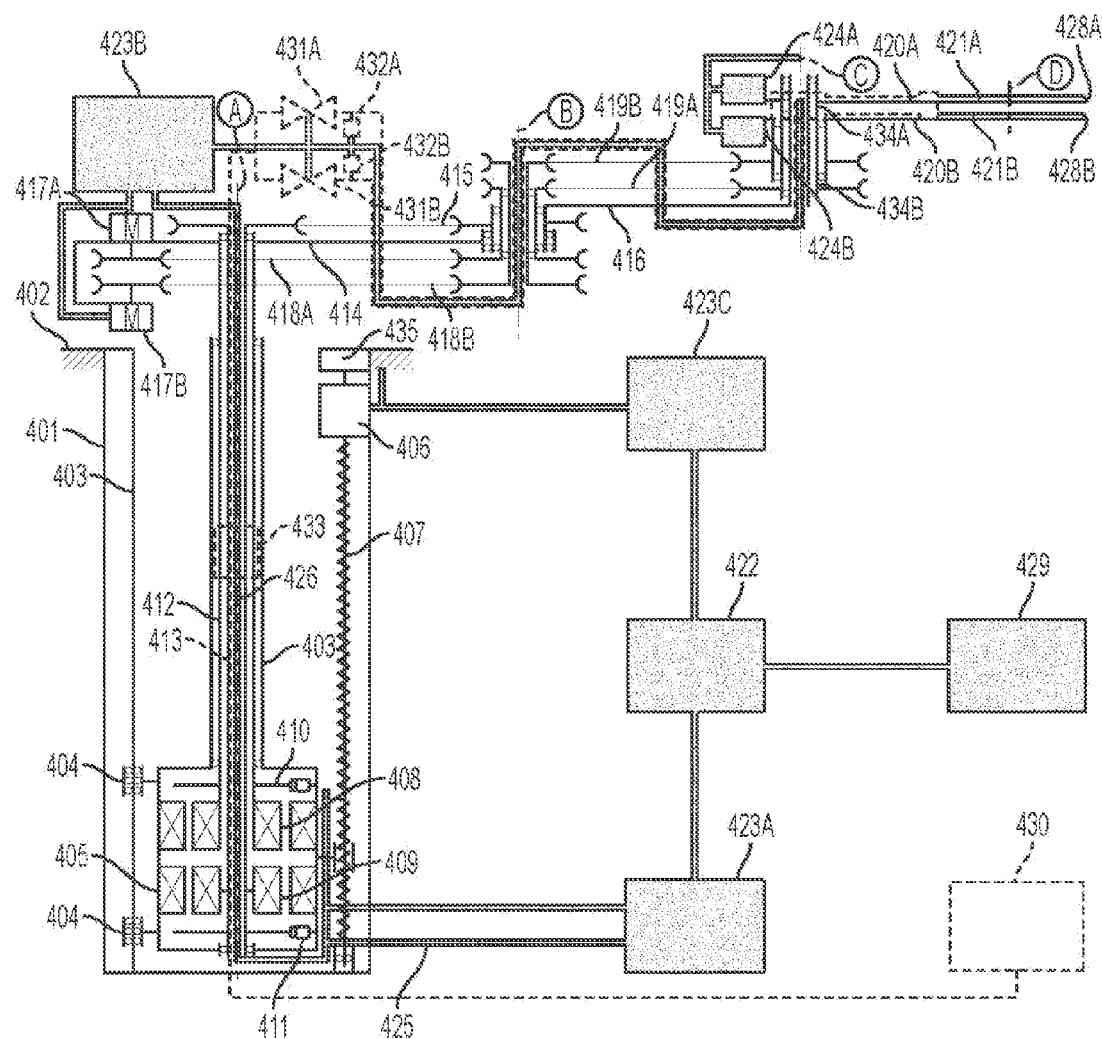
FIG. 4 shows a five-axis direct-drive robotic manipulator.

Explanatory notes for robotic manipulator of FIG. 4.

| Number | Description |
|---|---|
| 401 | Robot frame |
| 402 | Mounting flange |
| 403 | Vertical rail |
| 404 | Linear bearing |
| 405 | Carriage |
| 406 | Vertical drive motor |

TABLE 2-continued

Explanatory notes for robotic manipulator of FIG. 4.

| Number | Description |
| --- | --- |
| 407 | Ball screw |
| 408 | Motor 1 (driving link 1) |
| 409 | Motor 2 (driving link 2) |
| 410 | Encoder 1 (coupled to motor 1) |
| 411 | Encoder 2 (coupled to motor 2) |
| 412 | Outer shaft |
| 413 | Inner shaft |
| 414 | Link 1 (upper arm) |
| 415 | Belt driving link 2 |
| 416 | Link 2 (forearm) |
| 417A | Motor A (driving end-effector A) |
| 417B | Motor B (driving end-effector B) |
| 418A | First stage of belt drive A |
| 418B | First stage of belt drive B |
| 419A | Second stage of belt drive A |
| 419B | Second stage of belt drive B |
| 420A | End-effector A (upper end-effector) |
| 420B | End-effector B (lower end-effector) |
| 421A, 421B | Payload on end-effectors A and B |
| 422 | Master controller |
| 423A, 423B, 423C | Motor controllers |
| 424A, 424B | Electronic units for end-effectors A and B |
| 425 | Communications network |
| 426 | Slip-ring |
| 428A, 428B | Mapper sensors |
| 429 | Power supply |
| 430 | Vacuum pump |
| 431A, 431B | Valves |
| 432A, 432B | Pressure sensors |
| 433, 434A, 434B | Lip-seals |
| 435 | Brake |

Referring to FIG. 4, the robotic manipulator is built around an open cylindrical frame 401 suspended from a circular mounting flange 402. The frame 401 incorporates a vertical rail 403 with linear bearing 404 to provide guidance to a carriage 405 driven by a brushless DC motor 406 via a ball-screw mechanism 407. The carriage 405 houses a pair of coaxial brushless DC motors 408, 409 equipped with optical encoders 410, 411. The upper motor 408 drives a hollow outer shaft 412 connected to the first link 414 of the robot arm. The lower motor 409 is connected to a coaxial inner shaft 413 which is coupled via a belt drive 415 to the second link 416. The first link 414 houses a brushless DC motor 417A which drives through a two-stage belt arrangement 418A, 419A the upper end-effector 420A. Another DC brushless motor 417B and a two-stage belt drive 418B, 419B are employed to actuate the lower end-effector 420B. Each of the stages 418A, 418B, 419A and 419B are designed with a 1:2 ratio between the input and output pulleys. Substrates 421A and 421B are held attached to end-effectors 420A and 420B, respectively, by the means of vacuum-actuated edge-contact grippers or surface-contact suction grippers. See FIGS. 5 and 6 for exemplary gripper designs.

The first link 414, second link 416, upper end-effector 420A and lower end-effector 420B are also referred to as the upper arm, forearm, end-effector A and end-effector B, respectively, throughout the text. The points A, B and C indicate revolute couplings which are referred to as the shoulder, elbow and wrist joints, respectively. Point D denotes a reference point which indicates the desired location of the center of the substrate on the corresponding end-effector.

The control system of the example robotic manipulator may be a distributed type. It comprises a power supply 429, master controller 422 and motor controllers 423A, 423B and 423C. The master controller 422 is responsible for supervisory tasks and trajectory planning. Each of the motor controllers 423A, 423B and 423C execute the position and current feedback loops for one or two motors. In FIG. 4, the controller 423A controls motors 408 and 409, the controller 423B controls motors 417A and 417B and the controller 423C controls motor 406. In addition to executing the feedback loops, the motor controllers also collect data such as motor current, motor position and motor velocity, and stream the data to the master controller. The motor controllers 423A, 423B and 423C are connected to the master controller through a high-speed communication network 425. Since the joint A is an infinite rotation joint, the communication network 425 is routed through a slip-ring 426. Additional electronic units 424A and 424B may be used to support the edge-contact grippers of the end-effectors 420A and 420B, respectively.

Figure 5:
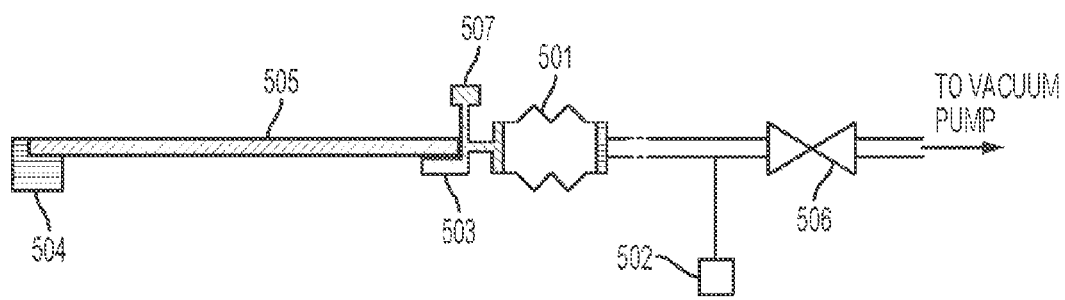
FIG. 5 shows a vacuum-actuated edge-contact gripper.

FIG. 5 shows a schematic of a vacuum-actuated edge-contact gripper system. It includes a bellows 501 attached to a vacuum line on one end and a plunger 503 attached to the other end. In the absence of vacuum, the spring loaded plunger pushes the substrate 505 against the stationary stops 504 and holds it in place. In the presence of vacuum, the plunger is retracted, which releases its hold on the substrate. The position of the flag 507 is used to determine the position of the plunger which, in turn, indicates one of the following three states: unclamped (plunger 503 retracted), properly clamped (plunger 503 partially extended) and clamping failure (plunger 503 fully extended). The gripper is operated by opening and closing a vacuum valve, such as 431A or 431B in FIG. 4. The vacuum pressure may be measured by a pressure sensor, such as 432A or 432B in FIG. 4.

Figure 6:
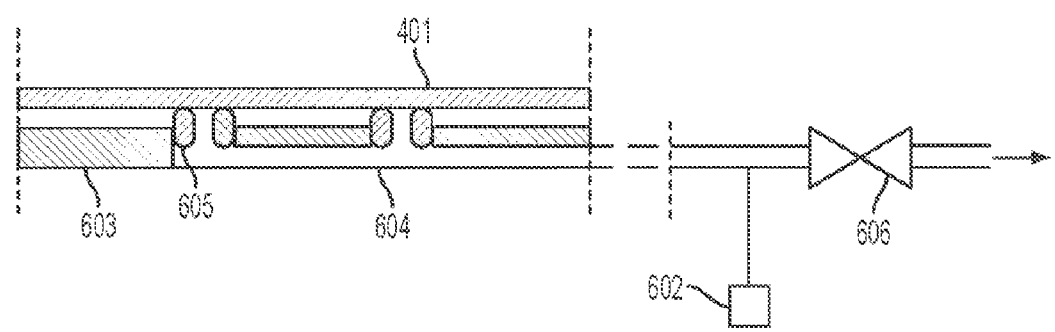
FIG. 6 shows a surface-contact suction gripper.

FIG. 6 shows a cross-sectional view of a surface-contact suction gripper. The robot end-effector 603 has two or more orifices 605 that are connected to a vacuum line 604. In the presence of vacuum, the substrate 601 is pulled toward the end-effector 403 and held in place by the means of friction. The gripper action is initiated by a vacuum valve, such as 431A or 431B in FIG. 4. The presence or absence of the substrate 601 on the end-effector 603 can be determined by a pressure sensor, such as 432A or 432B in FIG. 4. The pressure sensor 432A or 432B detects a vacuum if the substrate 601 is present.

As indicated above, both types of grippers require a vacuum valve, such as valves 431A and 431B in FIG. 4, that opens or closes the vacuum line. The vacuum valves may be controlled either by the master or motor controllers 422, 423A-C. In addition, the vacuum system may also come equipped with pressure sensors, such as sensors 432A and 432B, that are used to determine the vacuum level in the vacuum system.

The use of vacuum for the vacuum-actuated edge-contact gripper or surface-contact suction gripper requires a vacuum line to be run through the joints, connecting an external vacuum source, such as a vacuum pump, to the end effector. Since joints A and C are continuous rotation joint, lip seals 433, 434A and 434B are used to transmit vacuum across the joints A and C.

In some cases, each of the robot end-effectors 420A, 420B may be equipped with a substrate presence sensor. This sensor may either complement the substrate presence sensing methods described above for the vacuum-actuated edge-contact gripper of FIG. 5 and the surface-contact suction gripper of FIG. 6, or can serve as the only means of substrate presence sensing, such as when the substrate is held on the end-effector passively, e.g., by frictional forces between the substrate and the end-effector.

Figure 7:
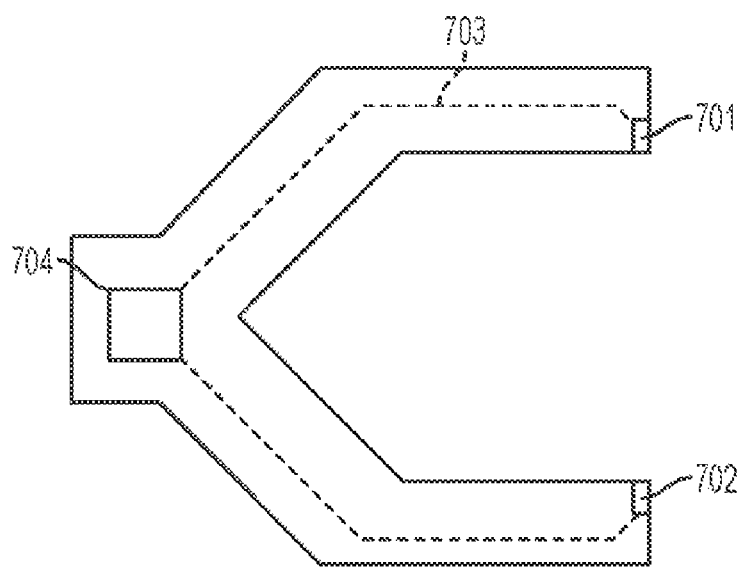
FIG. 7 shows an end-effector with one or more mapper sensors.

Each of the end-effectors 420A, 420B may also be equipped with a substrate mapper sensor, such as 428A and 428B in FIG. 4. Each mapper sensor comprises a light emitter 701 and a light receiver 702 as shown in FIG. 7. As the robot scans a substrate carrier, the binary output of the light detector changes state and is read by the controller which determines the presence or absence of a wafer in each of the slots in the substrate carrier. The controller also records robot axes positions each time the binary output changes state and uses this information to detect "cross-slotted" wafers and "doubly-placed" wafers in the load port.

The motor that controls the vertical motion of the robot (motor 406 in FIG. 4) is equipped with a solenoid actuated brake 435. In the absence of motor torque, the brake engages in order to prevent a free fall of the robot. The vertical axis may also be equipped with over-travel sensors, such as limit switched, that detect when the carriage 405 exceeds the allowable range of vertical motion.

The robotic manipulator may include additional components, such as cooling fans to remove heat generate by motors and electronics. In some applications, the robotic manipulator may be installed on a horizontal traverser.

Since optical encoders, such as 410 and 411 in FIG. 4, are critical for proper operation of the robot and represent a valuable source of information for health monitoring and fault diagnostics, more detailed description of their functionality should be provided. A rotary optical encoder is a device that converts angular motion into a digital output easily interfaced with the controller. There are two types of optical encoders: incremental and absolute.

Figure 8:
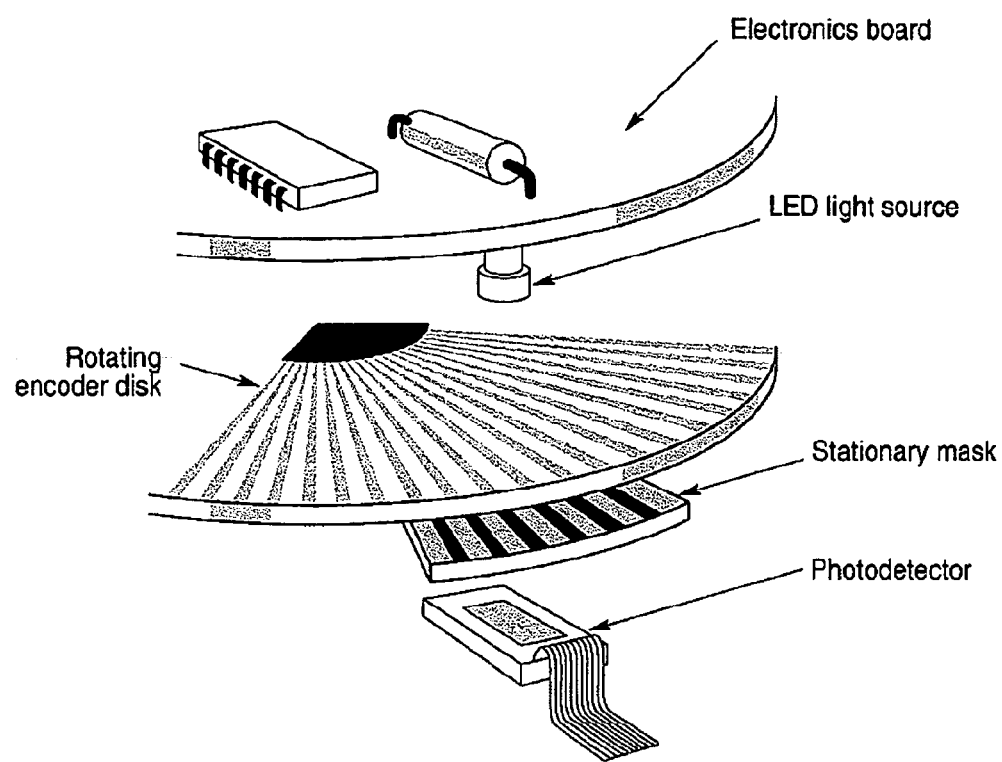
FIG. 8 shows an incremental rotary optical encoder.

A rotary incremental optical encoder (FIG. 8) may have the following components: light source, rotating encoder disk, stationary mask, photodetector, and electronics to amplify and square the output signals from the photodetector. As the encoder disk rotates in front of the mask, it shutters the light from the light source. The light that passes through mask is received by the photodetector which produces pulses in the form of a quasi-sine wave output. The encoder electronics convert this output into a square wave form, ready for transmission to a counter. The number of counts is directly proportional to the angular position of the encoder disk. Many encoders also include a single zero mark which provides one pulse every mechanical rotation for reference, e.g., to determine a home position.

Figure 9:
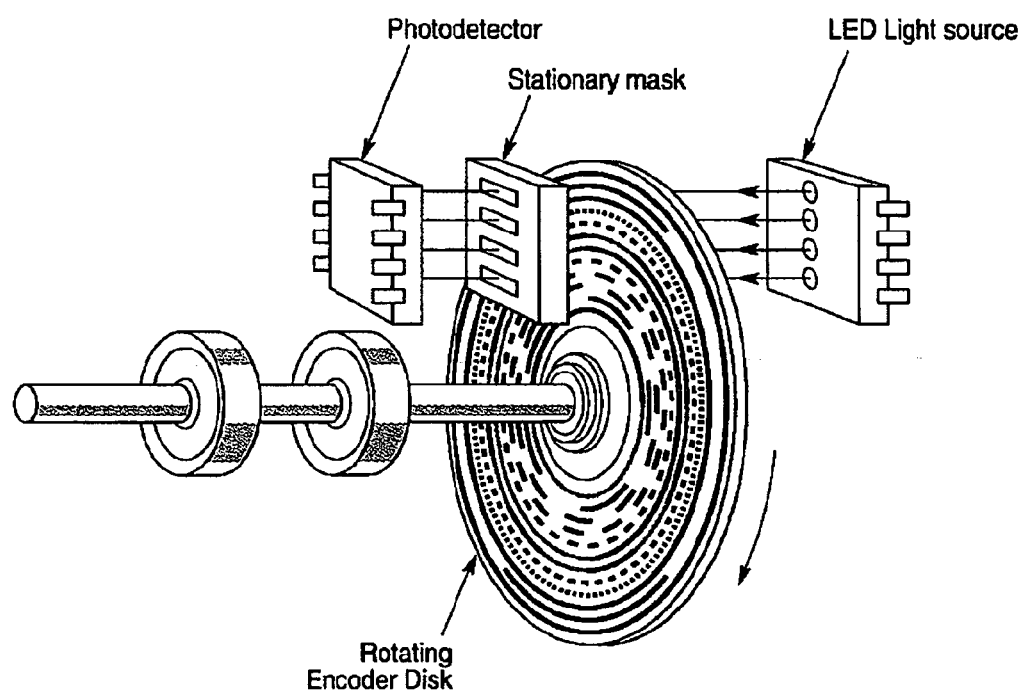
FIG. 9 shows an absolute rotary optical encoder.

In principle, rotary absolute optical encoders (FIG. 9) are similar to incremental encoders in that a rotating disk interrupts light between a source and photodetector to produce an output signal. However, as opposed to a single track incremental encoder, an absolute encoder disk features several concentric tracks, each having a pattern of transparent and opaque segments. These independent tracks provide a unique combination for each resolvable position. Since every position of an absolute encoder is unique, absolute encoders do not loose position when power is removed, and it is not necessary to initialize the system by returning to a zero or home position. In most applications, the absolute position is determined only when the device is turned on. From that point on, to make it possible to obtain high resolution at fast speeds, the position is determined in an incremental manner based on analog sin/cos signals.

The example robotic manipulator is a complex mechatronic system with numerous components that may exhibit failures. These components include the power supply, motors, encoders, belts, bearings, ball-screws, brakes, vacuum system components, communication system components, master controller, motor controllers, and cooling fans.

The present condition-monitoring and fault-diagnostic system utilizes time histories of selected signals to perform condition assessment of individual system components. The signals may be obtained from sources that already exist in the tool, or may come from additional sensors added specifically for health-monitoring and fault-diagnostic purposes.

Generally, it is desirable to extract as much information as possible from the sources that already exist in the tool, i.e., those sources that are used by the robot and other devices to achieve the desired functionality. This is because additional sensors lead to increased complexity and cost. In some cases, however, it may be preferable to add sensors specifically for health-monitoring and fault-diagnostic purposes because extracting all of the information from the existing signals is not possible or requires complex algorithms, which need to run on more powerful and expensive processors, and may be costly to develop and support.

Existing Measurable Signals

Typically, the following signals exist in a robotized manufacturing tool, and can be made available for condition monitoring and fault diagnostics:

(a) Motor PWM duty: PWM duty of a motor is the percentage of input voltage that is supplied to each motor phase at any given time. The duty cycle at each of the motor phases is available to the health-monitoring and fault-diagnostic system.

(b) Motor current: Motor current represents the current flowing through each of the three phases of each of the motors. The motor current may be obtained as an absolute value or as a percentage of the maximum current. If obtained as an absolute value it has units of Amps. Motor current values can in turn be used to compute motor torques using the motor torque-current relationships.

(c) Actual position, velocity and acceleration: These are the position, velocity and acceleration of each of the motor axes. For rotational axes, the position, velocity and acceleration values are in units of degrees, degrees/sec and degress/sq.sec respectively. For translational axes, the position, velocity and acceleration values are in units of mm, mm/sec and mm/sq.sec respectively.

(d) Desired position, velocity and acceleration: These are the position, velocity and acceleration values that the controller commands the motors to have. These properties have similar units as the actual position, velocity and acceleration above.

(e) Position and velocity tracking error: These are the differences between the respective desired and actual values. These properties have similar units as the actual position, velocity and acceleration above.

(f) Settling time: This is the time it takes for the position and velocity tracking errors to settle within specified windows at the end of motion.

(g) Encoder analog and absolute position outputs: The motor position is determined by the encoders which output two types of signals—analog signals and absolute position signals. Analog signals are sine and cosine signals in units of mVolts. Absolute position signals are non-volatile integer values that indicate the number of analog sine cycles or an integer multiple of analog sine cycles that have gone by. Typically, digital outputs are read on power up and thereafter the axis position is determined solely from the analog signals.

(h) Gripper state: This is the state of the gripper—open or closed. In the case of a vacuum-actuated edge-contact gripper, it is the blocked/unblocked state of one or more sensors.

(i) Vacuum system pressure: This is the vacuum level measured by a vacuum sensor. This is an analog sensor whose output is digitized by an analog-to-digital converter. In the case of a suction gripper, the vacuum level indicates whether the wafer has been gripped.

(j) Substrate-presence sensor state: In a passive grip end effector, the wafer presence sensor output is a binary output. In a vacuum-actuated edge-contact grip end effector, the wafer presence is determined from the output state of two or more sensors each of which is binary.

(k) Mapper sensor state: This is the state of the mapper sensor—blocked or unblocked at any given instance.

(l) Mapper/Aligner detector light intensity: This is a measure of the intensity of the light detected by the light detector (503 in FIG. 5). This signal is typically available as an integer value (that may have a range of 0-1024 as an example).

(m) Mapper sensor position capture data: This is the array of robot axis position values at which the mapper sensor changes state.

(n) Vacuum valve state: This is the commanded state of the vacuum valve. It specifies if the solenoid that operates the vacuum valve is supposed to be energized.

(o) Voltage at fuse output terminals: The voltages at the output terminals of each of the fuses in the motor control circuitry is monitored. A blown fuse results in low output terminal voltage.

(p) Substrate alignment data: These are the substrate eccentricity vector and angular orientation of the alignment fiducial of a substrate reported by the aligner.

(q) Position data at transition of external substrate sensors: In some cases, the atmospheric and vacuum sections of the tool may be equipped with optical sensors which detect the leading and trailing edges of a substrate carried by the robot. The robot position data corresponding to these events are used for on-the-fly recognition of the eccentricity of the substrate on the robot end-effector.

(r) Substrate cycle time: This is the time it takes for a single substrate to be processed by the tool, typically measured under steady flow conditions.

(s) Mini-environment pressure: This is the pressure measured by a pressure sensor in the atmospheric section of the tool.

Additional Sensors for HMFD

As mentioned above, it is often desirable to complement the signals that are already available in the tool by sources of information added specifically for the purpose of health monitoring and fault diagnostics. These sources may include the following:

(a) Direct Measurement of Motor torque: Motor torques can be measured directly instead of being estimated from motor current. This is done by using force or torque gauges to measure the external force/torque required to hold an energized motor stationary.

(b) Motor temperature: This refers to the temperature of the motor and is read by a temperature sensor that is mounted on the motor. Temperature may be available in units of degree C.

(c) Over-travel sensors: These are sensors, such as limit switches, that indicate if the motion axis that the sensors are associated with exceeded its allowable range of travel.

(d) Acoustic and vibration sensor data: This represents electrical signals obtained from microphones and accelerometers placed at various points on the robot or in the vicinity of the robot.

(e) Infrared sensor data: This represents temperature readings obtained from infrared sensors placed at various points in the tool to monitor temperature variation.

(f) Power consumption: The motor currents, velocities and duty cycle values can be used to compute the electrical power consumed by each motor at any given time.

(g) Deflection: This represents electrical signals obtained from strain-gauges placed at various points on the robot to measure deflection.

(h) Belt tension: The output of a force sensing device attached to the belt tensioner serves as a measure of belt tension. It has units of Newtons.

(i) Duration of operation of cooling fans: Cooling fans may either be continuously operating or thermostat controlled. A useful indicator of heat dissipation from the robot is the duration of operation of thermostat controlled cooling fans.

(j) Electrostatic charge of substrate: Among other methods, the level of the substrate charge can be determined through a controlled discharge of the substrate.

(k) Position data at transition of external sensors: Additional external sensors may be used to detect edges of moving substrates and robot components to allow the controller to capture the corresponding robot position data and use the resulting information, e.g., for robot and substrate repeatability checking.

(l) Video images: These represent video images obtained from video cameras mounted either stationary at specific locations that the robot reaches periodically, or cameras carried by the robot. In the latter case, the cameras may point either at the end-effector or at stationary markers.

(m) Plenum pressure: This is the pressure measured by a pressure sensor on the input side of the filter in the fan-filter unit.

EXAMPLE MODES OF FAILURE

Component failures can be categorized broadly into two different types—"chronic" faults that develop gradually and "acute" faults that occur instantly. Faults of the first kind can be detected by a condition monitoring system at their early stages of development. Early detection and repair will help avoid unexpected failure during operation. On the other hand, faults of the second type do not lend themselves to early detection. However, a fault diagnostics system can help diagnose them when they occur and therefore shorten the time to bring the machinery back into operation. The different types of faults that can occur are listed below and summarized in Table 3.

TABLE 3

Example modes of failure and their symptoms

| Component | Mode of failure | Sudden/ gradual | Measurable symptom |
| --- | --- | --- | --- |
| Motor | Weakening or disintegration of magnets | Gradual | Overall increase in motor winding currents; Overall increase in motor temperature; Increase in power consumption; |

TABLE 3-continued

Example modes of failure and their symptoms

| Component | Mode of failure | Sudden/ gradual | Measurable symptom |
|---|---|---|---|
| | Slipping or misalignment of stator | Gradual | Increase in energy dissipation; Longer duration of operation of cooling fans Increase in motor winding currents; Overall increase in motor temperature; Increase in power consumption; Increase in energy dissipation; Longer duration of operation of cooling fans |
| | High connector resistance | Gradual | Overall increase in PWM duty; Overall increase in power consumption; Increase in energy dissipation |
| | Burnt Motor Phase | Abrupt | Abrupt drop in motor current in the phase winding |
| | Blown fuse | Abrupt | Abrupt drop in voltage at the output terminal of the fuse |
| Encoder | Optical disk contamination | Gradual | Attenuation of sine signal amplitude |
| | Read-head misalignment | Gradual or abrupt | Phase distortion of sin/cos signals; Attenuation of signal amplitude |
| | Electrical noise in encoder wiring | Gradual or abrupt | Decrease in signal-to-noise ratio of sin/cos signals |
| | Missed counts | Gradual or abrupt | Differences between absolute axis position and position computed from incrementing encoder counts |
| Belt | Tension below specification | Gradual | Oscillatory tracking errors; Lower force measurement at the belt tensioner; Decrease in resonance frequency corresponding to belt tension |
| | Tension above specification | Abrupt | Higher force measurement at the belt tensioner Increase in resonance frequency |
| | Rubbing against a component | Gradual or abrupt | Higher motor currents; Higher power consumption; Higher energy dissipation; Increase in motor temperature; Longer duration of operation of cooling fans; Shifts in power spectrum of acoustic energy dissipation |
| | Belts slipping | Gradual or abrupt | Significant shift in position measured by external sensors such as video cameras and over-travel sensors; Increase in tracking errors. |
| Vacuum system | Leak | Gradual or abrupt | Lower vacuum pressure measurement; Increase in pressure transition time. This results in an increase in grip actuation time in the case of a surface contact vacuum gripper and an increase in grip release time in the case of a vacuum actuated edge contact gripper; Failure to grip, in the case of a surface contact vacuum gripper and a failure to ungrip in the case of a vacuum operated edge contact gripper |
| | Obstruction between vacuum sensor and actuator | Gradual or sudden | Decrease in pressure transition time; Increase in vacuum pressure required to accomplish a grip actuation in the case of a surface contact vacuum gripper and a grip release in the case of a vacuum actuated edge contact gripper Failure to grip, in the case of a surface contact vacuum gripper and a failure to ungrip in the case of a vacuum operated edge contact gripper |
| | Obstruction between vacuum valve and vacuum sensor | Gradual or sudden | Low vacuum pressure detected by the vacuum sensor; Increase in pressure transition time. This results in an increase in grip actuation time in the case of a surface contact vacuum gripper and an increase in grip release time in the case of a vacuum actuated edge contact gripper; Failure to grip, in the case of a surface contact vacuum gripper and a failure to ungrip in the case of a vacuum operated edge contact gripper |
| Vacuum-actuated edge-contact gripper | Jammed Plunger | Gradual or abrupt | Increase in vacuum pressure for grip actuation; Failure to release grip |
| | Broken spring | Abrupt | Gripper is always in released state |
| Bearing/ball-screw | Binding | Gradual | Increase in motor current; Increase in power consumption; Increase in energy dissipation; Increase in tracking error; Increase in motor temperature |
| | Play | Gradual | Higher position errors recorded by external position sensors such as over-travel sensors and |

TABLE 3-continued

Example modes of failure and their symptoms

| Component | Mode of failure | Sudden/ gradual | Measurable symptom |
|---|---|---|---|
| | | | video imaging cameras; If large enough to cause noticeable motor stator misalignment: [???] Increase in motor winding currents; Overall increase in motor temperature; Increase in power consumption; Increase in energy dissipation; Longer duration of operation of cooling fans; |
| Communication system | Slip ring failure | Gradual | Increase in error rates in the initial stages of failure; Master controller does not receive status updates from one or more motor controllers in the final stages |
| | Failure of communication chips on the motor controllers | Abrupt | Master controller does not receive status updates from one or more motor controllers |
| | Failure of communication chips on the master controller | Abrupt | The motor controllers do not receive motion information from the master controller. |
| | Break in communication link between two adjacent motor controllers | Abrupt | Decrease in the number of nodes in the network |
| Substrate mapper | Noise in sensor electrical output | Gradual | Multiple block/unblock transitions of the mapper digital output as it passes through each substrate; Odd number of state transitions |
| | Light intensity fluctuation | Gradual | Shift or absence of block/unblock transitions |
| | Faulty sensor | Abrupt | Absence of block/unblock transitions |
| Brakes | Brake partially released or not released | Gradual | Position dependent increase in motor current; Overall increase in power consumption; Increase in energy dissipation; Change in spectrum of the measured acoustic signal |
| | | Abrupt | Increase in motor current; Overall increase in power consumption; Increase in energy dissipation; Change in spectrum of the measured acoustic signal |
| External | Obstruction | Abrupt | Rapid increase in motor current; Rapid increase in position and velocity error |
| Cooling fans | Stop functioning | Abrupt | Increase in overall system temperature |
| Power supply | No voltage (e.g., blown fuse) | Abrupt | Zero motor current; Voltage sensor in motor controller indicates low bus voltage error; Sudden increase in tracking error |
| | Voltage below specification | Abrupt | For small changes: higher than normal duty cycle; no accompanying change in current; For large changes: voltage sensors in the motor controllers indicate "bus under voltage" fault. |
| | Voltage above specification | Abrupt | For small changes: lower than normal duty cycle; no accompanying change in current; For large changes: voltage sensors in motor controllers indicate "bus over voltage" fault |
| Active Gripper | Broken spring | Abrupt | Gripper is always in open position |
| | Jammed plunger | Gradual | Slow grip and ungrip actions; |
| Robot | Repeatability deterioration | Gradual | Variation in position data captured when robot end-effector detected by external sensors; Video images of robot end-effector commanded repeatedly to given position |
| | Mispick or misplace | Abrupt | Video images showing pick and place operations |
| Aligner | Fluctuation in light intensity | Gradual | Variation (reduction) of edge sensor output when fully exposed |
| Fan-filter unit | Clogged filter | Gradual | Increased in plenum pressure in order to maintain the same mini-environment pressure |
| Ionizer | Electrode deterioration | Gradual | Increase in substrate electrostatic charge |
| Tool level failures | Substrate repeatability deterioration | Gradual | Variation in position data captured when substrate edges detected by external sensors; Video images of substrates delivered to given location |
| | Robot-station misalignment | Gradual or abrupt | Variation of auto-teach and/or auto-level results |
| | Throughput reduction | Gradual or abrupt | Increase in substrate cycle time |

Robot and Aligner

Motor Faults

Motors are core components of a robot and can fail in one of many ways that result in sub-optimal operation. The following are some of the gradually developing modes of failure that can be predicted as they develop.

(a) Weakening of permanent magnets: Weakening of permanent magnets (e.g., due to magnet material disintegration in an aggressive environment) results in a loss of magnetic field strength which in turn results in lower torque output for a given current. Higher winding currents are required to maintain the same torque output. The higher current results in higher resistive energy loss which in turn results in an increase in overall power consumption and an increase in motor temperature.

(b) Slipping/misalignment of stator and incorrect phase angle: Loosening of clamps that hold the stator in place can result in slipping and misalignment of the stator. This changes the effective motor phase angle which results in incorrect commutation. Incorrect motor phase angle my also result from incorrect implementation of the phase angle estimation procedure. The symptoms are similar to those for weakening magnets above, namely, higher winding currents, motor temperature and power dissipation.

(c) High connector resistance: Contamination and/or corrosion of motor connector leads results in higher effective winding resistance. This results in an overall increase in duty cycle and total power dissipation and motor temperature.

The following motor faults may occur abruptly:

(a) Burnt motor phase: An example of an abruptly occurring motor fault is a burnt motor phase. This fault is normally flagged by the motor controller that detects an abrupt drop in current in the affected phase only.

(b) Blown fuse: A blown fuse cuts off power supply to the motor amplifier and, consequently, to all of the motor phases. A blown fuse results in an abrupt drop in voltage at the output terminal of the fuse.

Encoder Faults

Encoder faults may result in erroneous position readings. They may include the following types.

(a) Optical disk contamination: Contamination due to accumulation of dust or migration of bearing grease on the encoder disk or the read head can result in attenuation of the analog sine signal output from the encoder. This is a gradually occurring fault and can be predicted by monitoring the amplitude of the encoder sine signals. The extent of signal attenuation varies as a function of encoder position.

(b) Read-head misalignment: The two sine/cosine signals from the encoder are normally 90 degrees out of phase. However, a misaligned read head results in a change in phase difference between the two signals in addition to an attenuation of the signals. Thus this fault can be detected by monitoring the phase difference between the signals. This fault can occur gradually or suddenly.

(c) Electrical noise: Electrical noise in the signals results in lower signal to noise ratio in the analog signal from the encoder. This fault can occur intermittently in response to external events or due to a harness malfunction, and can be detected by monitoring the signal to noise ratio of the encoder analog signal.

(d) Missed encoder counts: Typically, the absolute position is read from the encoder on power up and thereafter only line count and analog signals are used to determine axis position. Periodically, the axis position derived from the line count, and possibly the analog signals, may be checked against the encoder absolute position. Missed encoder counts are indicated by a difference between the axis position and the absolute position (both read at the same time instant).

Drive Belt Faults

Timing belts serve as power transmission devices and can fail in the following ways.

(a) Incorrect belt tension: Because of stretching, the belt tension can gradually decrease. Lower belt tensions can result in a gradual destabilization of the position servo loop. This manifests itself in increasingly oscillatory position and velocity tracking errors as well as reduced stability margin. An over adjustment of the belt tensioner can also result in a higher than normal belt tension. Higher/lower belt tension also results in an increase/decrease in the force measured by force sensors mounted on the belt tensioners. A change in belt tension also results in a change in the frequency spectrum of the acoustic and structural vibration signals measured at points close to the belt. In addition, a change in belt tension can be detected through a change in the frequency response of the mechanism.

(b) Belts rubbing against a component: Incorrect belt assembly or belt walking due to a mechanical problem can result in belts rubbing against a neighboring component. Excessive belt rubbing results in an increase in friction, power consumption, current consumption, heat dissipation and motor temperature.

(c) Belts slipping: Belts can slip against the timing gear and this slipping can occur suddenly as a result of a collision. A slipped belt results in an increase in tracking errors and also result in a significant shift in the external position sensor readings. One example of an external position sensor is an externally mounted video camera. Slipped belt can also manifest itself as inconsistent readings between redundant position sensors (such as encoders) at robot joints and primary position sensors (encoders) connected to the motors.

Vacuum System Faults

Vacuum pressure is used to grasp wafers. There are two types of vacuum based wafer grippers, namely, the surface-contact suction gripper in FIG. 6 and the edge-contact vacuum actuated gripper in FIG. 5. Exemplary faults that may occur in a vacuum system include the following.

(a) Vacuum leak: Vacuum leaks can occur due to wear and tear on the lip seals. A leak in the vacuum line results in a lower vacuum pressure (when vacuum valve is open and, in case of surface-contact suction gripper, substrate is present on the end-effector), and can be detected through a drop in the vacuum sensor (302, 402) reading. In addition, a gripping action results in either no gripping or an increase in the gripper operation time. For the vacuum-actuated edge-contact gripper, the grip operation time is measured between the instant when the valve (306, 406) is commanded to open and the time a position sensing flag (308) detects open state of the gripper. For surface-contact suction gripper, the grip operation time is measured between the instant when the valve is commanded to open and the time when the vacuum sensor reading reaches an acceptable vacuum level.

(b) Vacuum obstruction: An obstruction in the vacuum line between the vacuum sensor and the actuator will result in a shorter vacuum transition time as well as long operation time of vacuum-actuated edge-contact gripper when the vacuum is turned on.

Vacuum-Actuated Edge-Contact Gripper

The substrate grippers, shown in FIGS. 5 and 6 may fail in some of the following ways.

(a) Broken spring: In the absence of vacuum, the spring loaded plunger is pushed against the substrate to grip it in place. A broken spring causes the gripper to be always in the "released" state.

(b) Jammed plunger: The plunger can be jammed and this results in no change in the gripper state in response to the opening or closing of the vacuum line.

Bearings and Ball Screws

Bearings and ball screws may fail gradually in some of the following ways.

(a) Binding: Binding of ball bearings cause an increase in resistance to motion. Binding results in an increase in motor current, motor temperature and energy dissipation and tracking error. It also results in an increase in tension in the belts that drive the affected joints.

(b) Play: Play in the bearings results in errors in position recorded by external position sensors such as an externally mounted video camera. If the bearing is part of a motor, it can also result in misalignment of the stator and result in symptoms discussed earlier. Play can also lead to oscillatory behavior and reduce the stability margin.

Communication System

The communication network transfers data between the master controller and the motor controller. Failure modes for the communication network may include the following.

(a) Slip ring failure: Slip rings transmit data across a rotary joint and can degrade gradually due to wear and tear. Degradation of slip rings is detected through an increase in the error rates in the data received by the individual controllers.

(b) Failure of communication module on the motor controllers: The master controller listens to status messages from the motor controllers. The master controller can detect failure of a motor controller by detecting the absence of status messages from that motor controller. This process is also referred to as "node guarding."

(c) Failure of communication module on the master controller: The motor controllers receive regular trajectory information from the master controller. A breakdown of the master controller is detected by the absence of any trajectory information. This process is also referred to as "heart beat monitoring."

(d) A break in communication link between two adjacent motor controllers: A fault of this kind results in one of the following two symptoms. If there is redundancy in the network, the host controller is able to re-map the network and continues to operate in a different network topology. If there is no redundancy, the host is unable to re-map the network. The location of the failed link can be determined based on the new network topology, in the former case, or the list of nodes that could not be mapped, in the latter case.

Substrate Mapper

A substrate mapper is generally an on-off sensor that registers two state transitions for each mapped substrate. Its failure modes may include the following types.

(a) Noisy sensor output: This results in multiple (more than two) state transitions per substrate and/or an odd number of state transitions.

(b) Faulty mapper sensor: A faulty sensor results in no state transitions.

Brake Failures

Motor brakes are usually electro-mechanically actuated and may have one or more of the following failures:

(a) Brake does not release: This results in continuous rubbing of the brake pad against the rotor and causes a position dependent variation of motor current. In addition there is an overall increase in tracking error, energy dissipation, heat dissipation and a change in the acoustic and vibration spectrum (b) Brake partially released: This results in intermittent rubbing of the brake pad against the rotor and causes a position dependent variation of motor current. In addition there is an overall increase in energy dissipation, heat dissipation and a change in the acoustic and vibration spectrum.

External Obstruction

An external obstruction results in a rapid increase in motor currents and an increase in difference between the actual motor current and the model predicted motor current. The rate of increase in motor currents depends upon the type of obstruction. A soft obstruction is one in which the motor current increases gradually. An example of a soft obstruction is one encountered by the end-effector of a robot (in FIG. 4), with its arm extended and moving in the Z direction. The flexibility of the arm results in the motor currents increasing linearly with respect to displacement. In the event of a hard obstruction, the motor current increases abruptly. An example of a hard obstruction is one encountered by the end-effector of a robot (in FIG. 4), moving in the radial direction.

A more direct symptom of interference with an external obstruction is increase of deflection indicated through strain-gauges, if available.

Cooling Fans

Fans used to cool the motors and electronics can fail to operate resulting in an increase in overall system temperature with no accompanying increase in motor current levels.

Power Supply

Typical modes of failures resulting from a power supply malfunction are listed below.

(a) Voltage below specification: The voltage sensors in the motor controllers explicitly indicate an "under voltage" fault. In the absence of such sensors, this condition is characterized by higher duty cycle and position tracking error.

(b) voltage above specification: The voltage sensors in the motor controllers explicitly indicate an "over voltage" fault. In the absence of such sensors, this condition is characterized by lower than normal duty cycle.

(c) Blown fuse: This is detected through voltage sensing at the fuse output terminal. The voltage is close to zero when the fuse is blown.

Robot-Level Failures (a) Repeatability deterioration: The robot looses its capability of positioning the end-effector repeatedly to the specified location. This failure typically develops gradually, and can be detected as variation in the position data captured when the robot end-effector is detected by external sensors during motion, or using video images of the robot end-effector commanded repeatedly to a given location.

(b) Mispick/misplace: This fault can be diagnosed using video recording of pick and place operations of the robot by video camera(s) installed either on the robot arm or at the locations where pick and place operations take place.

Aligner/Mapper Light Intensity Fluctuation

The intensity of light emitted by the light emitter in an aligner or a mapper can fluctuate (degrade) gradually over a long period of time. In the case of a mapper, a significant drop in intensity can result in erroneous data on the presence or absence of a substrate between the light emitter and the light detector. In the case of an aligner, it can result in erroneous data on the extent to which the light emitter is blocked. This, in turn, results in faulty or out-of-range wafer edge position data in the aligner. This, typically gradually developing, failure can be detected as variation (reduction) of the sensor output when fully exposed to the light source.

Supporting Systems

Fan-Filter Unit

The fan-filter unit includes a filter, which typically covers a majority of the top cross-sectional area of the atmospheric section of the tool. Gradual filter clogging is indicated by increasing plenum pressure on the input side of the filter (plenum pressure) in order to maintain the same pressure inside of the atmospheric section of the tool (mini-environment pressure).

Ionizer Failure

Ionizers are devices used to neutralize charges accumulating on the substrates transferred in the atmospheric section of the tool. Failure of the ionizer results in excessive charge accumulation on the substrates.

Tool-Level Failures

Repeatability Deterioration

Tool-level failures include substrate repeatability deterioration, robot-station misalignment and throughput reduction.

Substrate Repeatability Deterioration

Substrate repeatability deterioration is the loss of the capability of the tool to deliver substrates to one or more stations repeatedly within a specified tolerance. This make be a side effect of robot repeatability deterioration, due to substrate slippage on the robot end-effector or because of a malfunction of the aligner, to name a few examples. This failure typically develops gradually, and can be detected as variation in position data captured when substrate edges are detected by external sensors during motion, or based on video images when substrates are delivered to a given location.

Robot-Station Misalignment

Proper alignment of stations with respect to the robot is critical for proper operation of the tool. Misalignment can be detected as variation in auto-teach and auto-level results.

Throughput Reduction

Throughput is measured by the number of substrates processed by the tool per hour. Throughput reduction is indicated by an increase in substrate cycle time.

Techniques for HMFD

Methods of implementing the four basic functions, data collection, pre-processing, analysis, and reasoning will be described in further detail. There are many different types of methods available for data collection, pre-processing, analysis and inference and each of the methods is suited to detection and identification of certain types of faults.

Monitoring and Analysis of Energy Dissipation

This approach is suitable for implementation of an early-detection system for robot faults. The underlying principle in this approach is that faults that result from a degradation of mechanical or electrical components of the robot will result in a decrease in the overall efficiency of operation of the robot. Therefore, such faults can be detected in the early stages of occurrence by monitoring certain measures of energy dissipation in the robot. Some examples of faults that result in a decrease in efficiency are: damaged or misaligned bearings, loss of lubrication, obstruction to robot motion, deterioration of the permanent magnets on the rotor and malfunctioning motor brakes. There are several types of energy dissipation that can be monitored during robot operation.

Mechanical Energy Dissipation

One measure of energy dissipation is the total mechanical energy dissipation during a sequence of robot operations. This is given by the following expression:

$$\Delta E_{total,mech} = \sum_{i=1}^{N} \int_{\Delta T} \tau_i \dot{\theta}_i dt - \Delta E_{pot} \quad (1)$$

where $\tau_i$ and $\dot{\theta}_i$ are the output torques and angular velocities of the individual motors and N represents the number of motors in the robot, $\Delta T$ is the time duration of the sequence of robot operations and $\Delta E_{pot}$ is the change in potential energy of the robot.

The term $\Delta E_{pot}$ includes changes in gravitational potential energy and energy stored in compliant elements like springs and bellows. The change in potential energy is a constant for a given sequence of operations and can be computed from the difference in potential energy between the start and end positions of the robot. An increase in the total mechanical energy dissipation, over time, would indicate a fault resulting from degradation of a mechanical component.

Electrical Energy Dissipation

Another measure of energy dissipation is the total electrical energy dissipated in the motors during a sequence of robot operations. This is given by the following expression:

$$\Delta E_{total,elec} = \sum_{i=1}^{N} \int_{\Delta T} V_i I_i dt - \Delta E_{pot} \quad (2)$$

where $V_i$ is the voltage input to the motor and $I_i$ is the motor input current.

An increase in the total electrical energy dissipation would indicate a fault resulting from a degradation of an electrical or mechanical component of the robot.

Energy Loss in the Individual Joints

Useful information on the location of the malfunctioning component can be obtained by monitoring the energy loss in the individual joints on the robot. For example, the mechanical energy dissipation in each of the individual joints can also provide useful information on a malfunctioning bearing or brake in the specific joint. The expression below gives the mechanical energy loss in joint i of the robot.

$$\Delta E_{i,mech} = \int_{\Delta T} \tau_i \dot{\theta}_i dt \quad (3)$$

Similar to its mechanical counterpart, variation in electrical energy loss in the individual motors also provides useful information on impending failure of the specific motor:

$$\Delta E_{i,elec} = \int_{\Delta T} V_i I_i dt \qquad (4)$$

The energy dissipation based condition monitoring can be implemented in a real system in one of the following two ways: The first approach assumes that there exist move sequences that the robot repeats over an extended period of time. Such move sequences can be used as templates for health monitoring and fault diagnostics. Data on energy dissipation, torque and other motion characteristics can be measured for a normal robot and stored for future use. Since substrate handling robots continuously engage in transportation of substrates among a set of stations, a move sequence that accomplishes a movement of a substrate from one station to another will qualify as a template sequence for health monitoring. The second approach involves the development of a "normal" robot model, e.g., using neural networks, and using this model to compute the energy dissipation in a normal robot. This model-computed energy dissipation can be compared to the actual energy dissipation to determine if there is an increase in energy dissipation over time.

The following types of faults can be detected through this approach: Disintegration of motor magnets, stator misalignment, higher connector resistance, higher belt tension, increase in friction in any of the moving components, defective ball bearings, presence of brake drag, incorrect commutation angle and malfunction of a phase.

Monitoring and Analysis of Torque Residuals

A torque residual is a measure of the difference between the actual motor torque and a baseline estimate. An analysis of torque residuals can identify certain types of faults that can occur in the robot. This approach is based on comparison of torque data obtained during operation of the robot with torque data that represent normal behavior of the robot. The baseline torque data (the data that represent normal behavior) can be obtained either as raw data stored initially for selected move sequence templates or from a model of the robot. In addition to the raw value of torque residual, the integral of the absolute value of the residual over a given move sequence is also a useful indicator of the over all robot health.

Raw Data Storage for Selected Move Sequence Templates

This approach assumes that there exist move sequences that the robot repeats over an extended period of time. Such move sequences can be used as templates for health monitoring and fault diagnostics. Data on energy dissipation, torque and other motion characteristics can be measured for a normal robot and stored for future use. Since substrate handling robots continuously engage in transportation of substrates among a set of stations, a move sequence that accomplishes a movement of a substrate from one station to another will qualify as a template sequence for health monitoring. The "settle" event at the extend position of one station can trigger the start of a template move sequence and the settle event at the extend position at the next station can trigger the end of the health monitoring move sequence. It is thus possible to have multiple template sequences, one for each pair of stations. A major drawback with this approach is that reference data collected for a move sequence is valid only as long as the move parameters remain unchanged.

Analytical Robot Model

A normal behavior of a robot can be represented by a dynamic model derived analytically for a given mechanical design. Once the structure of the model is derived, the parameters of the model can be calculated based on the physical properties of the mechanical components involved, often with a help of CAD models, or obtained experimentally using parameter estimation techniques. The drawback of this approach is that separate dynamic models need to be derived for different configurations of robot arm mechanisms, and some physical phenomena, such as friction, are difficult to describe analytically with the required accuracy.

Neural Network Based Robot Model

As an alternative to an analytical model, data obtained from a normal robot can be used to build a neural network model of the robot dynamics. Conveniently, the same type of neural network can be used for multiple configurations of the robot arm mechanism, the training of the model can be easily automated, and neural network models typically represent well complex physical phenomena that are often difficult to describe analytically.

Exemplary faults that can be identified based on analysis of torque residuals include reduction in effective motor capacity and periodic drag.

Disturbance Observers

Disturbance observers are commonly used in the servo control of robotic manipulators. They provide estimates of disturbances not accounted for in the robot model. These observers can be designed to be stable at higher bandwidths compared to the position servos and hence enable better tracking control of the robot manipulator. The disturbance estimate provided by a disturbance observer for each motor in the robot serves as a convenient property that can be monitored to detect abnormalities. The disturbance observer can be used to detect faults that occur abruptly or intermittently. Examples of such faults are: brake drag that occurs at certain motor positions, belts rubbing at certain motor positions, external obstructions to motion, sudden fluctuations in input voltage.

Monitoring and Analysis of Motor Power Consumption

Motor power consumption is a useful indicator of the overall health of the robot. Like energy dissipation described above, an increase in power consumption points to a potential fault in the robot. Like motor torque, power consumption is a property of the current state of the robot and its variation can yield useful information on the type of fault.

Monitoring and Analysis of Tracking Errors

Monitoring and analysis of tracking errors is an approach that can reveal a health problem. Tracking error is defined as the difference between the actual position of a given axis or component of a robot and the commanded (desired) position for this axis or component. This health monitoring approach is based on comparison of tracking errors collected during regular operation of the robot for selected template sequences of operations with baseline data obtained initially when the robot was in a normal health condition. A change or a trend in the tracking errors under otherwise identical operating conditions indicates a health problem.

In addition to the raw tracking error, the following two derived quantities of tracking error serve as useful health indicators: normalized tracking error and integral of the absolute value of tracking error over a move sequence.

(a) Normalized tracking error: Tracking error tends to be strongly correlated to the acceleration and the rate of change of acceleration of the motors, and may increase proportionally. A better indicator of robot health may be a normalized tracking error in which the effect of other motion parameters is factored out.

(b) Integral of tracking error: The integral of the magnitude (absolute value) of the tracking error over an entire move sequence is a measure of the overall tracking error during the move.

Monitoring and Analysis of Encoder Signals

The analog signal output of each encoder comprises of two sine signals that are of equal amplitude, but phase shifted from each other by 90 degrees. The following defects can be detected by monitoring a shift in the amplitude and phase properties of the signals: a change in phase difference indicates a misalignment of the encoder read head or wobbling of the encoder disk; a change in amplitude indicates the presence of debris on the encoder disks.

Analog encoder signals can be monitored either during normal operation or during specific motion patterns induced for the purposes of fault diagnostics. A desirable motion pattern is a constant velocity motion that results in constant frequency sine signals.

Monitoring and Analysis of Heat Dissipation

Heat dissipation is another form of energy dissipation. The amount of heat dissipation at various points on the robot can also be used to predict impending faults. Any fault that results in higher friction between moving components will result in a higher level of heat dissipation. In addition, higher current levels in motors and solenoidal switches will also result in higher heat dissipation. Higher motor current levels are in turn the result of many different types of faults.

Heat dissipation can be monitored through infrared sensors mounted at strategic points in the tool, aimed at the robot. Temperature can be measured using temperature sensors present inside motors and motor controllers. This method can be used to detect the following types of faults: disintegration of motor magnets, incorrect motor phase angle, misalignment of stator, increase in bearing friction, brake drag.

Monitoring and Analysis of Structural Vibrations

Another approach to advance detection of impending faults is to monitor the structural vibrations at various points on the robot. Structural vibrations can be monitoring either directly through accelerometers and strain gauges or indirectly through acoustic signals. Impending failure can be predicted by detecting significant shifts in the power spectrum of the acoustic signals and the structural vibration signals. For example, a faulty bearing or a rubbing belt will result in an increase in acoustic energy levels and in the introduction of new "peaks" in the signal power spectrum. A change in belt tension can be detected by a shift in the "peaks" of the power spectrum.

Acoustic energy can be measured using microphones placed at various points on the robot. Structural vibration can be measured by mounting accelerometers at various points on the robot. Similar to the energy dissipation approach described above, certain move sequences that the robot repeats over a period of time can be used as template sequences based on which the power spectrum for a normal robot can be compared with that for a faulty robot. The signals can also be measured in response to a controlled excitation of the structure at certain orientations of the robot. The following types of faults can be analyzed using this method: increase or decrease in belt tension, loose fasteners, increase in bearing friction and rubbing of moving components.

Frequency Response Analysis

A change in properties of a robotic manipulator, which may be associated with a health problem, can be identified using a frequency response analysis. In this approach, a frequency response of a robot is compared with a baseline frequency response obtained initially for the robot in normal condition. The comparison can be based on raw data or on transfer functions and other mathematical representations obtained by parameter estimation techniques from the raw data.

Typically, the data necessary for frequency response analysis cannot be obtained during normal operation of a robot since the motion profiles are generally designed to minimize excitation of the robot structure. Consequently, the data collection process needs to take place when the robot is not utilized for regular operation. The data can be obtained by commanding the robot to a pre-defined grid of positions, and injecting excitation signals to the motors of the robot while monitoring the response of the robot through encoder readings in each of the positions. The excitation may be in the form of a white or pink noise, a swept-frequency harmonic signal or a single-frequency harmonic signal the frequency of which changes incrementally in specified steps over the frequency range of interest.

The health problems that may be identified by a frequency response analysis could include loose mechanical hardware, worn parts, and incorrect tension of belts.

Monitoring of Belt Tension

The tension of the belts that drive robot links and other components in a robotized manufacturing tool, such as belts 415, 418A, 418B, 419A and 419B in FIG. 4, can be monitored through sensors which detect the force between the belt and the corresponding belt tensioner. The forces are typically read when the robot is stationary in a given position. A change or trend in the forces indicates a health problem.

Furthermore, the force detected by the sensors during operation of the robot can be used to estimate the torque transmitted by the corresponding belt drive. This information can be used to narrow down a problem, such as mechanical binding, to a particular component in the robot.

For instance, if a motor with a two-stage belt drive, such as motor 417A with belts 418A and 419A in FIG. 4, outputs higher torque than expected and the torques transmitted by both of the stages remain normal, the problem resides in the mechanics before the first stage of the belt drive. However, if the first stage transmits higher than normal torque, the problem should be looked for between the two stages of the belt drive. Finally, if both of the stages transmit abnormal torque levels, the problem is in the components beyond the second stage of the belt drive.

Static Force Balance Analysis

The relationship between the motor current and motor torque is determined by the motor torque-current relationship (also referred to as the motor torque capacity). A fault such as a weakening of the motor magnets will result in a drop in the motor torque capacity. Such a fault can be identified by directly measuring motor torque and motor current. Direct measurement of motor torques is possible under static load conditions. An example of a static load condition is that of a robot arm that is stationary, but resisting an external force. If the external force can be measured through a force gauge, the torques in the individual motors can be determined.

Even if the magnitude of the external force is unknown, the analytical static force models can be used to obtain the ratios between motor torques. The motor torque ratios can be compared with the motor current ratios and a fault leading to a drop in motor capacity can be identified. The following faults can be identified using this approach: weakening of motor magnets, play in motor bearings. The relation ship between motor torque, T and peak motor current, $I_{phase}$ in a three phase motor is given by the following expression.

$$T = \frac{3}{2} nLRBI_{phase} = K_t I_{phase} \quad (5)$$

where L is the winding length along the motor axis, R is the radius of the coil winding and B is the magnetic field normal to the coil and $K_t$ is the motor torque constant or the motor torque capacity.

In addition to measuring motor torque constant, static analysis can be used to identify changes in motor winding resistance. Under static conditions the relationship between motor lead-to-lead winding resistance, motor lead voltage and motor lead current is given by $$V_{lead} = \frac{\sqrt{3}}{2} I_{lead} R_{l-l} \quad (6)$$

for both a Delta and Wye wound motor.

Monitoring and Analysis of Digital Sensor Outputs

Digital sensors are ON/OFF sensors placed at different subcomponents of the robot. By monitoring and recording the state transition time, certain types of faults can be detected. The state transition time can be recorded either during normal operations or during specific operations designed for diagnostics.

Vacuum-actuated edge-contact grippers may have additional sensors that detect the position of the plunger (FIG. 5). The grip-on transition time for this sensor increases if there is a vacuum leak or if there is an obstruction in the vacuum system.

For the purpose of this document, electrical circuits for detection of blown fuses also fall into the category of digital sensors.

Monitoring and Analysis of Analog Sensor Outputs

Analog optical sensors are used to align substrates in a substrate aligner. The analog outputs from these sensors are passed through analog-to-digital converters and read by the controller. The signal amplitude determines the extent of eccentricity of the wafer in the aligner. Any attenuation of the signal strength coming from the source, which is an LED, needs to be detected and accounted for. This attenuation may be due to the deterioration of the LED source.

To monitor the condition of the aligner sensor, calibration of the LED source can be done periodically in the absence of any substrate on the aligner. The attenuation of the LED source can be compensated for in the controller software and/or the voltage supplied to the LED source can be adjusted. A similar monitoring and analysis approach can be applied to a substrate mapper sensor.

Alternatively, if a substrate is always present on the aligner, the calibration of the LED source can be done based on the known diameter of the substrate. Regardless of the eccentricity of the substrate, a pair of values can be found in the data collected that represent the radius of the substrate with no eccentricity. The sensor readings at these two points can be checked against the expected nominal value of the substrate radius.

Vacuum pressure sensors are analog sensors that indicate the vacuum level. This vacuum pressure is compared against a pressure threshold to determine if the desired vacuum state is reached. The vacuum transition time, which is the time it takes to reached the desired vacuum state, can be used to determine certain faults. In the case of a vacuum-actuated edge-contact gripper or surface-contact suction gripper (FIGS. 5 and 6) a change in state transition time during gripping and un-gripping may indicate a leak or obstruction in a certain section of the vacuum system.

Monitoring and Analysis of Video Signals

A video camera can be mounted in the workspace of the robot and connected to the controller. The controller can process the video images and detect certain types of faults. For example, the video signals can be used to determine the repeatability of the robot. A video image of the robot end-effector can be captured and analyzed when the robot is at a particular location. The image can be analyzed using pattern recognition tools to determine if there is a significant shift in the location of certain features on the end-effector.

A video camera can also be installed directly on the robot end-effector to monitor pick and place operations performed by the robot, including the operation of the edge-contact gripper. The resulting video can be recorded and serve in diagnostics of failures during pick and place operations. This is an extremely valuable tool for failures that occur rarely, cannot be observed by the operator and/or are difficult to reproduce. Video signals can be used to identify faults that affect robot position repeatability. Typical faults that affect repeatability are slipping of timing belts, belt stretching leading to hysteresis and loosening of bearing clamps.

Monitoring and Analysis of Communication Network Traffic

The condition of the communication network may be monitored through error rates (i.e., a number of errors per a specified amount of data transferred) across individual links of the communication network. This approach is particularly practical to monitor the condition of slip-rings that carry communication signals.

In addition, fatal communication network failures at motor controllers can be monitored by the master controller through network node guarding. In this approach, the master controller monitors, for instance, the presence of periodic status messages sent by each of the motor controllers.

Similarly, fatal communication network failures at the master controller can be detected by motor controllers through heartbeat monitoring. In this case, the motor controllers monitor, for example, the occurrence of periodic trajectory frames from the master controller.

Change Detection Methods

The fault diagnosis methods described above involve the monitoring of various physical characteristics of the robot, such as, energy dissipation, motor torques, torque residuals, tracking errors, belt tension and peak vibration frequencies, to name a few. The monitoring of these characteristics involve comparing them with certain thresholds and signaling a fault if they exceed or fall below those thresholds. Such a technique is used in statistical quality control and is also referred to as a control chart. Several statistical techniques have been developed for control charts and these methods can be applied to health monitoring as well.

Two fundamental requirements need to be met for the use of control charts. The first is a definition of a performance metric, in terms of the physical characteristics defined above, with a known statistical distribution model. The second is a definition of thresholds, derived from the level of confidence (also referred to as confidence coefficient) with which the change in the performance metric is to be predicted. The variation of the metrics is monitored and compared with thresholds. Depending upon the metrics used, the control charts are classified into various types. The Shewhart control chart uses the last observation as the performance metric. For a confidence coefficient of 99.7% the upper and lower control limits are chosen as $(\mu+3\sigma)$ and $(\mu-3\sigma)$, where $\mu$ is an estimated mean and $\sigma$ is the estimated standard deviation. It is ideal for detection of abrupt changes in values of the physical characteristics, such as a temporary spike in the motor torque or following error or power consumption, to name a few. On the other hand, the Exponentially Weighted Moving Average (EWMA) is used as a metric for detecting slow drifts in the values of the physical characteristics, such as, energy dissipation, belt tension, to name a few. The EWMA is defined as follows.

$$EWMA_i = (1-\lambda)EWMA_{i-1} + \lambda X_i \quad (7)$$

where $X_i$ is the measurement at iteration I and $0 \leq \lambda \leq 1$ and $EWMA_0$ is the estimated mean at the start of the monitoring process.

The standard deviation of the EWMA is given by $$\sqrt{\frac{\lambda}{2-\lambda}}\sigma,$$

where $\sigma$ is the estimated standard deviation of the property being monitored.

A majority of the faults are characterized by changes in values of two or more physical characteristics which are strongly correlated to each other. In such cases, the Hotelling's T-square statistic will used as the performance metric to detect sudden changes. To detect slow drifts in a multivariate framework, the Multivariate EWMA charts will be used. Both of these methods yield a single scalar quantity which is a measure of the square of the deviation from the nominal and accounts for the covariance between variables in a multivariate framework.

Baselining of Normal Behavior

The change detection algorithms assume the existence of baseline estimates of the physical characteristics that are being monitored. An example of a baseline estimate is the mean of the energy dissipated during a specific move sequence. Baselining is an important step in fault detection and will involve data collection and processing to obtain estimates of the physical characteristics. Data collection will be done under normal operating conditions, which refers to the condition when the robot has no known defects. Data collection will involve averaging over several repeated measurements obtained under the same operating conditions. A measurement may be a single value, such as total energy dissipated during a specific operation or maximum absolute value of tracking error or maximum absolute value of motor torque, or a sequence of values such as motor torque values measured at regular intervals during a specific operation. The measured values will be stored in a database along with specifications on the conditions under which the data was collected.

Data processing may take one of several forms. One form is system identification, which involves estimation of a set of base parameters that comprise an analytical model of the system. Another form is the development of neural network models that model either the entire system or only certain nonlinear effects that do not have analytical model.

Data normalization and trend cancellation is another form of data processing that may be required. In order to apply the control charts for change detection, the metric that is being monitored needs to have a constant nominal value under normal operating conditions. In reality, however, the physical quantities being monitored may show either gradual temporal drifts even under normal operating conditions. One example is that of energy dissipation that has been observed to show a gradual downward trend as a function of time. In order to effectively use such quantities in a control chart, the trend has to be modeled and canceled in the observed data. There are established Time Series analysis techniques that can be applied to this purpose. One method that can be applied to model long-term gradual trends is the Holt-Winters method or the Double Exponential Smoothing Method. Data normalization is also necessary if there is a correlation between the physical quantities and the operating conditions such as operating speed settings.

Specific HMFD Operations

Specific operations of the present health-monitoring and fault-diagnostic system will now be described. These operations may be grouped into four distinct categories: status and history information, continuous health monitoring, on-demand health monitoring, and diagnostic functions.

Status and History Information

The present health monitoring and fault diagnostics system provides the user with information on the history of the extent of the usage and the faults that occurred over a period of time. Following is the list of quantities that the system makes available to the user.

(a) Current robot servo state: This refers to whether the position feedback servo is activated for each of the motors. If all of the motors have their feedback servos enabled, the robot is in a "servo-active" state. If not, the robot is in "servo-inactive" state.

(b) Total duration of robot "servo-active" state: This refers to the overall duration of time, in days, hours, minutes and seconds, for which the robot is in "servo-active" state since the robot was first commissioned.

(c) Duration of current "servo-active" session: This refers to the duration in days, hours, minutes and seconds of the current "servo-active" session. If the robot is currently not in servo-active state, this quantity refers to the duration of the last servo-active session.

(d) Duration of robot motion: This refers to the time duration for which the robot is in motion as part of its normal operation.
(e) Number of motion errors: This refers to the number of times the robot servo state changed from "active" to "inactive" due to an error condition.
(f) Mean motion duration between errors: This refers to the mean of the time duration between successive motion errors.
(g) Motor "mileage": This refers to the distance in degrees or mm that each motor has moved by.
(h) Number of substrate acquire/release operations: This indicates how many pick/place operations the robot performed.

A summary of the status and history data can be found in Table 4.

TABLE 4

History and Status Information

| | |
|---|---|
| Purpose | Current robot servo state |
| Overview | Indicates whether the position feedback servo is activated for each of the motors. If all of the motors have their feedback servos enabled, the robot is in a "servo-active" state. If not, the robot is in "servo-inactive" state. |
| Feasibility of implementation | Easy to implement; does not require theoretical development or experimental verification; does not require additional sensors or hardware |
| Implementation priority | High (excellent benefit-to-effort ratio) |
| Purpose | Total duration of robot "servo-active" state |
| Overview | The overall duration of time, in days, hours, minutes and seconds, for which the robot is in "servo-active" state since the robot was first commissioned. |
| Feasibility of implementation | Easy to implement; does not require theoretical development or experimental verification; does not require additional sensors or hardware |
| Implementation priority | High (excellent benefit-to-effort ratio) |
| Purpose | Duration of current "servo-active" session |
| Overview | The duration in days, hours, minutes and seconds of the current "servo-active" session. If the robot is currently not in servo-active state, this quantity refers to the duration of the last servo-active session. |
| Feasibility of implementation | Easy to implement; does not require theoretical development or experimental verification; does not require additional sensors or hardware |
| Implementation priority | High (excellent benefit-to-effort ratio) |
| Purpose | Duration of robot motion |
| Overview | The time duration for which the robot is in motion as part of its normal operation. |
| Feasibility of implementation | Easy to implement; does not require theoretical development or experimental verification; does not require additional sensors or hardware |
| Implementation priority | High (excellent benefit-to-effort ratio) |
| Purpose | Number of motion errors |
| Overview | The number of times the robot servo state changed from "active" to "inactive" due to an error condition |
| Feasibility of implementation | Easy to implement; does not require theoretical development or experimental verification; does not require additional sensors or hardware |
| Implementation priority | High (excellent benefit-to-effort ratio) |
| Purpose | Mean motion duration between errors |
| Overview | The mean of the time duration between successive motion errors |
| Feasibility of implementation | Easy to implement; does not require theoretical development or experimental verification; does not require additional sensors or hardware |
| Implementation priority | High (excellent benefit-to-effort ratio) |
| Purpose | Motor "mileage" |
| Overview | The distance in degrees or mm that each motor has moved by |
| Feasibility of implementation | Easy to implement; does not require theoretical development or experimental verification; does not require additional sensors or hardware |
| Implementation priority | High (excellent benefit-to-effort ratio) |
| Purpose | Number of substrate acquire/release operations |
| Overview | Indicates how many pick/place operations the robot performed |
| Feasibility of implementation | Easy to implement; does not require theoretical development or experimental verification; does not require additional sensors or hardware |
| Implementation priority | High (excellent benefit-to-effort ratio) |
| Purpose | Error Reports |
| Overview | Notification when error condition occurs, including the primary source of the error, the corresponding error code and a description of the error |
| Feasibility of implementation | Easy to implement; does not require theoretical development or experimental verification; does not require additional sensors or hardware |
| Implementation priority | High (excellent benefit-to-effort ratio) |
| Purpose | Logging of Diagnostic Information |
| Overview | Information on all system operations, changes in system state and system errors are logged in a file |
| Feasibility of implementation | Easy to implement; does not require theoretical development or experimental verification; does not require additional sensors or hardware |
| Implementation priority | High (excellent benefit-to-effort ratio) |

The present health monitoring system may also provide an error log that includes the date and time of occurrence of the error and the results of diagnostic methods that were executed in the aftermath of the error. More information on error reporting and logging is provided below.

Error Reports: In the event of a hardware or software error that disrupts normal operation, the monitoring system reports the error to the user. Each error report comprises the following information: the primary source of the error, the corresponding error code and a description of the error. If applicable, it may also contain the secondary source of the error, the corresponding error code and a description of the error.

Logging of Diagnostic Information

Information on all system operations, changes in system state and system errors are logged in a file. The format of each entry in this file is configurable and may contain the following information: time of origination, the originating source and a description. Logging can be further configured in the following manner the sources can be selected from a list; the level of

Continuous Health Monitoring

Continuous health monitoring of the robot and other devices in the tool is accomplished by measuring some or all of the measurable signals during normal operation, and analyzing the resulting data. The measurement and analysis functions may occur continuously or periodically, but always in parallel with the normal operation. The purpose of the continuous monitoring is to detect signs of health deterioration and, if possible, to locate the sub-components that may cause this deterioration. These functions may not, however, point to the specific cause of the problem.

Robot/Aligner Overall Health Based on Energy Dissipation

This method involves the use of energy dissipation to detect deterioration of robot health. The underlying principle is that a deterioration of robot health results in a reduction in operating efficiency of the robot and therefore an increase in energy dissipation.

Purpose

The purpose of energy dissipation monitoring is to detect the onset of faults in the robot that result in a decrease in energy efficiency.

Overview

The energy dissipated during certain move sequences is computed for the whole robot as well as for individual joints in the robot. This computed dissipation is compared against the energy dissipation for a normal robot. An increase in the energy dissipation points to a degradation in robot health. This method is ideal for detecting the onset of faults that result in a decrease in energy efficiency of the robot.

Hierarchical Level

This method may be implemented in the master controller that controls the overall motion. Each of the motor controllers may stream data on winding current, voltage and velocity of the respective motors to the master controller. Data collection, pre-processing, analysis and reasoning operations may be performed in the master controller.

Sequence of Steps (a) The manager signals the data collector to begin or end the recording of data required to compute energy dissipation. The beginning and end of data collection needs to coincide with the instances when the robot comes to a complete stop. The robot comes to a complete stop when it picks up or places a substrate.
(b) The data collection layer records motor voltage, motor current, motor velocity, motor position and motor commanded acceleration for each of the motors in the system. In addition, it also records the time for each set of data.
(c) The pre-processing layer computes energy dissipation in each of the motors using the integral energy equations above. It computes the baseline value of energy dissipation using the model based on one or more of the methods described above. It computes two types of monitoring metrics: the difference between the computed value and the baseline value, and the exponentially weighted moving average of the difference. It also computes upper thresholds based on the confidence coefficient.
(d) The analysis layer monitors the metrics for each of for each of the move sequences. It detects whether the monitored metrics exceed the corresponding pre-determined upper threshold values.
(e) The reasoning layer uses the individual motor energy dissipation information for multiple move sequences and identifies the sub-component of the robot that has a problem.
(f) If a problem is found, the manager initiates further diagnostic routines to narrow the cause of the problem.

Configuration Data (a) Start point and end point of sequence of operations for which energy dissipation is calculated;
(b) Baseline value for energy dissipation for the above sequence of operations or a set of model parameters that enable the computation of the nominal torque.
(c) Size of the moving average sample (not necessary if using EWMA).
(d) Confidence coefficients to be used to compute thresholds.
(e) Rate of data collection—number of data points per second of operation.

Failure Modes

Monitoring of energy dissipation enables the detection of the onset of the following faults: incorrect motor phase angle, relative motion between encoder and motor rotor, relative motion between the motor windings and the housing, weakening (disintegration) of motor magnets, high connector resistance, bearing binding, play in the bearings, ball-screw binding, belt rubbing and brakes not released completely.

Robot/Aligner Overall Health Based on Torque/Current Residual

This approach involves the monitoring of motor torque and current residuals. A significant change in the residual would indicate a degradation in the overall health of the robot. Since motor torques are not easily measurable, with the exception of the static case described above, they need to be estimated from motor winding currents and the motor torque model. As a result, a change in motor model torque-current relationship will have an effect on the estimated torque residual.

Purpose

This approach is suitable to detect faults that result in an increase in resistance to the rotation of the motors. In addition, if the motor torque is estimated from the motor current, faults that result in a reduction in motor torque capacity will also be detected.

Overview

This method assumes that there is either a set of motor current data stored a priori or there is a robot dynamic model available that can predict the motor current based on the present and past robot states. The current thus predicted is compared with the current measured at the individual motors to obtain the current residual. The residual is monitored over time and a significant drift in its value indicates the onset of a fault. A change in the current residual can be result of the following two causes. It could reflect a change in the motor physical properties such as phase angle, demagnetization or misalignment. It could also reflect a change in the external resistance to the motor rotation, that requires in a higher torque output from the motor. In addition to the torque residual, the integral of the torque residual over an entire move sequence is also monitored.

Hierarchical Level

This method may be implemented in the master controller that controls the robot motion. Each of the motor controllers may stream data on winding current, position and velocity of the respective motors to the master controller. Data collection, pre-processing, analysis and reasoning operations may be performed in the master controller.

Sequence of Steps (a) The manager signals the start and end of data collection for each motor. If there is only a limited bandwidth for streaming data from the remote controllers, data collection could be performed one motor at a time. Data collection could also be triggered at certain pre-determined motor locations or move sequences. The duration of data collection could also be varied depending upon the robot state.

(b) The data collection layer records motor current; it may also record position, velocity and acceleration if dynamic model is used.

(c) If dynamic model is used, the pre-processing layer calculates the model-based torque. If torque data is collected at specific motor locations, the pre-processing layer will compute the torque residual as a monitoring metric. On the other hand, if torque data is collected for an entire move sequence, the pre-processing layer will compute the integral of the absolute value of the torque residual over the entire move sequence as a monitoring metric. It will also compute the moving averages of each of the above as additional monitoring metrics. In addition, it will compute threshold limits for each of the metrics described above. The pre-processing layer will also perform a fast Fourier transform on segments of the raw torque data.

(d) The analysis layer monitors the metrics defined above and detects deviations of the metrics beyond the threshold limits. This also monitors the emergence of and shifts in peaks in the frequency spectrum.

(e) The reasoning layer evaluates data from different motors at different times and identifies the robot sub-component that is at fault. It also identifies the robot locations where the abnormality is most perceivable.

(f) The manager uses the information from the reasoning layer to launch specific diagnostic methods.

Configuration Data (a) Robot move sequence, start location and end location for data collection for each motor. There may be multiple start and end locations for each motor.
(b) Confidence coefficients for computation of thresholds.
(c) Size of moving average sample.
(d) Rate of data collection—number of data points per second of operation.
(e) Baseline values of torques based on measurements from a normal robot or a set of parameters that would enable computation of nominal torques.

Failure Modes

Monitoring of motor torques and currents enables the detection of the onset of the following faults: incorrect motor phase angle, relative motion between encoder and motor rotor, relative motion between the motor windings and the housing, disintegration of motor magnets, bearing binding, ball-screw binding, belt rubbing, brake drag, etc.

Robot/Aligner Overall Health Based on Power Consumption

Power consumption can be monitored and analyzed in a manner similar to the monitoring and analysis of motor torque described previously. The advantage that power consumption monitoring has over torque monitoring is the power consumed generally only increases in the presence of a fault. This property of power consumption simplifies application of thresholds in fault detection.

Robot/Aligner Overall Health Based on Tracking Errors

This approach involves the monitoring of tracking errors. A higher than normal tracking error indicates the presence of a problem.

Purpose

This approach is suitable to detect faults that result in an increase in resistance to the rotation of the individual motors and faults that result in servo instability.

Overview

Tracking error is the difference between the required motor position and the actual position. A higher tracking error level indicates that the motor is experiencing a higher than normal resistance to its motion which occurs due to one or many fault conditions. In addition, a significant oscillation of the tracking error indicates instability in the servo loop which occurs due to one or many fault conditions.

Hierarchical Level

This method will be implemented in the master controller that controls the robot motion. Each of the motor controllers will stream data on desired position, actual position and velocity of the respective motors to the master controller. Data collection, pre-processing, analysis and reasoning operations will be performed in the master controller.

Sequence of Steps (a) The manager signals the start and end of data collection for each motor. If there is only a limited bandwidth for streaming data from the remote controllers, data collection could be performed one motor at a time. Data collection could also be triggered at certain pre-determined motor locations or move sequences. The duration of data collection could also be varied depending upon the robot state.

(b) The data collection layer records the required position and actual position for each motor.

(c) The pre-processing layer computes several monitoring metrics based on the tracking error. If data is collected at certain pre-determined motor locations, the absolute value of the peak tracking error serves as a monitoring metric. On the other hand, if data is collected over the length of certain pre-determined sequences, the integral of the square of the tracking error serves as a monitoring metric. In addition, it performs a fast-Fourier transform on segments of the data on tracking error.

(d) The analysis layer detects any overall increase in the magnitude of the peak tracking error, in the integral of the square of the tracking error and compares them against thresholds. It also detects any new dominant frequency components in the tracking error signal.

(e) The reasoning layer uses analysis results over several instances of data collection and confirms a change in robot characteristics. It also reports to the manager on the robot locations and velocities where there is an abnormality in the tracking error.

(f) The manager uses the information from the reasoning layer to launch specific diagnostic methods.

Configuration Data (a) Start locations and end locations and move sequences for data collection for each motor. There may be multiple start and end locations for each motor.
(b) Threshold levels on tracking error, threshold on the integral of the square of the tracking error for each motor and for each move sequence.
(c) Sample size for FFT analysis.
(d) Rate of data collection—number of data points per second of operation.

Failure Modes

Monitoring of tracking error enables the detection of the onset of the following faults: incorrect motor phase angle, relative motion between encoder and motor rotor, relative motion between the motor windings and the housing, disintegration of motor magnets, bearing binding, ball-screw binding, belt rubbing, brake drag; etc.

Robot/Aligner Motor Model Validity

This method involves the monitoring of the conformance of motor voltage, current, position and velocity to the motor model. Any deviation from the motor model prediction would point to a fault that results in a change in one of the motor physical properties.

Purpose

The purpose of this method is to detect faults that may result in a change in one or many of the motor physical properties.

Overview

A motor model relates physical characteristics such as field strength, winding resistance, inductance, field gap width to properties such as motor current, voltage, position and velocity. The equations that define the motor model under static conditions are detailed above. Under dynamic conditions, the input voltage will also have to overcome the back emf which is proportional to the motor velocity. A fault can result in a change in one of the physical characteristics. Monitoring the conformance of the above properties to the motor model would enable the detection of a change in the physical characteristics Hierarchical Level This method will be implemented in the master controller that controls the robot motion. Each of the motor controllers will stream data on position, velocity, current and voltage of the respective motors to the master controller. Data collection, pre-processing, analysis and reasoning operations will be performed in the master controller.

Sequence of Steps (a) The manager signals the start and end of data collection for each motor. If there is only a limited bandwidth for streaming data from the remote controllers, data collection could be performed one motor at a time. Data collection could also be triggered at certain pre-determined motor locations or move sequences. The duration and frequency of data collection could also be varied depending upon the robot state.
(b) The data collection layer records motor voltage, motor current and motor velocity and motor position;
(c) The pre-processing layer calculates modeled current based on the voltage and velocity recorded; it then calculates the residual as a difference between the actual and modeled current, and determines the maximum variation
(d) The analysis layer compares the maximum variation with an allowable threshold.
(e) The reasoning layer uses analysis results over several instances of data collection and confirms a change in robot characteristics. It also reports to the manager on the robot locations and velocities where there is an abnormality in the variation.

Configuration Data (a) Motor properties, including resistance, inductance and back emf constant;
(b) Allowable range for residual.

Failure Modes

Change in electrical properties of motor, cables and motor drive circuitry (such as resistance increase due to connector problem), change in magnetic properties of the motor (weaker magnet affects back emf constant), incorrect bus voltage (since motor voltage is most likely going to be measured in terms of commanded PWM), slipping of encoder or motor coil housing.

Robot/Aligner Encoder Data Integrity—Incremental Encoders

Purpose

The purpose of this method is to identify problems with the position reading mechanism in the encoder.

Overview

Encoders come in two types: incremental and absolute and the mechanism for fault detection depends upon the encoder type.

In an incremental encoder, position is measured by counting the number of encoder counts that have passed by the read head. If for any reason, there are missed counts, the reported position would be incorrect. Incremental encoders have an index pulse that occurs once every revolution. The controller records the incremental position reading on the arrival of each index pulse. If there are no missed counts, the difference between position readings at any two index pulses should be an integer multiple of the number of incremental counts per encoder revolution. In reality a few missed counts is inevitable and a warning is recorded if the number of missed counts exceeds a threshold level.

Hierarchical Level

This method is best implemented in the remote motor controllers.

Sequence of Steps

Figure 10:
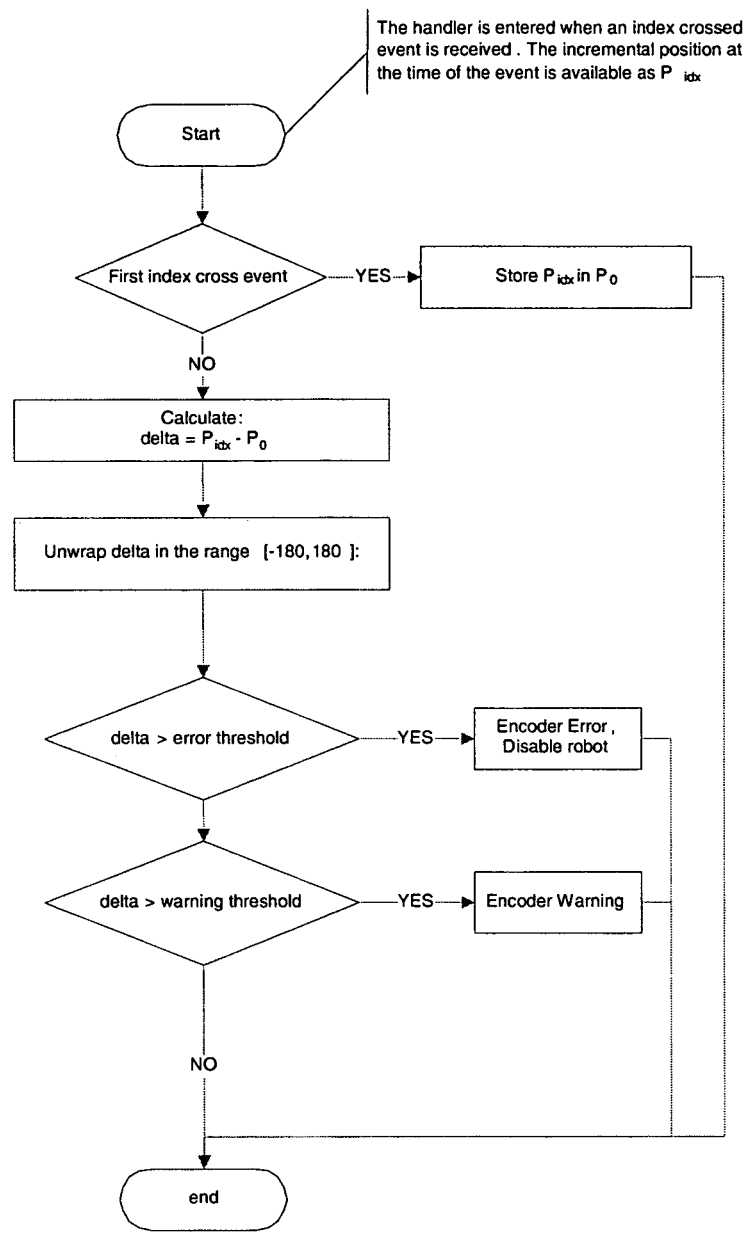
FIG. 10 shows a method for incremental encoder data integrity checking.

Referring to the flow chart in FIG. 10,
(a) The manager will set up a mechanism to generate an event when the index pulse is read.
(b) When an event is generated, the data collection layer records the incremental position.
(c) The analysis layer computes the difference between positions at successive index pulses and determines if the difference is within a tolerance of a multiple of the number of incremental counts per revolution.
(d) The reasoning layer reports the occurrence of encoder faults.

Configuration Data (a) Tolerance on missed encoder counts.

Failure Modes

Missed counts are reported when dirt on the encoder disk prevents the encoders from being read correctly.

Robot/Aligner Encoder Data Integrity—Absolute Encoders

Purpose

The purpose of this method is to identify problems with the position reading mechanism in the absolute encoder.

Overview

Encoders come in two types: incremental and absolute and the mechanism for fault detection depends upon the encoder type.

In an absolute encoder, the absolute position is read either on initialization or in response to a forced absolute position read command. The encoder reads the absolute position and thereafter increments its actual position in a manner similar to the incremental encoder. If there are no encoder faults, for a stationary encoder, the position obtained by updating the encoder should match the position obtained by a forced absolute position read.

Sequence of Steps

Figure 11:
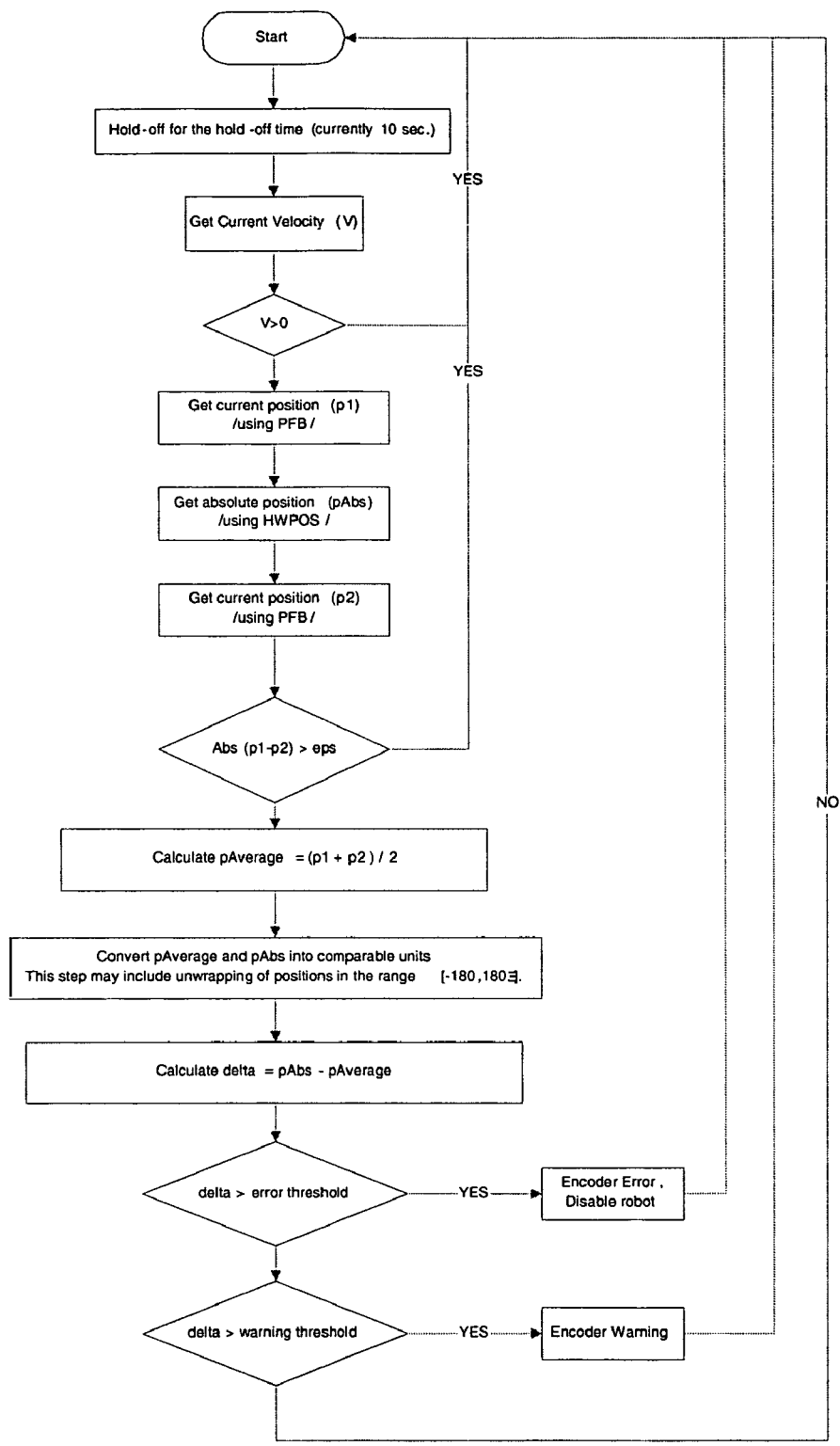
FIG. 11 shows a method for absolute encoder data integrity checking.

Referring to the flow chart in FIG. 11, (a) The manager will set up a mechanism to read absolute position at regular intervals and to read the actual position before and after the absolute position read.
(b) The analysis layer computes the difference between the two actual positions. It checks if the encoder is stationary by checking if the difference in actual positions is less than a tolerance.
(c) If the encoder is stationary, the analysis layer computes the difference between the absolute position and the average of the actual positions.
(d) The reasoning layer reports the occurrence of encoder faults.

Hierarchical Level

This method could be implemented either in the main controller or the remote motor controllers.

Configuration Data (a) Tolerance on stationary condition
(b) Tolerance on error condition Failure Modes Absolute encoder errors occur due to dirt on encoder disks as well as due to software or hardware malfunction.

Continuous Belt Tension Monitoring

The tension in the belts driving the arms can be continuously monitored through direct measurements of the belt tension using force sensors mounted on the idler pulleys (of belt tensioners). A significant drop or increase in the belt tension will be reported as a potential problem.

Monitoring of Structural Vibrations

The monitoring of structural vibrations helps in the detection of onset of faults. Structural vibrations can be monitoring either directly through accelerometers and strain gauges or indirectly through acoustic signals. Impending failure can be predicted by detecting significant changes in the power spectrum of the acoustic signals and the structural vibration signals. The change in power spectrum could be in the form of a change in the magnitude of a "peak" or a shift in the "peak" frequency. Acoustic energy can be measured using microphones placed at various points on the robot. Structural vibration can be measured by mounting accelerometers at various points on the robot. The following types of faults can be analyzed using this method: increase or decrease in belt tension, loose fasteners, increase in bearing friction and rubbing of moving components.

Monitoring of Heat Dissipation

Heat dissipation is another form of energy dissipation. The amount of heat dissipation at various points on the robot can also be used to predict impending faults. Any fault that results in higher friction between moving components will result in a higher level of heat dissipation. In addition, higher current levels in motors and solenoidal switches will also result in higher heat dissipation.

Heat dissipation can be monitored by measuring the rise in temperature of various components in the robot. The rise in temperature can be measured either with infrared sensors aimed at strategic points on the robot or through temperature measurement sensors inside the motors.

Heat dissipation monitoring is performed by the master controller. Following are the steps involved.

(a) The data collection layer records temperature at various points on the robot over a period of time.
(b) The analysis layer compares the temperature with a threshold.
(c) If the threshold is exceeded, the reasoning layer reports a problem with that component.
(d) The manager directs further tests to determine the cause of the problem.

The following types of faults can be detected by monitoring heat dissipation: disintegration of motor magnets, incorrect motor phase angle, misalignment of stator, increase in bearing friction, brake drag.

Monitoring of Cooling Fans

Cooling fans are often utilized to remove heat generated by motors and electronics. Since there is a relationship between the energy dissipation in the motors and electronics subject to cooling and their temperature, the condition of cooling fans and air ducts can be monitored through temperature of the motors and electronics subject to cooling.

Monitoring of Robot/Aligner Over-Travel Switches

Purpose

The purpose is to detect over-travel that may result from a software malfunction, position feedback problem, motor amplifier problem or mechanical failure, such as an encoder or belt slippage.

Overview

Over-travel switches are mechanical or optical sensors that are triggered when a robot axis travels beyond its prescribed limits. A change of state of these sensors is immediately detected by the robot controller, which, in turn, takes the necessary follow up steps.

Hierarchical Level

This diagnostic routine may reside in a robot controller or in a master controller PC.

Sequence of Steps

The following steps take place when an over-travel condition is detected:

(a) The manager disables all axes of motion associated with the robot;
(b) The manager engages brakes for all axes that are equipped with brakes;
(c) The manager generates an error, identifying the axis that violated its bounds and the axis position.

Configuration Data (a) Association of over-travel switches with axes of motion.

Failure Modes

The failure modes that can be detected are as follows: malfunctioning encoders, belt slippage, and malfunctioning software.

Robot/Aligner Gripper and Vacuum System Health

The operation of the wafer grippers is enabled by the vacuum system. Problems with the vacuum system can be diagnosed by monitoring the gripping action. There are two types of vacuum based wafer grippers, namely, the surface-contact suction gripper in FIG. 6 and the edge-contact vacuum actuated gripper in FIG. 5. Two types of vacuum problems can occur; a vacuum leak and a vacuum line obstruction. Vacuum leaks can occur due to wear and tear on the lip seals. A leak in the vacuum line results in a lower vacuum pressure (when vacuum valve is open and, in case of surface-contact suction gripper, substrate is present on the end effector), and can be detected through a drop in the vacuum sensor (502, 502) reading. In addition, a gripping action results in either no gripping or an increase in the gripper operation time. For the vacuum-actuated edge-contact gripper, the grip operation time is measured between the instant when the valve (506, 606) is commanded to open and the time a position sensing flag (508) detects open state of the gripper. For surface-contact suction gripper, the grip operation time is measured between the instant when the valve is commanded to open and the time when the vacuum sensor reading reaches an acceptable vacuum level. An obstruction in the vacuum line between the vacuum sensor and the actuator will result in a shorter vacuum transition time as well as long operation time of vacuum-actuated edge-contact gripper when the vacuum is turned on. In addition to vacuum line problems, mechanical problems such as a jammed plunger or a broken spring can also result in malfunctioning of the gripper.

Communication Network Health

Purpose

The purpose of this is to detect problems with the data communication network.

Overview

There is constant data flow between the master controller and the remote controllers. The remote controllers send their status to the master controller at approximately periodic intervals and the master controller sends control information to the remote controllers at approximately periodic intervals. The frequency of arrival of these massages is monitored. A drop in frequency of arrival of these massages causes the controller to issue a warning about a possible slow down in the network traffic.

In addition to monitoring frequency of error messages, the communication port in each motor controller has a record of the number of errors that occurred in that port over a period of time. This number provides an estimate of the overall health of the network.

A common cause of a break in network traffic is the loss of communication across slip rings.

Hierarchical Level

This diagnostic routine resides in the robot controller. In Fusion, this is the master controller PC.

Sequence of Steps (a) The data collector records the time at which the status messages from the nodes arrive. It also records the error count stored in the communication port of each of the controllers.
(b) The analysis layer determines if the interval between successive status packets exceeds a certain threshold and identifies the nodes that fall under this category. It also compute the rate of occurrence of new errors in the communication port of each of the controllers.
(c) If the threshold has been exceeded, based on the nodes whose status packets are missing, the reasoning layer identifies the branch and the link in the network topology that has the problem.

Configuration Data (a) Threshold on maximum allowable delay in reception of status messages.
(b) Network configuration.

Failure Modes

Failure of communication across slip rings, malfunctioning communication processors on the remote controllers, loose contacts in the network connectors.

Continuous Robot Repeatability Monitoring

The position repeatability of a robot can be monitored through external stationary sensors. The sensor can sense the position of the robot end-effector as it stops during regular operation. As an alternative, a camera can be employed either as an external stationary device or carried by the robot. Typical faults that affect repeatability are slipping of timing belts, belt stretching leading to hysteresis and loosening of bearing clamps.

Substrate Repeatability Monitoring

Similarly, substrate position repeatability can be checked using external stationary sensors. This check can reveal problems with a substrate aligner, substrate slippage on the robot end-effector, for instance due to dirt on the supporting pads or deterioration of the material of the supporting pads, malfunction of a gripper, misalignment of robot end-effector with respect to stations where substrates are picked from and/or placed to, causing substrate "walking", etc. Alternatively, a camera can be used for this purpose.

Monitoring of Pick/Place Operations

This method utilizes a video camera installed on the robot arm so that it has a full view of the end-effector as the robot performs pick and place operations. The video data are continuously streamed to the robot controller during operation. A pre-defined duration of the video recording is stored by the controller. When a mispick or misplace failure occurs, the video recording stops. The video data stored by the controller then can serve as a valuable source of information for diagnostic purposes.

Continuous Virus Scan

The purpose of this method is to identify the presence of software viruses in the system that may result in loss of data or degradation in performance.

The robot controller may run an operating system which may have security loopholes that could be exploited by software viruses. Periodic virus scan will enable the detection of a software virus before it results in loss of data and degradation in performance. The virus scan may be scheduled and performed by the operating system itself or by a third party tool. The required configuration data is the desired frequency of the virus scan.

Monitoring of Fan-Filter Unit Filter

The purpose of this feature is to monitor the filter in the fan-filter unit for clogging. Clogging is detected by simultaneous monitoring of plenum pressure (on the input side of the filter) and mini-environment pressure (in the atmospheric section of the tool). If increased plenum pressure is needed to maintain the same mini-environment pressure under otherwise identical conditions (closed doors, unchanged air exhaust properties) indicates filter clogging.

Monitoring of Ionizer Functionality

Ionizers are devices used to neutralize charges accumulating on the substrates transferred in the atmospheric section of the tool. Failure of the ionizer results in excessive charge accumulation on the substrates. Ionizer failure can be detected by measuring the change in the environment. If the measured charge exceeds a positive or a negative threshold, the ionizer is likely to be malfunctioning.

A summary of the continuous health-monitoring functions is provided in Table 5.

TABLE 5

| Continuous health monitoring |
| --- |
| Robot/Aligner Overall Health Based on Energy Dissipation |
| Robot/Aligner Overall Health Based on |

TABLE 5-continued

Continuous health monitoring

Torque/Current Residual
Robot/Aligner Overall Health Based on Power Consumption
Robot/Aligner Overall Health Based on Tracking Errors
Robot/Aligner Motor Model Validity
Robot/Aligner Encoder Data Integrity
Continuous Belt Tension Monitoring
Monitoring of Structural Vibrations
Monitoring of Heat Dissipation
Monitoring of Cooling Fans
Monitoring of Robot/Aligner Over-Travel Switches
Robot/Aligner Gripper and Vacuum System Health
Communication Network Health
Continuous Robot Repeatability Monitoring
Monitoring of Pick/Place Operations
Continuous Virus Scan
Monitoring of Fan Filter Unit Filter
Monitoring of Ionizer Functionality Automatic Fault Diagnostics If any of the health monitoring methods reports deterioration in the operation of the robot, the next step is to identify the root cause of the problem. Methods that can be used primarily for diagnosing faults with data obtained during a normal operation of the robot are as follows.

Current/Torque Residual Analysis

Torque residual analysis involves the analysis of the variation of the difference between the actual torque and nominal torque. The variation pattern is used to determine the type of fault that is causing the performance deterioration.

Purpose

The purpose of this method is to diagnose faults that have a distinct torque signature. The diagnosis is done by analyzing time series data on torque residual. This method would be executed if an increase in energy dissipation or tracking error or a change in torque residual is reported in a particular motor and if the motor property diagnostic check finds no problems with the motor properties.

Overview

Certain faults have a distinct fault signature and those faults can be diagnosed by analyzing the torque residual. The torque residual is the difference between the actual torque and the nominal torque signals. The nature of variation of the torque residual with respect to position, can indicate certain types of faults. For example, a periodic variation of the residual with respect to motor position indicates that the cause of the problem is a position dependent drag force such as periodic brake drag due to a misalignment of brakes.

Hierarchical Level

This method will be implemented in the master controller that controls the robot motion. Each of the motor controllers will stream data on position, velocity and current in the respective motors to the master controller. Data collection, pre-processing, analysis and reasoning operations will be performed in the master controller.

Sequence of Steps (a) The manager will trigger the start and end of data collection for the motor in question. Data collection should be triggered in the constant velocity section of the motion. In order to get well-conditioned data, the move sequences should involve sufficient variation in position.

(b) The data collection layer records motor voltage, motor torque and motor velocity and motor position.

(c) The pre-processing layer first makes sure that the position data has sufficient range and a certain minimum variance. If not, it signals the manager to issue a new data collection command using perhaps a different start point and a longer duration. It also isolates and uses only data collected during the constant velocity phase. It computes the nominal torque based on the motor model and the residual as the difference between the actual torque and the nominal torque. It computes the mean and variance of the residual. It also computes the Fourier transform of the residual with respect to position. How about auto-correlation?.

(d) The analysis layer determines if the residual is above a certain threshold. It checks for peaks in the Fourier spectrum and reports the peak frequencies. It also determines the distance that corresponds to a period of oscillation of the residual.

(e) If the residual is below a threshold, the reasoning layer reports that it has no fault to diagnose. If there are peaks present in the Fourier transform and if the period corresponding to the peak equals the distance covered in one revolution of the motor, it reports that the fault is a drag force that is periodic with respect to position.

A summary of the automatic fault diagnostic functions of the present HMFD system is provided in Table 6.

TABLE 6

Automatic fault diagnostics

Current/Torque Residual Analysis
Motor Power Consumption Analysis
Tracking Error Analysis
Obstruction Detection
Analysis of Disturbance Observer Data
Belt Tension Analysis
Frequency Domain Analysis Motor Power Consumption Analysis Motor power consumption is a useful indicator of the overall health of the robot. Like energy dissipation described above, an increase in power consumption points to a potential fault in the robot. The presence of higher friction at certain joints results in an increase in power consumption at the motor driving the joint. Also, the presence of a periodic drag due to rubbing brakes will yield a periodically varying power dissipation.

Tracking Error Analysis

An increase in tracking error beyond a threshold is an indicator of a problem. In addition, a fast Fourier Transform of the tracking error will yield information on the amplification of certain vibration modes.

Obstruction Detection

Obstructions that the robot arm encounters can be detected by analyzing the motor forces and tracking error.

Analysis of Disturbance Observer Data

The output of a disturbance observer is a measure of the disturbance force on the actuator. Analysis of the variation of this output will yield insight into the nature of the fault. For example, the presence of a periodic drag due to rubbing brakes will yield a periodically varying disturbance observer output. The presence of an obstruction will result in an output that increases with displacement.

Belt Tension Analysis

Belt tension can be continuously measured using force sensors and analyzed to detect problems. Higher friction at a particular joint will result in greater tension in the belt driving that joint.

Frequency Domain Analysis

The purpose of this method is to diagnose faults with specific frequency-domain signature. This signature may be present in a variety of signals. As an example, analysis of the structural vibration at various points on the robot can yield useful pointers to the source of the problem. For example, loose bearings result in a larger amplitude for certain frequency peaks. In addition, increased rubbing at loose bolt results in higher damping for certain modes of vibration. Identifying the specific changes in the vibration spectrum can help pin point the source of the problem.

On-Demand HMFD Routines

The functions described herein complement the continuous health-monitoring and fault-diagnostic capabilities described above. They cannot be performed during normal operation of the robot since they require special sequences and/or can endanger the substrate. As opposed to continuous monitoring and automatic diagnostics, these functions are used on demand in the following situations:

(a) For health-monitoring purposes when the tool is not utilized or when it is serviced during scheduled maintenance;
(b) For diagnostic purposes when a health problem or fault was detected by another method to narrow the cause and/or to confirm/eliminate a suspect component.

Robot/Aligner Model Identification

The purpose of this on-demand routine is to identify the parameters of the rigid-body dynamic model of the robot or aligner. Differences in the parameters indicate changing properties of the robot (aligner) properties, often due to a developing fault.

The identification process is automatic. The HMFD system commands the robot to follow predetermined trajectories and monitors the positions and torques during the robot motion. The structure of the dynamic model is selected to reflect all important mechanical components of the system and includes actuator dynamics associated with the motors of the robot. In order to achieve reliable results, the model is formulated in terms of the base parameters, and the trajectories are optimized for the resulting structure of the dynamic model.

Robot/Aligner Frequency Response

The purpose of frequency response identification is to determine changes in natural frequencies and damping levels, which indicate changes in the robot structural properties, including loose mechanical couplings. The frequency response provides magnitude and phase characteristics in multiple positions of the robot.

In order to construct the frequency response, the HMFD system moves the robotic manipulator to a grid of positions distributed uniformly in the workspace of the robotic manipulator, excites the robotic manipulator by a swept-frequency harmonic signal, and records the response of the robotic manipulator in each position. Using a complex least-square fit technique, the controller then uses the data recorded to calculate parameters of transfer functions for each position of the robotic manipulator.

The HMFD system may visualize the resulting frequency responses by graphing their magnitude and phase characteristics.

Robot/Aligner Joint Condition Check

The purpose of this on-demand routine is to check the condition of the mechanical joints. First, the HMFD system performs identification of the rigid-body dynamics of the robot or aligner. In the second step, the identification results that represent joint properties, such as damping and friction, are compared with baseline values. Changes outside of a specified range of expected values indicate a problem with the corresponding joint.

Robot/Aligner Belt Tension Check

Purpose

The purpose of this on-demand routine is to check the tension of the belts that may be used in robot arms against specifications.

Overview

Tension of belts that are used in robot arms may not be set correctly or change over time due to production/service personnel error, belt material creep or malfunction of the belt tensioning mechanism. Change in belt tension affects the performance of the robot, including the stability of the feedback control. Belt tension can be checked based on the frequency response of the robot. The data necessary for frequency response analysis cannot be obtained during regular operation, hence a special on-demand routine is required.

Hierarchical Level

This routine may reside in a robot controller or a master controller PC.

Sequence of Steps (a) The manager checks that no substrates are on robot end-effectors; an error is displayed if this is not the case; if the robot does not support substrate presence sensing, the manager displays a request for the operator to confirm that no substrates are on the robot end-effectors;
(b) The manager commands the robot to move to the robot's home position; an error is displayed if this operation fails;
(c) The manager switches the servo controller to servo parameters pre-defined for frequency response identification;
(d) The manager triggers excitation of the motors associated with the belt drives of interest; the data collection layer records the excitation and the response of the corresponding encoders;
(e) The pre-processing layer calculates frequency response of the robot based on the data obtained from the data collection layer; an error is displayed if frequency response cannot be calculated;
(f) The analysis layer identifies the frequencies that correspond to the transverse vibration of the belts of interest in the frequency response obtained from the pre-processing layer; an error is displayed if the frequencies cannot be identified; [Should it also identify frequencies corresponding to longitudinal vibration for belt condition check purposes?]
(g) The reasoning layer compares the resulting frequencies with the allowable ranges for each belt drive of interest; [Should this be done in the analysis layer?]
(h) The manager displays the results; if there is a problem, the manager offers a service screen with directions for belt tension adjustment.

Configuration Data (a) Association between belt drives and motors;
(b) Servo parameters for frequency response identification;
(c) Parameters of excitation signals for frequency response identification;
(d) Allowable natural frequency range for each belt drive.

Motor Model Validation Under Static Load Conditions

Purpose

The purpose of this method is to validate the motor torque constant.

Overview

The motor model equations are simplified under static load conditions. As explained above, if the motors resist a known external force under static conditions, in the absence of back emf, viscous effects and inertial effects, the motor torque constants can be directly derived from the measured current. Even if the magnitude of the external force is unknown, the analytical static force models can be used to obtain the ratios between motor torques. The motor torque ratios can be compared with the motor current ratios and a fault leading to a drop in motor capacity can be identified. The following faults can be identified using this approach: weakening of motor magnets, play in motor bearings. In addition, the motor winding resistance can also be derived from the measured current and voltage using the voltage-current relationship above.

Hierarchical Level

This diagnostic routine resides in a robot controller or a master controller PC.

Sequence of Steps (a) The manager will command the robot so that the robot end effector just touches the point of application of the external force. The external force may be known weight that the robot will pull or push against through a pulley or lever mechanism. If there is no external load the robot will push against a rigid surface.
(b) The manager will command one of the remote axis controllers to switch to "force mode" which would enable it to command a known torque at the motor corresponding to that axis.
(c) The data collection layer will record the steady state current and voltage values at each of the motors.
(d) The analysis layer will compute winding resistance values in each of the motors. In addition, it will compute residuals after substituting the current and external force values into the static equilibrium equations.
(e) The reasoning layer will compare the residuals with the thresholds and identify violation of the thresholds.
(f) The manager will report any violation of the motor model.

Configuration Data (a) Nominal values of motor winding resistance and motor torque constants.
(b) Allowable threshold limits on residuals.

Robot/Aligner Encoder Signal Check

Purpose

The purpose of this on-demand routine is to check the quality of the sine/cosine signals output by optical absolute and virtual absolute encoders against specifications.

Overview

Encoder read-heads and optical disks may not be aligned properly due to production/service personnel error or their alignment may change over time due to damage during operation. Dirt, such as dust or grease, may contaminate an optical disk of an encoder. Such a misalignment and contamination may distort the sine/cosine signals output by the encoder. The quality of the signals can be checked based on their amplitude and phase properties. The signals need to be recorded at a low constant speed, which condition generally does not occur during regular operation, hence a special on-demand routine is necessary.

Hierarchical Level

This diagnostic routine may reside in a robot controller or a master controller PC.

Sequence of Steps (a) The manager checks that no substrates are on robot end-effectors; an error is displayed if this is not the case; if the robot does not support substrate presence sensing, the manager displays a request for the operator to confirm that no substrates are on the robot end-effectors;
(b) The manager commands the robot to move to a safe position
(c) The manager commands the axis to move by the desired range with a constant velocity. The desired range corresponds to one complete encoder rotation.
(d) The data collection layer records the sine and cosine signal values at a specified rate.
(e) The pre-processing layer computes the magnitude of an imaginary vector whose Cartesian components are the sine and cosine signal values.
(f) The analysis layer records the maximum and minimum values of the sin and cosine signals as well as that of the imaginary vector.
(g) The reasoning layer compares the maximum and minimum values to pre-set thresholds.
(h) If any of the thresholds is violated, the manager reports the location.

Configuration Data (a) Maximum and minimum threshold levels.
(b) Rate of data collection.
(c) Safe robot position for each robot axis.
(d) Axis velocity during recording.

On-Demand Check of Robot/Aligner Gripper

The purpose of this routine is to verify proper operation of robot or aligner vacuum-operated substrate grippers as shown in FIGS. 5 and 6. Upon request, the HMFD system exercises the grippers while monitoring the transition times and comparing them with given specifications.

Mapper/Aligner Sensor Check

The purpose of this routine is to check robot mapper or aligner optical sensor for functionality. The HMFD system commands the sensor to turn the light emitter on and reads the output of the light receiver when it is fully exposed to the emitted light. The resulting output is compared with a given specification.

Robot Mapper Functionality Check

The purpose of this routine is to verify that the mapper (FIG. 7) functions properly. The HMFD system commands the robot to use the mapper to scan a feature of a known dimension, such as a wire or pin of circular cross-section with known diameter. The result is then compared with the known dimension of the scanned feature.

Robot/Aligner Control Stability Verification

The purpose of this routine is to verify stability of the robot or aligner controller tuning. The HMFD system moves the robot to a grid of positions distributed uniformly in the workspace of the robot, excites the robot by an impulse, step or swept-frequency harmonic signal, and records the response in each position. The controller then evaluates the stability margin based on the data collected.

Communication Network Topology Check

This check involves the determination and display of the topology of the communication network.

On-Demand Robot Repeatability Check

Purpose

The purpose of this is to detect any degradation in the repeatability of the robot.

Overview

Repeatability of the robot refers to the ability to command the robot end effector to the same point in the workspace within a certain tolerance. A measure of robot repeatability is the tightness of this tolerance window. Repeatability loss occurs due to sloppy mechanical coupling, such as play in bearings and slipping belts. Repeatability loss can be detected through repeated external measurements of the robot end effector location during the execution of the motion command. There are two possible modes of external measurement of the robot location. One option is to use the through beam mapper at the robot end effector (FIG. 7). The robot would move its end effector so that a fixed feature, such as a vertical knife edge, would cut the beam. The exact robot position where the beam is cut is noted. A gradual shift in this position indicates a problem with robot repeatability. In order to verify the robot's repeatability fully, the feature may be accessed by the robot from multiple directions, or multiple features may be used. A second option is to record the robot position where a straight edge of the end effector would cut a beam fixed with respect to the work cell.

Hierarchical Level

This diagnostic routine may reside in a robot controller or a the master controller PC.

Sequence of Steps (a) The master controller will identify and command the robot to perform certain move sequences that will allow one or more through beams to be cut.
(b) The data collection layer will record the robot positions where the through beam was cut.
(c) The analysis layer detects shifts in the recorded positions. If the shift is beyond a tolerance limit, a loss of repeatability is reported.

Configuration Data (a) Allowable tolerance on repeatability

Robot-Station Alignment Check

Purpose

The purpose this method is to check for any shift in the station location or its orientation with respect to the robot.

Overview

Describes methods to automatically determine station locations and station orientation with respect to the robot. The methods describe a sequence of steps using either the through-beam mapper 428A, 428B on the robot end effector or the aligner 307. When requested, the robot can perform these steps and check if there is a significant shift in the station location or orientation.

Hierarchical Level

This test may be implemented in the main robot controller.

Sequence of steps (a) The manager makes sure all the stations and the features on the stations that enable teaching are accessible.
(b) If the mapper (428A and 428B) is to be used for teaching, the manager checks to make sure there are no wafers on the robot end effector.
(c) The manager commands the start of the teach sequence.
(d) The manager records shifts in station locations and orientations and warns the user of deviations from normal.

On-Demand Virus Scan

This involves the scanning of the hard drives, such as those of the master controller, for viruses and other processes that impede the proper execution of the controller tasks.

A summary of exemplary on-demand health-monitoring and fault-diagnostic routines is provided in Table 7.

TABLE 7

| Exemplary On-demand HMFD routines |
| --- |
| Robot/Aligner Model Identification |
| Robot/Aligner Frequency Response |
| Robot/Aligner Joint Condition Check |
| On-Demand Robot/Aligner Belt Tension Check |
| Motor Model Validation under Static Load Conditions |
| Robot/Aligner Encoder Signal Check |
| On-Demand Check of Robot/Aligner Gripper |
| Mapper/Aligner Sensor Check |
| Robot Mapper Functionality Check |
| Robot/Aligner Control Stability Verification |
| Communication Network Topology Check |
| On-Demand Robot Repeatability Check |
| Robot-Station Alignment Check |
| On-Demand Virus Scan |

EXAMPLE TEST DATA

Exemplary test data for selected methods of the present health-monitoring and fault-diagnostic system will now be described.

Monitoring and Analysis of Energy Dissipation

As explained above, the underlying principle in this method is that faults that result from a degradation of mechanical or electrical components of the robot will result in a decrease in the overall efficiency of operation of the robot. Therefore, such faults can be detected in the early stages of occurrence by monitoring certain measures of energy dissipation in the robot. Some examples of faults that result in a decrease in efficiency are: damaged or misaligned bearings, loss of lubrication, obstruction to robot motion, deterioration of the permanent magnets on the rotor and malfunctioning motor brakes. In addition, vibration induced by marginal instability in the position and current feedback control loop also results in an increase in energy dissipation and can be detected using this approach. It should be noted that the energy loss indices only indicate the presence of faults in the robot and in the respective joints. Complementary methods may need to be employed to narrow the cause of the fault.

A 5-axis Reliance robot was used to gather data on energy dissipation during normal operation. This robot is similar to the example robot of FIG. 4. Using the trace mechanism built into the robot controller, motor torque and motor velocity data was downloaded each time the robot performed an extend move to pick a substrate from a non-radial station. The torque and velocity data was collected for the entire move that covered the duration of the robot starting from rest and coming to rest at the end of the move. Since this particular move did not involve the motion of the Z-axis, there is no change in the gravitational potential and under ideal frictionless conditions the net energy dissipation will be zero. On the other hand, for a real robot there is net positive energy dissipation as the robot moves between two points on the same plane. This energy dissipation is due to friction in machine components like bearings and actuators.

Energy Dissipation for a Normal Robot

Figure 12:
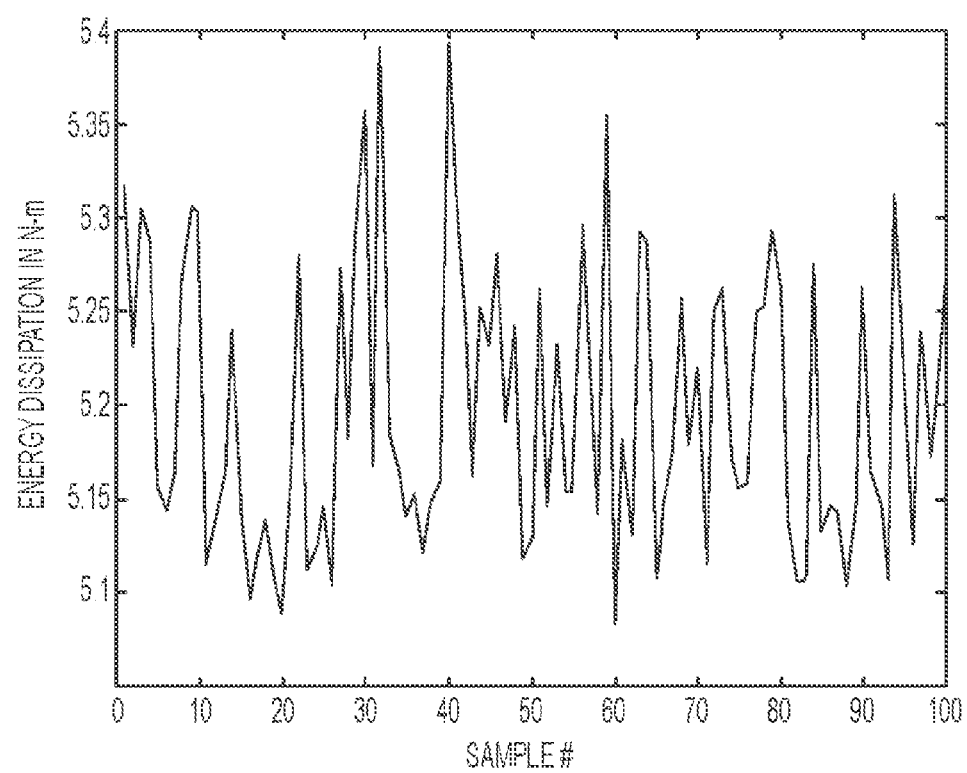
FIG. 12 shows a plot of the energy dissipation over successive extend moves to an off-center station for a robot in a normal condition.

FIG. 12 shows a plot of the energy dissipation over successive extend moves to an off-center station for the robot in a normal condition.

Energy Dissipation for a Robot with Incorrect Phase Angle

Figure 13:
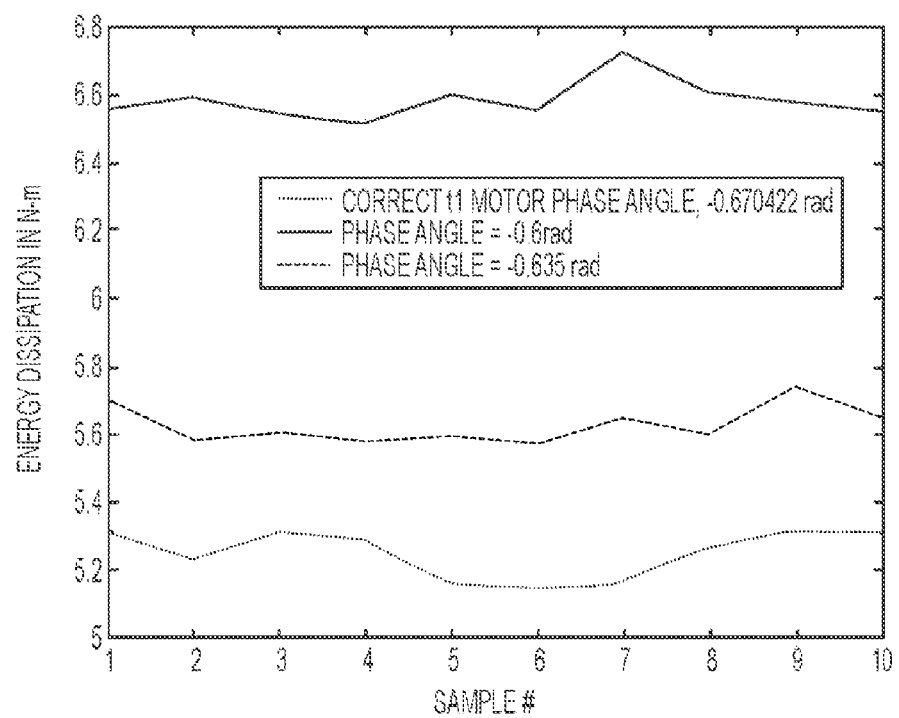
FIG. 13 compares the energy dissipation values for successive extend moves for different phase angles.

A fault condition was artificially induced in the robot by changing the phase angle of the t1 motor (motor 409 in FIG. 4). Incorrect phase angle results in a lower torque output of the motor for the same winding current. Since the actual required torque output of the motor stays the same, the motor current has to increase. This in turn results in a higher resistive energy loss. The resulting higher voltage manifests itself as a higher value of the actual torque in the feedback controller. This higher value of the actual torque can be used to compute the energy dissipation. FIG. 13 compares the energy dissipation values for successive extend moves for different phase angles.

Variation of Energy Dissipation Over Time

Figure 14:
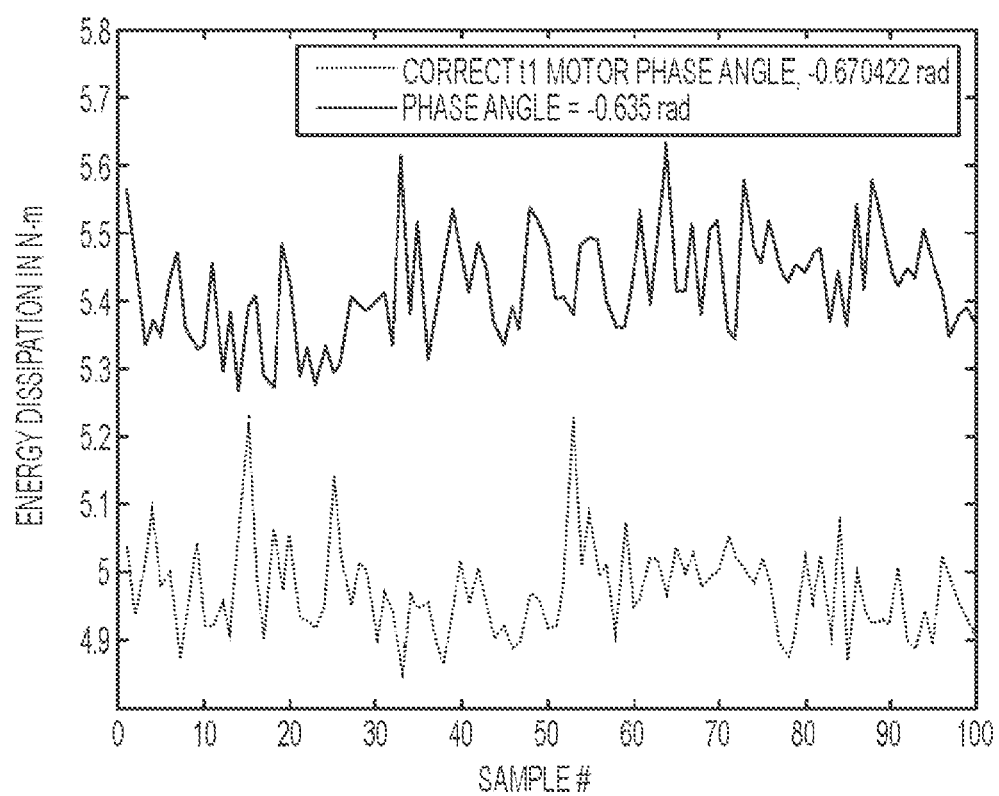
FIG. 14 shows the energy dissipation data for two different motor phase angles in the same robot after a 30-day interval.
Figure 15:
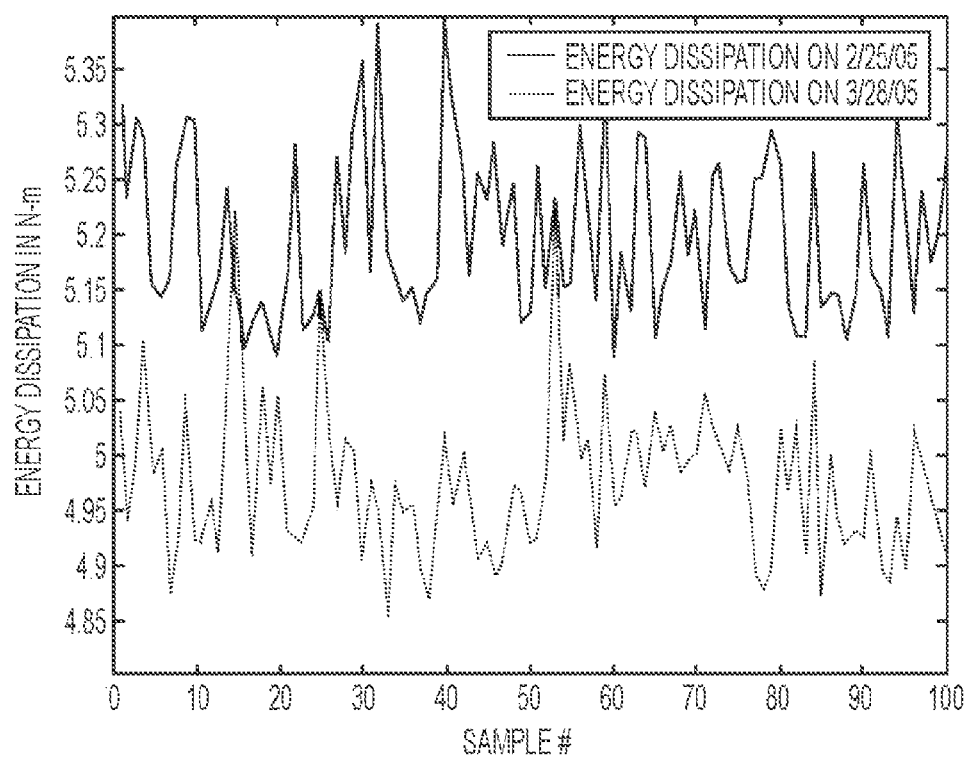
FIG. 15 compares the energy dissipation in a normal robot 30 days apart.

As can be seen from FIG. 12 and FIG. 13, the value of energy dissipation shows little variation over successive extend moves. However, for the robot under consideration, the energy dissipation showed a declining trend over a longer period of time. FIG. 14 shows the energy dissipation data for the same robot after a 30-day interval. FIG. 15 compares the energy dissipation in a normal robot 30 days apart. There is a 5% decline in all categories of energy dissipation. The reason for this drop in energy dissipation has not been determined yet. More analysis is needed on this issue.

Faults that Cannot be Detected by Monitoring Energy Dissipation

There are certain types of faults that may not result in a perceivable increase in energy dissipation and therefore cannot be detected by monitoring energy dissipation. Following are two examples:
(a) Dirt on the encoder disc resulting in incorrect position reading;
(b) Vibration due to a marginally stable servo: even though the energy dissipation does increase, it may not be significant enough to be detected.

Monitoring and Analysis of Torque Residuals

Data collected from a robot that is exhibiting a decline in overall health can be further analyzed to determine the specific fault that is causing it. As indicated previously, an analysis technique based on torque residuals that can identify certain types of faults that can occur in the robot.

Reduction in Effective Motor Capacity

Figure 16:
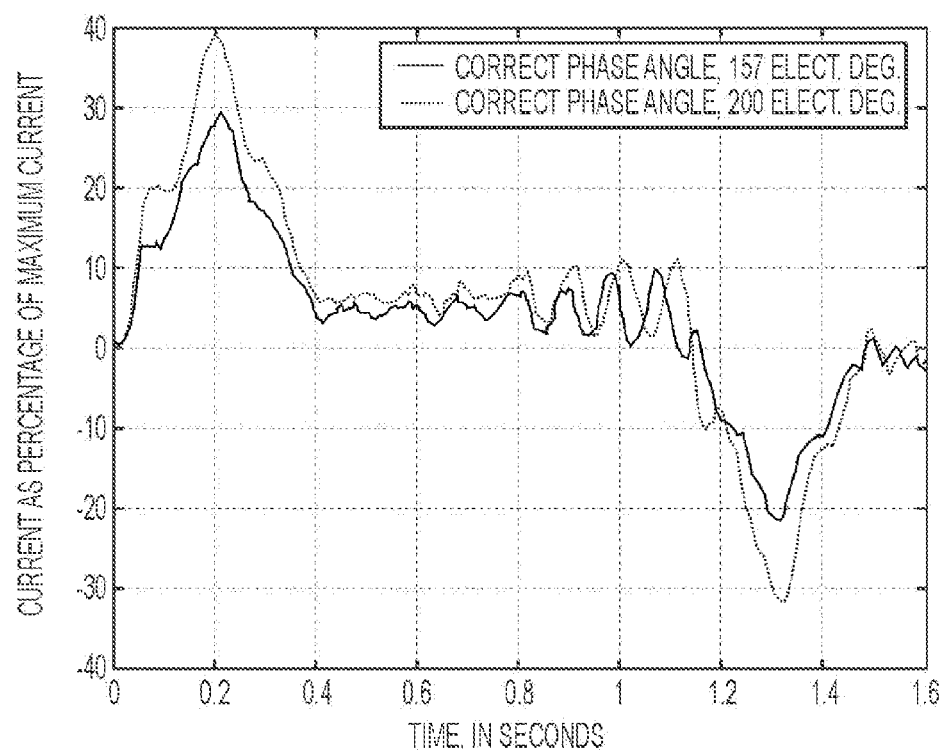
FIG. 16 shows a traverser motor current for two different phase angles over time.
Figure 17:
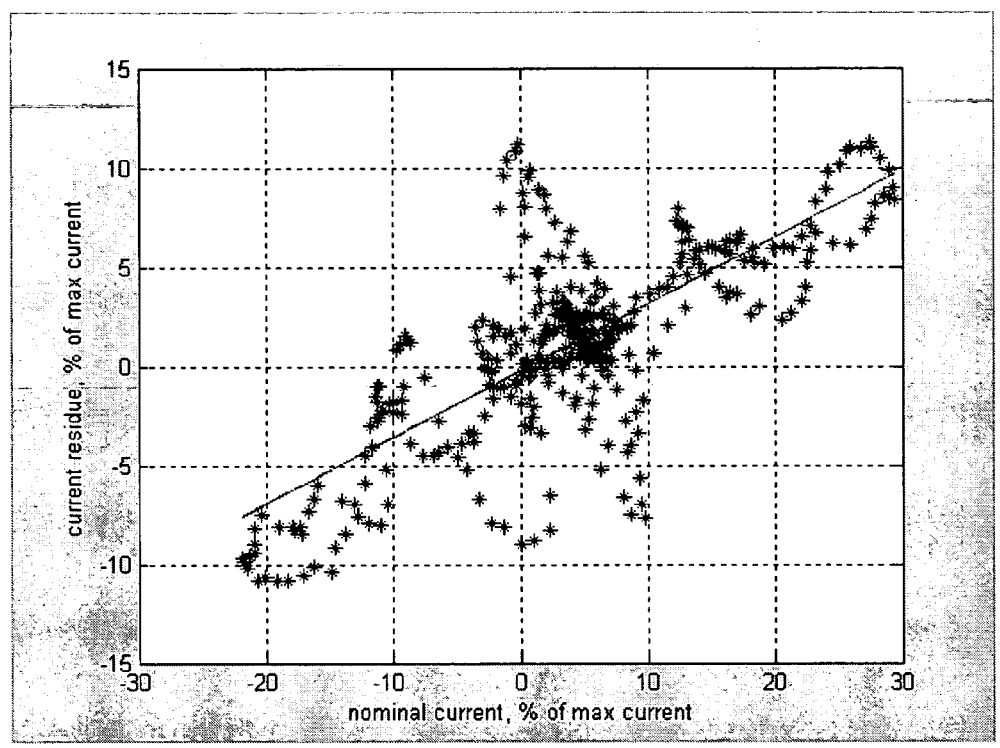
FIG. 17 shows the variation of motor current residual with respect to nominal current.

Faults such as incorrect motor phase angle or demagnetization of the permanent magnets result in a reduction in the effective torque constant of the motor. A higher motor current is required for the same torque output. The torque residual, defined as the difference between the torque under fault conditions and the torque under normal conditions, will be proportional to the torque under normal conditions. This is illustrated by the data shown in FIG. 16 obtained for the Razor traverser. Data was collected as the traverser completed a motion profile defined by a maximum acceleration of 4,500 mm/s$^2$, a maximum velocity of 900 mm/s, the start point at x=0 and the end point at x=1,000 mm. FIG. 17 shows the variation of torque residual with respect to the nominal torque. Note that the plot shows the motor current which is proportional to the torque.

Figure 18:
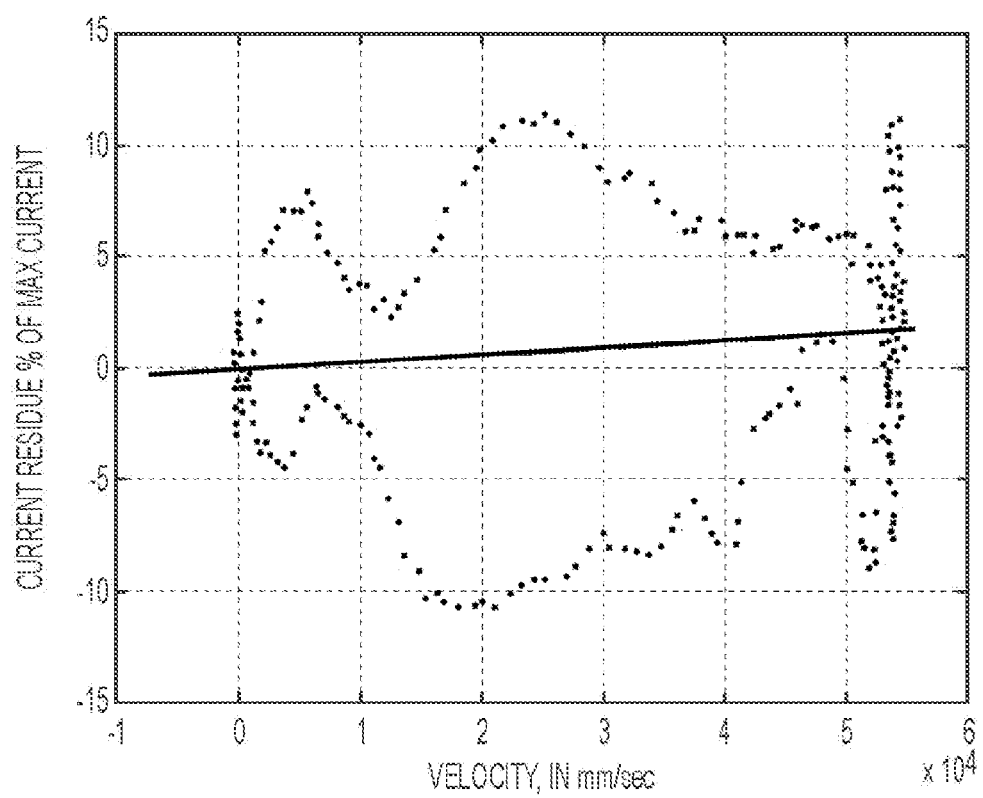
FIG. 18 shows the variation of torque residue with respect to velocity.
Figure 19:
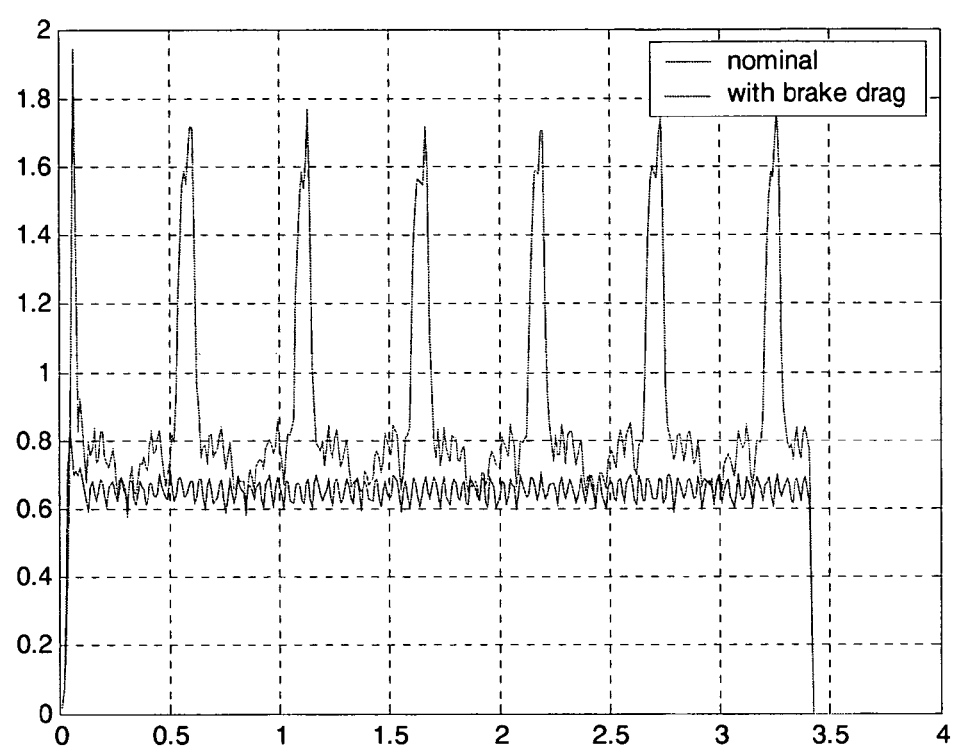
FIG. 19 shows a comparison of Z motor torque with and without brake drag.

The linear regression coefficient indicates the extent to which the torque constant of the motor has decreased. The data in FIG. 17 indicates that, with the wrong phase angle, the torque required is on an average 33.7% greater than the nominal torque. This matches closely with what should be expected due to a phase angle error of 43 degrees. On the other hand, there is little correlation between the torque residual and velocity of the motor as shown in FIG. 18.

Periodic Drag

Figure 20:
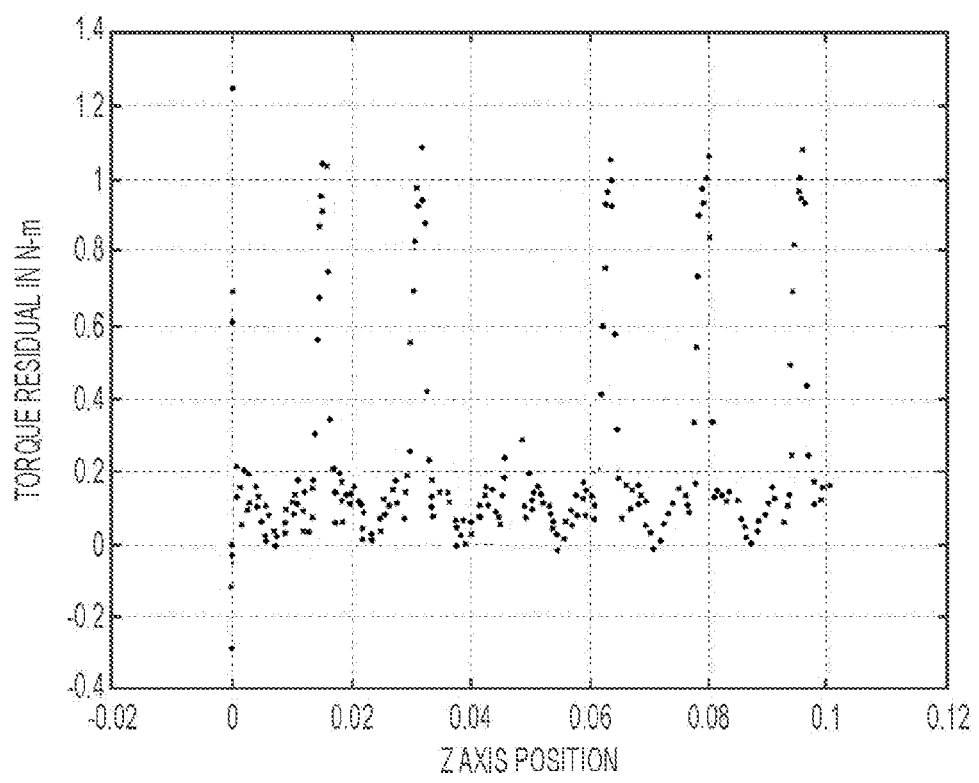
FIG. 20 shows a diagram of residual of Z motor torque.

Faults such as brake drag can induce a periodic drag on the motor. Figure shows the data obtained from the Z axis (vertical lift) of a Reliance robot with no arms. The data represents torque values for a Z motion of 300 mm with a peak velocity of 320 mm/s. Brake drag was induced by preventing the brake shoes from fully disengaging. This resulted in a drag that was periodic in motor position. This is evident from FIG. 20 which shows the variation of the torque residual with respect to position. The period of the variation of the torque residual is approximately 16 mm which is the pitch of the Z ball-screw.

Robot Reference Model

The previous discussions assume that there exists a reference dynamics model of the robot that defines the dynamic behavior of the robot under normal working conditions. Such a model will yield a baseline value for energy dissipation to which the current value of energy dissipation can be compared to determine the state of robot health. The model will also yield the variation of the nominal torque for a given move sequence that can be used to compute the torque residual. Such a model may need to be periodically updated in order to account for significant long term drifts in robot properties that do not necessarily represent health problems. As mentioned above, one of the possible options to determine the baseline robot behavior is the use of a neural network model that represents normal dynamic behavior of the robot.

Figure 21:
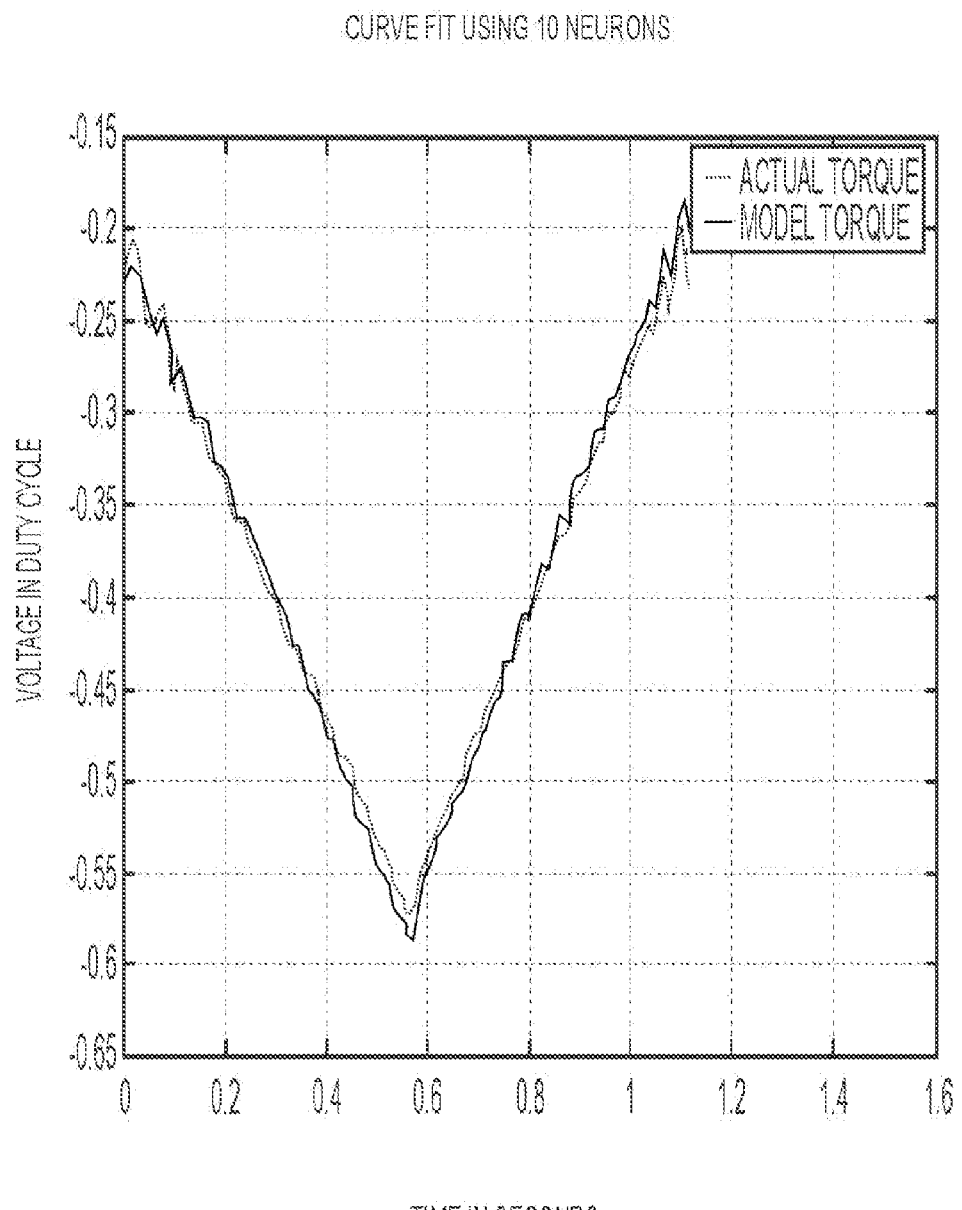
FIG. 21 shows a comparison of model prediction with actual torque values.

Data obtained from a normal robot can be used to build a neural network model of the robot dynamics, and this model can be used as a reference model for health monitoring and fault diagnostics. FIG. 21 shows a comparison of model predicted Z axis torque with the actual torque. The neural network model was built using a radial basis network with 10 neurons. The radial basis network tool provided by Matlab was used for this purpose. The training data for the network comprised position, velocity, acceleration and torque values at 1,300 states.

The present health-monitoring and fault-diagnostic system 100 may be integrated with a global diagnostic tool, such as the GOLDLINK™ global diagnostic tool by Brooks Automation, Inc.

Each function of the health-monitoring and fault-diagnostic system 100 may transmit its output or results to one or more remote computing devices that may perform additional functions. For example, the data collection function 105 may report time histories to a remote server that may perform the pre-processing, analysis and reasoning functions. Other functions within the system may also send data to for remote functions for further computations in order to minimize computing and traffic loads within the system 100.

This may minimize the support needed on site while providing an opportunity to develop and verify the analysis and reasoning algorithms at the remote site, thus eliminating the risk of false alarms reported by the system directly in the field.

The information transmitted to remote functions may include periodic health-monitoring data, automatic status notification, and on-demand information.

Periodic Health-Monitoring Data

One or more of the local functions 105, 110, 115, 120 may continuously record selected signals at a high sampling rate in real time, process characteristics, perform analyses, or perform reasoning functions and transmit the data to a remote site for further processing.

For example, the data collection function 105 could record the following signals for each axis of motion:
(a) Motor voltage (in terms of PWM duty cycle);
(b) Motor current;
(c) Commanded and actual position;
(d) Actual velocity;
(e) Motor temperature.

The local pro-processing function 110 may pre-process the data to calculate a set of characteristics for each operation to determine the following set of characteristics per operation and motion axis:
(a) Date/time stamp;
(b) From/to information;
(c) Dissipated energy;
(d) Maximum current;
(e) Maximum position error;
(f) Settling position error;
(g) Settling time;
(h) Maximum temperature.

The set of characteristics above could be transmitted in periodic batches to a remote server or other computing device for analysis, reasoning, or other functions.

The remote server may also be used to facilitate automatic status notifications from the local functions 105, 110, 115, 120, or the manager 130. Notification information may include:
(a) Operation vs. maintenance change;
(b) Notification of configuration change;
(c) Notification of fatal errors;
(d) Cycle count data sent in pre-defined intervals.

In addition, the remote server or computer connection may allow an upload of the information on demand for support and diagnostic purposes. Exemplary information may include:
(a) Configuration (workspace) information;
(b) Time-stamped command/response/error log;
(c) Data log (from the data collection layer).

In addition, it may be advantageous to provide other features from the remote system, for example, remote upgrade of virus protection software and remote upgrade of controller software.

The system as described is advantageous because it provides a unique set of functions for health monitoring and fault diagnostics. The data collection function acquires time histories of selected variables during operation of the machine being monitored, the pre-processing function calculates specific characteristics of the acquired time histories, the analysis function evaluates characteristics of individual components with which the variables are associated and produces one or more hypotheses about the condition of each of the components, and the reasoning function derives an overall assessment of the machine, including the condition of the individual components of the machine and the degree of confidence that the machine is in good operating condition.

The system may be implemented in a hierarchically distributed manner. For example, multiple instances of each function may reside in, or be associated with, progressively higher level controllers within the machine such that the data required for health monitoring and fault diagnostic purposes are used at the level where sufficient intelligence to process the data is present.

The system is expected to reduce substantially or eliminate completely material damage and unscheduled downtime due to unforeseen failures of robotic manipulators operating in automated manufacturing tools. In addition, in case that a failure occurs, the fault-diagnostic capability of the system is expected to improve the responsiveness, quality and cost of service.

It should be understood that the foregoing description is only illustrative of the embodiments disclosed herein. Various alternatives and modifications can be devised by those skilled in the art without departing from the embodiments. Accordingly, the presently disclosed embodiments are intended to embrace all such alternatives, modifications and variances which fall within the scope of the appended claims.

What is claimed is:

1. A system for condition monitoring and fault diagnosis comprising:
a first controller having a processor configured to perform a data collection function that acquires time histories of selected variables for one or more of the components according to specified sampling parameters;
a second controller having a processor configured to perform a pre-processing function that calculates specified characteristics of each of the time histories individually;
a third controller having a processor configured to perform an analysis function for evaluating the specified characteristics of each of the individual time histories to produce one or more hypotheses of a condition of the one or more components; and
a fourth controller having a processor configured to perform a reasoning function for determining the condition of the one or more components from the one or more hypotheses;
wherein multiple instances of each function reside in progressively higher level controllers within a machine being monitored such that data required for health monitoring and fault diagnostic purposes are used at the level where intelligence to process that data is present.

2. The system of claim 1, further comprising a function for utilizing the determined condition of the one or more components to effect preventative maintenance or service for the components.

3. The system of claim 1, wherein the reasoning function determines a condition of another system in which the one or more components operate from the one or more hypotheses.

4. The system of claim 1, wherein the specified sampling parameters include a sampling period, trigger mode, and number of samples to be recorded for the selected variables.

5. The system of claim 1, wherein each of the first, second, third, and fourth controllers reside in the one or more components.

6. The system of claim 1, wherein the pre-processing function calculates specified characteristics of the time histories by performing mathematical operations on the time histories.

7. The system of claim 1, wherein the analysis function produces the one or more hypotheses by applying one or more algorithms and analysis techniques to the calculated specified characteristics of the time histories.

8. The system of claim 1, wherein the reasoning function includes an expert diagnostic system for determining a condition of the one or more components from the one or more hypotheses.

9. A method of component condition monitoring and fault diagnosis comprising:
acquiring time histories of selected variables for one or more of the components according to specified sampling parameters;

calculating specified characteristics of each of the time histories individually;

evaluating the specified characteristics of each of the individual time histories to produce one or more hypotheses of a condition of the one or more components;

determining the condition of the one or more components from the one or more hypotheses; and utilizing the determined condition of the one or more components to determine if preventative maintenance or service is required for the components;

wherein multiple instances of processors configured to perform acquiring time histories, calculating specified characteristics, evaluating the specified characteristics, determining the condition of the one or more components and utilizing the determined condition reside in progressively higher level controllers within a machine being monitored such that data required for health monitoring and fault diagnostic purposes are used at the level where intelligence to process that data is present.

10. The method of claim 9 including determining a condition of a system in which the one or more components operate from the one or more hypotheses.

11. The method of claim 9, wherein the specified sampling parameters include a sampling period, trigger mode, and number of samples to be recorded for the selected variables.

12. The method of claim 9, wherein acquiring time histories is performed by a controller of the one or more components.

13. The method of claim 9, wherein calculating specified characteristics of the time histories includes performing mathematical operations on the time histories.

14. The method of claim 9, wherein evaluating the characteristics to produce one or more hypotheses of a condition of the one or more components includes applying one or more algorithms and analysis techniques to the calculated specified characteristics of the time histories.

15. The method of claim 9, wherein determining the condition of the one or more components from the one or more hypotheses includes utilizing an expert diagnostic system.

16. A computer readable storage medium encoded with a computer program for component condition monitoring and fault diagnosis, that when run on a computer causes the computer to:

acquire time histories of selected variables for one or more of the components according to specified sampling parameters;

calculate specified characteristics of each of the time histories individually;

evaluate the specified characteristics of each of the individual time histories to produce one or more hypotheses of a condition of the one or more components;

determine the condition of the one or more components from the one or more hypotheses, and utilize the determined condition of the one or more components to determine if preventative maintenance or service is required for the components.

17. The computer program product of claim 16, that when run on a computer causes the computer to utilize the determined condition of the one or more components to effect preventative maintenance or service for the components.

18. The computer program product of claim 16, that when run on a computer causes the computer to determine a condition of a system in which the one or more components operate from the one or more hypotheses.

19. The computer program product of claim 16, wherein the specified sampling parameters include a sampling period, trigger mode, and number of samples to be recorded for the selected variables.

20. The computer program product of claim 16, wherein calculating specified characteristics of the time histories includes performing mathematical operations on the time histories.

21. The computer program product of claim 16, wherein evaluating the characteristics to produce one or more hypotheses of a condition of the one or more components includes applying one or more algorithms and analysis techniques to the calculated specified characteristics of the time histories.

22. The computer program product of claim 16, wherein determining the condition of the one or more components from the one or more hypotheses includes utilizing an expert diagnostic system.

23. A system for component condition monitoring and fault diagnosis comprising:

a first controller having a processor configured to perform a data collection function that acquires time histories of selected variables for one or more components according to specified sampling parameters;

a second controller having a processor configured to perform a pre-processing function that calculates specified characteristics of each of the time histories individually;

a third controller having a processor configured to perform an analysis function for evaluating the specified characteristics of each of the individual time histories to produce one or more hypotheses of a condition of the one or more components;

a fourth controller having a processor configured to perform a reasoning function for determining the condition of the one or more components from the one or more hypotheses; and a fifth controller having a processor configured to perform a manager function that determines the selected variables acquired by the data collection function, triggers data processing in the pre-processing function for calculating the specified characteristics, initiates evaluation of the characteristics by the analysis function to yield the hypotheses, and triggers derivation of the component conditions by the reasoning function;

wherein multiple instances of each function reside in progressively higher level controllers within a machine being monitored such that data required for health monitoring and fault diagnostic purposes are used at the level where intelligence to process that data is present.

24. The system of claim 23, wherein the manager function utilizes the determined condition of the one or more components to effect preventative maintenance or service for the components.

25. The system of claim 23, wherein the reasoning function determines a condition of a system in which the one or more components operate from the one or more hypotheses.

26. The system of claim 23, wherein the specified sampling parameters include a sampling period, trigger mode, and number of samples to be recorded for the selected variables under control of the manager function.

27. The system of claim 23, wherein the pre-processing function calculates specified characteristics of the time histories by performing mathematical operations on the time histories, wherein the mathematical operations are determined by the manager function based on the type of component.

28. The system of claim 23, wherein the analysis function produces the one or more hypotheses by applying one or more algorithms and analysis techniques to calculated specified characteristics of time histories of a group of components operating together as a mechatronic device.

29. The system of claim 28, wherein the reasoning function includes an expert diagnostic system for determining a condition of the mechatronic device from the one or more hypotheses.

30. A system for monitoring component conditions of a semiconductor production tool comprising:
a component controller including a processor having a data collection function that acquires time histories of selected variables of one or more of the components according to specified sampling parameters;
a mechatronic device controller including a processor having a pre-processing function that calculates specified characteristics of each of the time histories individually for those of the one or more components operating together as a mechatronic device;
a group controller for a group of mechatronic devices, the group controller including a processor with an analysis function for evaluating the specified characteristics of each of the individual time histories to produce one or more hypotheses of a condition of the one or more components;
a system controller including a processor having a reasoning function for determining the condition of the one or more components from the one or more hypotheses, and a manager function that determines the selected variables acquired by the data collection function, triggers data processing in the pre-processing function for calculating the specified characteristics, initiates evaluation of the characteristics by the analysis function to yield the hypotheses, and triggers derivation of the component conditions by the reasoning function;
wherein multiple instances of each function reside in progressively higher level controllers within a machine being monitored such that data required for health monitoring and fault diagnostic purposes are used at the level where intelligence to process that data is present.

31. The system of claim 30, wherein the manager function utilizes the determined condition of the one or more components to effect preventative maintenance or service for the components.

32. The system of claim 30, wherein the reasoning function determines a condition of a system in which the one or more components operate from the one or more hypotheses.

33. The system of claim 30, wherein the specified sampling parameters include a sampling period, trigger mode, and number of samples to be recorded for the selected variables under control of the manager function.

34. The system of claim 30, wherein the pre-processing function calculates specified characteristics of the time histories by performing mathematical operations on the time histories, wherein the mathematical operations are determined by the manager function based on the type of component and mechatronic device.

35. The system of claim 30, wherein the analysis function produces the one or more hypotheses by applying one or more algorithms and analysis techniques to calculated specified characteristics of time histories of the group of components operating together as the mechatronic device.

36. The system of claim 30, wherein the reasoning function includes an expert diagnostic system for determining a condition of the mechatronic device from the one or more hypotheses.

37. A continuous health monitoring system comprising:
a first controller including a processor configured to perform a data collection function that acquires time histories of one or more component energy dissipation values during component operations according to specified sampling parameters;
a second controller including a processor configured to perform a pre-processing function that computes metrics using an operational energy dissipation from each of the time histories individually and a baseline energy dissipation;
a third controller including a processor configured to perform an analysis function for evaluating whether the computed metrics exceed predetermined threshold values to produce one or more hypotheses of a condition of the one or more components; and
a fourth controller including a processor configured to perform a reasoning function for determining the condition of the one or more components from the one or more hypotheses,
wherein the data collection, pre-processing, and analysis functions operate in parallel with the component operations and multiple instances of each function reside in progressively higher level controllers within a machine being monitored such that data required for health monitoring and fault diagnostic purposes are used at the level where intelligence to process that data is present.

38. The system of claim 37, wherein the data collection function acquires time histories of mechanical energy dissipation values.

39. The system of claim 37, wherein the data collection function acquires time histories of electrical energy dissipation values.

40. The system of claim 37, wherein the data collection function acquires time histories of energy dissipation values of a robotic joint.

41. The system of claim 37, wherein the data collection function acquires time histories for a predefined sequence of component moves.

42. The continuous health monitoring system of claim 37, wherein the pre-processing function computes a difference between the operational energy dissipation and the baseline energy dissipation as a first metric and an exponentially weighted moving average of the difference as a second metric.

43. The system of claim 37, wherein the pre-processing function computes the predetermined threshold values using a confidence coefficient for predicting a change in the metrics.

44. The system of claim 37, wherein the baseline energy dissipation used by the pre-processing function is acquired from data obtained from a selected move sequence.

45. The system of claim 37, wherein the baseline energy dissipation used by the pre-processing function is acquired from a component model.

46. A method of continuously monitoring system health comprising:
acquiring time histories of one or more component energy dissipation values during component operations according to specified sampling parameters;
computing metrics during the component operations using an operational energy dissipation from each of the time histories individually and a baseline energy dissipation;
in parallel with the component operations, evaluating whether the computed metrics exceed predetermined threshold values to produce one or more hypotheses of a condition of the one or more components;

determining the condition of the one or more components from the one or more hypotheses; and utilizing the determined condition of the one or more components to determine if preventative maintenance or service is required for the components;

wherein multiple instances of processors configured to perform acquiring time histories, computing metrics, evaluating the computed metrics, determining the condition of the one or more components and utilizing the determined condition reside in progressively higher level controllers within a machine being monitored such that data required for health monitoring and fault diagnostic purposes are used at the level where intelligence to process that data is present.

47. The method of claim 46, further comprising acquiring time histories of mechanical energy dissipation values.

48. The method of claim 46, further comprising acquiring time histories of electrical energy dissipation values.

49. The method of claim 46, further comprising acquiring time histories of energy dissipation values of a robotic joint.

50. The method of claim 46, further comprising acquiring time histories for a predefined sequence of component moves.

51. The method of claim 46, further comprising computing a difference between the operational energy dissipation and the baseline energy dissipation as a first metric and an exponentially weighted moving average of the difference as a second metric.

52. The method of claim 46, further comprising computing the predetermined threshold values using a confidence coefficient for predicting a change in the metrics.

53. The method of claim 46, further comprising acquiring the baseline energy dissipation from data obtained from a selected move sequence.

54. The method of claim 46, further comprising acquiring the baseline energy dissipation from data obtained from a component model.

55. A continuous health monitoring system comprising:
a first controller including a processor configured to perform a data collection function that acquires time histories of one or more values related to power consumption by a component during operation according to specified sampling parameters;
a second controller including a processor configured to perform a pre-processing function that computes metrics using an operational power consumption from each of the time histories individually and a power consumption baseline;
a third controller including a processor configured to perform an analysis function for evaluating whether the computed metrics exceed predetermined threshold values to produce one or more hypotheses of a condition of the component; and
a fourth controller including a processor configured to perform a reasoning function for determining the condition of the component from the one or more hypotheses,
wherein the data collection, pre-processing, and analysis functions operate in parallel with the component operations and multiple instances of each function reside in progressively higher level controllers within a machine being monitored such that data required for health monitoring and fault diagnostic purposes are used at the level where intelligence to process that data is present.

56. The system of claim 55, wherein the component power consumption related values include component current consumption.

57. The system of claim 55, wherein the component power consumption related values include one or more of component position, velocity, or acceleration.

58. The system of claim 55, wherein the power consumption baseline used by the pre-processing function is acquired from a component model.

59. The system of claim 55, wherein the pre-processing function computes a difference between the operational power consumption and the baseline power consumption as a first metric and an exponentially weighted moving average of the difference as a second metric.

60. The system of claim 59, wherein the data collection function acquires the time histories for a predefined set of component locations and the pre-processing function computes a difference between the operational power consumption and the baseline power consumption at those predetermined locations as the first metric.

61. The system of claim 59, wherein the data collection function acquires the time histories for a predefined sequence of component moves and the pre-processing function computes an integral of the absolute value of the difference between the operational power consumption and the baseline power consumption over the predefined sequence of component moves as the first metric.

62. The system of claim 55, wherein the pre-processing function computes a fast Fourier transform on portions of the time histories and on portions of the baseline power consumption, and wherein the analysis function monitors peaks emerging or shifting in a frequency spectrum from the transform.

63. A method of continuously monitoring system health comprising:
acquiring time histories of one or more power consumption related values of a component during operation according to specified sampling parameters;
computing metrics during the component operations using an operational power consumption from each of the time histories individually and a power consumption baseline;
in parallel with the component operations, evaluating whether the computed metrics exceed predetermined threshold values to produce one or more hypotheses of a condition of the component;
determining the condition of the component from the one or more hypotheses; and
utilizing the determined condition of the component to determine if preventative maintenance or service is required for the component;
wherein multiple instances of processors configured to perform acquiring time histories, computing metrics, evaluating the computed metrics, determining the condition of the component and utilizing the determined condition of the component reside in progressively higher level controllers within a machine being monitored such that data required for health monitoring and fault diagnostic purposes are used at the level where intelligence to process that data is present.

64. The method of claim 63, wherein the power consumption related values include component current consumption.

65. The method of claim 63, wherein the power consumption related values include one or more of component position, velocity, or acceleration.

66. The method of claim 63, further comprising determining the baseline energy dissipation from a component model.

67. The method of claim 63, further comprising computing a difference between the operational power consumption and the baseline power consumption as a first metric and an exponentially weighted moving average of the difference as a second metric.

68. The method of claim 67, further comprising acquiring time histories for a predefined set of component locations and computing a difference between the operational power consumption and the baseline power consumption at those predetermined locations as the first metric.

69. The method of claim 67, further comprising acquiring time histories for a predefined sequence of component moves and computing an integral of the absolute value of the difference between the operational power consumption and the baseline power consumption over the predefined sequence of component moves as the first metric.

70. The method of claim 63, further comprising computing a fast Fourier transform on portions of the time histories and on portions of the baseline power consumption, and monitoring peaks emerging or shifting in a frequency spectrum from the transform.

71. A continuous health monitoring system comprising:
a first controller including a processor configured to perform a data collection function that acquires time histories of one or more variables of a vacuum component related to operation of a vacuum device during component operations according to specified sampling parameters;
a second controller including a processor configured to perform a pre-processing function that calculates specific characteristics of each of the time histories individually;
a third controller including a processor configured to perform an analysis function for evaluating the characteristics of each of the individual time histories to produce one or more hypotheses about a condition of the vacuum component; and
a fourth controller including a processor configured to perform a reasoning function for determining the condition of the vacuum component from the one or more hypotheses,
wherein the data collection, pre-processing, and analysis functions operate in parallel with the component operations and multiple instances of each function reside in progressively higher level controllers within a machine being monitored such that data required for health monitoring and fault diagnostic purposes are used at the level where intelligence to process that data is present.

72. The system of claim 71, wherein the vacuum device includes an edge gripper.

73. The system of claim 71, wherein the vacuum device includes a suction gripper.

74. The system of claim 71, wherein the one or more vacuum component variables include vacuum pressure readings.

75. The system of claim 71, wherein the one or more vacuum component variables include vacuum pressure transition times.

76. The system of claim 71, wherein the one or more vacuum component variables include operation times of the vacuum component.

77. The system of claim 71, wherein the one or more vacuum component variables include positions of the vacuum component.

78. The system of claim 71, wherein the one or more vacuum component variables include states of a vacuum component.

79. The system of claim 71, wherein the specific characteristics of the time histories include changes in vacuum pressure readings.

80. The system of claim 71, wherein the specific characteristics of the time histories include changes in vacuum pressure transition times.

81. The system of claim 71, wherein the specific characteristics of the time histories include changes in operation times of the vacuum component.

82. The system of claim 71, wherein the specific characteristics of the time histories include changes in positions of the vacuum component.

83. The system of claim 71, wherein the specific characteristics of the time histories include state changes of the vacuum component.

84. The system of claim 71, wherein one or more hypotheses about a condition of the vacuum component includes a vacuum leak in the component.

85. The system of claim 71, wherein one or more hypotheses about a condition of the vacuum component includes a vacuum obstruction in the component.

86. The system of claim 71, wherein one or more hypotheses about a condition of the vacuum component includes a component part failure.

87. A method of continuously monitoring system health comprising:
acquiring time histories of one or more variables of a vacuum component related to operation of a vacuum device according to specified sampling parameters during component operations;
calculating specific characteristics of each of the time histories individually during the component operations;
in parallel with the component operations, evaluating the characteristics to produce one or more hypotheses about a condition of the vacuum component; and
determining the condition of the vacuum component from the one or more hypotheses
utilizing the determined condition of the vacuum component to determine if preventative maintenance or service is required for the vacuum component;
wherein multiple instances of processors configured to perform acquiring time histories, calculating specific characteristics of each of the time histories, evaluating the characteristics, determining the condition of the vacuum component and utilizing the determined condition of the vacuum component reside in progressively higher level controllers within a machine being monitored such that data required for health monitoring and fault diagnostic purposes are used at the level where intelligence to process that data is present.

88. The method of claim 87, wherein the vacuum device includes an edge gripper.

89. The method of claim 87, wherein the vacuum device includes a suction gripper.

90. The method of claim 87, wherein the one or more vacuum component variables include vacuum pressure readings.

91. The method of claim 87, wherein the one or more vacuum component variables include vacuum pressure transition times.

92. The method of claim 87, wherein the one or more vacuum component variables include operation times of the vacuum component.

93. The method of claim 87, wherein the one or more vacuum component variables include positions of the vacuum component.

94. The method of claim 87, wherein the one or more vacuum component variables include states of the vacuum component.

95. The method of claim 87, wherein the specific characteristics of the time histories include changes in vacuum pressure readings.

96. The method of claim 87, wherein the specific characteristics of the time histories include changes in vacuum pressure transition times.

97. The method of claim 87, wherein the specific characteristics of the time histories include changes in operation times of the vacuum component.

98. The method of claim 87, wherein the specific characteristics of the time histories include changes in positions of the vacuum component.

99. The method of claim 87, wherein the specific characteristics of the time histories include state changes of the vacuum component.

100. The method of claim 87, wherein one or more hypotheses about a condition of the vacuum component includes a vacuum leak in the component.

101. The method of claim 87, wherein one or more hypotheses about a condition of the vacuum component includes a vacuum obstruction in the component.

102. The method of claim 87, wherein one or more hypotheses about a condition of the vacuum component includes a part failure in the components.

103. A continuous health monitoring system comprising:
a first controller including a processor configured to perform a data collection function that acquires time histories according to specified sampling parameters in the form of video data related to operations of a device;
a second controller including a processor configured to perform a pre-processing function that calculates specific characteristics of each of the time histories individually;
a third controller including a processor configured to perform an analysis function for evaluating the characteristics of each of the individual time histories to produce one or more hypotheses about a condition of the device; and
a fourth controller including a processor configured to perform a reasoning function for determining the condition of the device from the one or more hypotheses,
wherein the data collection, pre-processing, and analysis functions operate in parallel with the device operations and multiple instances of each function reside in progressively higher level controllers within a machine being monitored such that data required for health monitoring and fault diagnostic purposes are used at the level where intelligence to process that data is present.

104. The system of claim 103, further comprising a video camera for collecting the video data.

105. The system of claim 104, wherein the video camera is positioned to collect the video data from within a workspace of the device.

106. The system of claim 104, wherein the video camera is carried by the device.

107. The system of claim 103, wherein the device operations include pick or place operations.

108. The system of claim 103, wherein the video data includes position data of one or more device components.

109. The system of claim 103, wherein the video data includes image data.

110. The system of claim 109, wherein the image data includes an image of one or more components of the device.

111. The system of claim 109, wherein the image data includes an image of an object carried by the device.

112. The system of claim 103, wherein the specific characteristics of the time histories include an operational repeatability of the device.

113. The system of claim 103, wherein the specific characteristics of the time histories include a positional repeatability of the device.

114. A method of continuously monitoring system health comprising:
acquiring time histories according to specified sampling parameters in the form of video data related to operations of a device while the device is operating;
calculating specific characteristics of each of the time histories individually while the device is operating;
evaluating the specified characteristics of each of the individual time histories to produce one or more hypotheses about a condition of the device while the device is operating;
determining the condition of the device from the one or more hypotheses; and
utilizing the determined condition of the device to determine if preventative maintenance or service is required, for the device;
wherein multiple instances of processors configured to perform acquiring time histories, calculating specific characteristics of each of the time histories, evaluating the specified characteristics, determining the condition of the device and utilizing the determined condition of the device reside in progressively higher level controllers within a machine being monitored such that data required for health monitoring and fault diagnostic purposes are used at the level where intelligence to process that data is present.

115. The method of claim 114, comprising collecting the video data from within a workspace of the device.

116. The method of claim 114, comprising collecting the video data from a video camera carried by the device.

117. The method of claim 114, wherein the device operations include pick or place operations.

118. The method of claim 114, wherein the video data includes position data of one or more device components.

119. The method of claim 114, wherein the video data includes image data.

120. The system of claim 119, wherein the image data includes an image of one or more components of the device.

121. The system of claim 119, wherein the image data includes an image of an object carried by the device.

122. The method of claim 114, wherein the specific characteristics of the time histories include an operational repeatability of the device.

123. The method of claim 114, wherein the specific characteristics of the time histories include a positional repeatability of the device.

124. A continuous health monitoring system comprising:
a first controller including a processor configured to perform a data collection function that acquires time histories of selected variables for one or more components according to specified sampling parameters during component operations including a difference between a predicted torque and a measured torque of the one or more components;
a second controller including a processor configured to perform a pre-processing function that calculates specified characteristics of each of the time histories individually;

a third controller including a processor configured to perform an analysis function for evaluating the specified characteristics of each of the individual time histories to produce one or more hypotheses of a condition of the one or more components; and a fourth controller including a processor configured to perform a reasoning function for determining the condition of the one or more components from the one or more hypotheses, wherein the data collection, pre-processing, and analysis functions operate in parallel with the component operations and multiple instances of each function reside in progressively higher level controllers within a machine being monitored such that data required for health monitoring and fault diagnostic purposes are used at the level where intelligence to process that data is present.

125. The system of claim 124, wherein
the pre-processing function operates to compute metrics using an operational torque from the time histories and a torque baseline; and
the analysis function operates to evaluate whether the computed metrics exceed predetermined threshold values to produce one or more hypotheses of a condition of the one or more components.

126. The system of claim 125, wherein the torque baseline used by the pre-processing function is acquired from a component torque model.

127. The system of claim 124, wherein the selected variables include a difference between a predicted current and a measured current of the one or more components.

128. The system of claim 127, wherein
the pre-processing function operates to compute metrics using an operational current from the time histories and a current baseline; and
the analysis function operates to evaluate whether the computed metrics exceed predetermined threshold values to produce one or more hypotheses of a condition of the one or more components.

129. The system of claim 127, wherein the current baseline used by the pre-processing function is acquired from a component current model.

130. The system of claim 124, wherein the selected variables include a tracking error of the one or more components.

131. The system of claim 130, wherein the data collection function acquires the time histories for predefined component locations and the pre-processing function computes an integral of the absolute value of a tracking error as at least one of the specific characteristics.

132. The system of claim 130, wherein the data collection function acquires the time histories over a predetermined sequence of component moves and the pre-processing function computes an integral of the square of the tracking error as at least one of the specific characteristics.

133. The system of claim 124, wherein at least one of the components includes a motor and the selected variables include at least an actual voltage, current, and velocity of the motor.

134. The system of claim 133, wherein the pre-processing function calculates a modeled current from the actual voltage and velocity, calculates a difference between the actual and modeled current, and determines a maximum variation between the actual and modeled current as at least one of the specific characteristics.

135. The system of claim 134, wherein the analysis function compares the maximum variation with an allowable threshold, and the reasoning layer utilizes results from the analysis layer over several instances of data collection to confirm a change in characteristics.

136. The system of claim 124, wherein at least one of the selected variables includes an incremental position of the one or more components recorded upon receiving an index pulse from an incremental encoder.

137. The system of claim 136, wherein the analysis function computes a difference between incremental positions at successive index pulses and determines if the difference is within a tolerance of a multiple of the number of incremental counts per revolution of the incremental encoder.

138. The system of claim 124, wherein at least one of the selected variables includes an absolute position of the one or more components recorded by an absolute encoder.

139. The system of claim 138, wherein the analysis function computes a difference between the absolute position and an actual position of the one or more components.

140. The system of claim 138, wherein the analysis function computes a difference between the absolute position and an average actual position of the one or more components if the absolute encoder is stationary.

141. The system of claim 124, wherein the one or more components includes a belt and at least one of the selected variables includes a tension of the belt.

142. The system of claim 124, wherein at least one of the selected variables includes a vibration measurement of the one or more components.

143. The system of claim 124, wherein at least one of the selected variables includes a vibration measurement of the one or more components and the pre-processing function calculates a power spectrum of the vibration measurement as one of the specified characteristics.

144. The system of claim 124, wherein at least one of the selected variables includes a temperature of the one or more components.

145. The system of claim 144, wherein the analysis function compares the temperature with a threshold as at least one of the specified characteristics.

146. The system of claim 145, wherein the reasoning function determines the condition of one or more cooling fans from the one or more hypotheses produced by the analysis function.

147. The system of claim 124, wherein at least one of the selected variables includes an output of an over-travel switch indicating that the one or more components have traveled beyond a prescribed limit.

148. The system of claim 124, wherein:
at least one of the selected variables includes an arrival time of a status message and an error count from the one or more components;
the analysis function operates to determine if an interval between successive status packets of the status message exceeds a certain threshold and to compute an error rate for the one or more components; and
the reasoning function identifies a network topology location causing the threshold to be exceeded.

149. The system of claim 124, wherein at least one of the selected variables includes a position repeatability of a substrate carried by the one or more components.

150. The system of claim 124, wherein at least one of the selected variables includes a result of running a virus scan by the one or more components.

151. The system of claim 124, wherein at least one of the selected variables includes a plenum pressure on a first side of a filter component and an environment pressure on a second side of the filter component, and wherein the reasoning function determines if the filter component is clogged from an analysis of the pressures.

152. The system of claim 124, wherein at least one of the selected variables includes an electrostatic charge in an environment of the one or more components.

153. A system for automatic fault diagnosis comprising:
a first controller including a processor configured to perform a data collection function that acquires time histories according to specified sampling parameters of selected power consumption related values for one or more of components of a device in response to deterioration in the operation of the device;
a second controller including a processor configured to perform a pre-processing function that calculates specified characteristics of each of the time histories individually including a range and a minimum variance and requests additional time history acquisition if certain thresholds are not met for the range and minimum variance;
a third controller including a processor configured to perform an analysis function for evaluating the characteristics of each of the individual time histories to produce one or more hypotheses of a condition of the one or more components; and
a fourth controller including a processor configured to perform a reasoning function for determining faults of the one or more components or of the device from the one or more hypotheses;
wherein multiple instances of each function reside in progressively higher level controllers within a machine being monitored such that data required for health monitoring and fault diagnostic purposes are used at the level where intelligence to process that data is present.

154. The system of claim 153, wherein the component power consumption related values include component current consumption.

155. The system of claim 153, wherein the component power consumption related values include one or more of component position, velocity, or acceleration.

156. The system of claim 153, wherein the power consumption baseline used by the pre-processing function is acquired from a component model.

157. A method for automatic fault diagnosis comprising:
acquiring time histories of selected power consumption related values according to specified sampling parameters for one or more components of a device in response to deterioration in the operation of the device;
calculating specified characteristics of each of the time histories individually including a range and a minimum variance and requests additional time history acquisition if certain thresholds are not met for the range and minimum variance;
evaluating the specified characteristics of each of the individual time histories to produce one or more hypotheses of a condition of the one or more components; and
determining faults of the one or more components or of the device from the one or more hypotheses; and
utilizing the determined condition of the one or more components or the device to determine if preventative maintenance or service is required for the components or the device;
wherein multiple instances of processors configured to perform acquiring time histories, calculating specified characteristics of each of the time histories, evaluating the specified characteristics, determining faults and utilizing the determined condition reside in progressively higher level controllers within a machine being monitored such that data required for health monitoring and fault diagnostic purposes are used at the level where intelligence to process that data is present.

158. The method of claim 157, wherein the component power consumption related values include component current consumption.

159. The method of claim 157, wherein the component power consumption related values include one or more of component position, velocity, or acceleration.

160. The method of claim 157, wherein the power consumption baseline used by the pre-processing function is acquired from a component model.

161. A system for automatic fault diagnosis comprising:
a first controller including a processor configured to perform a data collection function that acquires time histories of selected variables according to specified sampling parameters for one or more of components of a device in response to deterioration in the operation of the device;
a second controller including a processor configured to perform a pre-processing function that calculates specified characteristics of each of the time histories individually;
a third controller including a processor configured to perform an analysis function for evaluating the specified characteristics of each of the individual time histories to produce one or more hypotheses of a condition of the one or more components; and
a fourth controller including a processor configured to perform a reasoning function for determining faults of the one or more components or of the device from the one or more hypotheses;
wherein multiple instances of each function reside in progressively higher level controllers within a machine being monitored such that data required for health monitoring and fault diagnostic purposes are used at the level where intelligence to process that data is present.

162. The system of claim 161, wherein at least one of the selected variables includes an actual voltage, torque, velocity, and position of the one or more components during a constant velocity section of a move sequence.

163. The system of claim 162, wherein the pre-processing function operates to:
request additional time histories if the position variables lack a certain range and minimum variance;
compute nominal torque from a model and residual torque as a difference between the nominal torque and the actual torque;
compute a mean and variance of the residual torque; and
compute a Fourier transform of the residual torque with respect to the position variables.

164. The system of claim 163, wherein the analysis function operates to determine if the residual torque exceeds a threshold, report peak frequencies of the Fourier transform, and to determine a distance corresponding to an oscillation period of the residual torque.

165. The system of claim 164, wherein the reasoning function operates to determine the presence of a fault, and to analyze the Fourier transform peaks to determine the fault.

166. The system of claim 161, wherein the selected variables include a tracking error of the one or more components and the pre-processing function operates to compute a Fourier transform of the tracking error as one of the specified characteristics.

167. The system of claim 161, wherein the selected variables include a tracking error and a force of the one or more components.

168. The system of claim 161, wherein the selected variables include an output of a disturbance observer for the one or more components.

169. The system of claim 161, wherein the selected variables include a belt tension of the one or more components.

170. The system of claim 161, wherein the selected variables include a vibration spectrum measurement of the one or more components and the pre-processing function operates to calculate a Fourier transform of the vibration measurement to obtain a vibration power spectrum as one of the specified characteristics.

171. A system for on-demand fault diagnosis comprising:
a first controller including a processor configured to perform a data collection function that acquires time histories of motor excitations and responses of an encoder for a motor of a device on an on-demand basis according to specified sampling parameters;
a second controller including a processor configured to perform a pre-processing function that calculates a frequency response of the device from each of the time histories;
a third controller including a processor configured to perform an analysis function for identifying frequencies from the frequency response corresponding to transverse belt vibrations of a belt drive driven by the motor; and
a fourth controller including a processor configured to perform a reasoning function for comparing the identified frequencies with an allowable range for the belt drive to determine the condition of the belt drive;
wherein multiple instances of each function reside in progressively higher level controllers within a machine being monitored such that data required for health monitoring and fault diagnostic purposes are used at the level where intelligence to process that data is present.

172. A method for diagnosing faults on demand comprising:
acquiring time histories of motor excitations and responses of an encoder for a motor of a device on an on-demand basis according to specified sampling parameters;
calculating a frequency response of the device from each of the time histories individually;
identifying frequencies from the frequency response corresponding to transverse belt vibrations of a belt drive driven by the motor;
comparing the identified frequencies with an allowable range for the belt drive to determine the condition of the belt drive; and
utilizing the determined condition of the belt drive to determine if preventative maintenance or service is required for the belt drive;
wherein multiple instances of processors configured to perform acquiring time histories, calculating a frequency response, identifying frequencies, comparing the identified frequencies and utilizing the determined condition reside in progressively higher level controllers within a machine being monitored such that data required for health monitoring and fault diagnostic purposes are used at the level where intelligence to process that data is present.

173. A system for on-demand fault diagnosis comprising:
a first controller including a processor configured to perform a data collection function that acquires time histories of one or more variables of a vacuum component of a vacuum device on an on-demand basis according to specified sampling parameters;
a second controller including a processor configured to perform a pre-processing function that calculates specific characteristics of each of the time histories individually;
a third controller including a processor configured to perform an analysis function for evaluating the specified characteristics of the individual time histories to produce one or more hypotheses about a condition of the vacuum component; and
a fourth controller including a processor configured to perform a reasoning function for determining the condition of the vacuum component from the one or more hypotheses;
wherein multiple instances of each function reside in progressively higher level controllers within a machine being monitored such that data required for health monitoring and fault diagnostic purposes are used at the level where intelligence to process that data is present.

174. The system of claim 173, wherein the one or more vacuum component variables include vacuum pressure readings.

175. The system of claim 173, wherein the one or more vacuum component variables include vacuum pressure transition times.

176. The system of claim 173, wherein the one or more vacuum component variables include operation times of the vacuum component.

177. The system of claim 173, wherein one or more hypotheses about a condition of the vacuum component include a vacuum leak in the component.

178. The system of claim 173, wherein one or more hypotheses about a condition of the vacuum component includes a vacuum obstruction in the component.

179. The system of claim 173, wherein one or more hypotheses about a condition of the vacuum component include a part failure in the components.

180. A method of continuously monitoring system health comprising:
acquiring time histories of one or more variables of a vacuum component of a vacuum device on an on-demand basis according to specified sampling parameters;
calculating specific characteristics of each of the time histories;
evaluating the specified characteristics of the individual time histories to produce one or more hypotheses about a condition of the vacuum component;
determining the condition of the vacuum component from the one or more hypotheses; and
utilizing the determined condition of the vacuum component to determine if preventative maintenance or service is required for the vacuum component;
wherein multiple instances of processors configured to perform acquiring time histories, calculating specific characteristics of each of the time histories, evaluating the specified characteristics, determining the condition of the vacuum component and utilizing the determined condition of the vacuum component reside in progressively higher level controllers within a machine being monitored such that data required for health monitoring and fault diagnostic purposes are used at the level where intelligence to process that data is present.

181. The method of claim 180, wherein the one or more vacuum component variables include vacuum pressure readings.

182. The method of claim 180, wherein the one or more vacuum component variables include vacuum pressure transition times.

183. The method of claim 180, wherein the one or more vacuum component variables include operation times of a vacuum operated component.

184. The method of claim 180, wherein one or more hypotheses about a condition of the vacuum component includes a vacuum leak in the component.

185. The method of claim 180, wherein one or more hypotheses about a condition of the vacuum component includes a vacuum obstruction in the component.

186. The method of claim 180, wherein one or more hypotheses about a condition of the vacuum component includes a part failure in the component.

187. A system for on-demand fault diagnosis comprising:
a first controller including a processor configured to perform a data collection function that acquires time histories of one or more variables related to a component of a device on an on-demand basis according to specified sampling parameters;
a second controller including a processor configured to perform a pre-processing function that calculates specific characteristics of each of the time histories;
a third controller including a processor configured to perform an analysis function for evaluating the specified characteristics of the individual time histories to produce one or more hypotheses about a condition of the component of the device; and
a fourth controller including a processor configured to perform a reasoning function for determining the condition of the component from the one or more hypotheses;
wherein multiple instances of each function reside in progressively higher level controllers within a machine being monitored such that data required for health monitoring and fault diagnostic purposes are used at the level where intelligence to process that data is present.

188. The system of claim 187, wherein the one or more variables include positions and torques of the component as the device follows a predetermined trajectory.

189. The system of claim 188, wherein the pre-processing, analysis, and reasoning functions operate to identify parameters of a rigid-body dynamic model of the device from the time histories.

190. The system of claim 189, wherein the pre-processing, analysis, and reasoning functions operate to compare parameters of the rigid-body dynamic model representing properties of a joint of the device with baseline parameters of the joint to identify problems.

191. The system of claim 187, wherein the one or more variables include a response of the device as the device moves to positions uniformly distributed on a grid and is excited by a swept-frequency harmonic signal.

192. The system of claim 187, wherein the component of the device includes a motor and the one or more variables include steady state voltage and current values of the motor as the motor is commanded to produce a known force.

193. The system of claim 192, wherein the analysis function operates to compute a winding resistance value for the motor, and to compute current and force residuals by substituting the steady state current values and the commanded force value into equations of a motor model simplified for static load conditions.

194. The system of claim 193, wherein the reasoning function operates to compare the current and force residuals with set thresholds to identify a violation of the motor model.

195. The system of claim 187, wherein the one or more variables include sine and cosine signal values of an encoder of the device as the device moves at a constant velocity.

196. The system of claim 195, wherein the pre-processing function operates to compute a magnitude of an imaginary vector whose Cartesian coordinates are the sine and cosine values.

197. The system of claim 196, wherein the analysis function operates to record maximum and minimum values of the sine and cosine signals and the imaginary vector.

198. The system of claim 197, wherein the reasoning function operates to compare the maximum and minimum values to pre-set thresholds to determine a condition of the encoder.

199. The system of claim 187, wherein the one or more variables include a dimension of a feature scanned by a mapper of the device.

200. The system of claim 199, wherein the pre-processing, analysis, and reasoning functions operates to compare the scanned dimension with a known dimension of the feature to determine a condition of the mapper.

201. The system of claim 187, wherein the one or more variables include a response of the device as the device moves to positions uniformly distributed on a grid and is excited by an impulse, step-frequency or swept-frequency harmonic signal.

202. The system of claim 201, wherein the pre-processing, analysis, and reasoning functions operate to determine a stability measure of a controller of the device from the response.

203. The system of claim 187, wherein the component includes a communication network connected to the device and the one or more variables include a topology of the network.

204. The system of claim 187, wherein the one or more variables include an actual position of the component that causes a light beam to be cut, and wherein the analysis function operates to detect a shift in the actual position.

205. The system of claim 204, wherein the light beam is produced by a beam mapper carried by the component and is cut by a fixed feature.

206. The system of claim 204, wherein the light beam is fixed with respect to a work cell of the device and is cut by the component.

207. The system of claim 187, wherein the one or more variables include a location and orientation of a station mapped by the device.

208. The system of claim 187, wherein at least one of the selected variables includes a result of running a virus scan by the component.

209. A hierarchical system for monitoring component conditions of a machine comprising:
a component controller including a processor having a data collection function that acquires time histories of selected variables of one or more components of the machine according to specified sampling parameters;
a device controller including a processor having a pre-processing function that calculates specified characteristics of each of the time histories for a plurality of the component controllers operating together;
a subsystem controller for a group of the device controllers, the subsystem controller including a processor having an analysis function for evaluating the specified characteristics of the individual time histories to produce one or more hypotheses of a condition of the one or more components; and
a system controller including a processor having a reasoning function for determining the condition of the one or more components from the one or more hypotheses, and having a manager function that determines the selected variables acquired by the data collection function, triggers data processing in the pre-processing function for calculating the specified characteristics, initiates evaluation of the characteristics by the analysis function to yield the hypotheses, and triggers derivation of the component conditions by the reasoning function;

wherein multiple instances of each function reside in progressively higher level controllers within a machine being monitored such that data required for health monitoring and fault diagnostic purposes are used at the level where intelligence to process that data is present.

* * * * *